(12) United States Patent
Hohenhorst et al.

(10) Patent No.: US 8,695,607 B2
(45) Date of Patent: Apr. 15, 2014

(54) APPARATUS, SYSTEMS, AND METHODS FOR CONSTRAINING AND/OR SUPPORTING TISSUE STRUCTURES ALONG AN AIRWAY

(75) Inventors: Winfried Hohenhorst, Essen (DE); Ryan Boucher, San Francisco, CA (US); Eric N. Doelling, Sunnyvale, CA (US); Alex Y. Hsia, San Jose, CA (US)

(73) Assignee: SileoMed, Inc., Santa Clara, CA (US)

( * ) Notice: Subject to any disclaimer, the term of this patent is extended or adjusted under 35 U.S.C. 154(b) by 460 days.

(21) Appl. No.: 12/653,078

(22) Filed: Dec. 7, 2009

(65) Prior Publication Data

US 2010/0294284 A1   Nov. 25, 2010

Related U.S. Application Data

(60) Provisional application No. 61/201,256, filed on Dec. 9, 2008, provisional application No. 61/276,222, filed on Sep. 9, 2009.

(51) Int. Cl.
*A61F 5/56* (2006.01)

(52) U.S. Cl.
USPC .......................................................... 128/848

(58) Field of Classification Search
USPC ........ 128/848; 433/140; 606/9, 23.72; 623/9, 623/23.72
See application file for complete search history.

(56) References Cited

U.S. PATENT DOCUMENTS

| | | | |
|---|---|---|---|
| 5,979,456 A | 11/1999 | Magovern | |
| 5,988,171 A | 11/1999 | Sohn et al. | |
| 6,279,577 B1 | 8/2001 | Savaiano | |
| 6,361,494 B1 | 3/2002 | Lindenthaler | |
| 7,028,691 B2 | 4/2006 | Knudson et al. | |
| 7,090,672 B2 | 8/2006 | Underwood et al. | |
| 7,213,599 B2 | 5/2007 | Conrad et al. | |
| 7,237,554 B2 | 7/2007 | Conrad et al. | |
| 7,337,781 B2 | 3/2008 | Vassallo | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,491,200 B2 | 2/2009 | Underwood | |
| 7,644,714 B2 | 1/2010 | Atkinson et al. | |
| 7,658,192 B2 | 2/2010 | Harrington | |
| 7,703,460 B2 | 4/2010 | Conrad et al. | |
| 2005/0126563 A1 | 6/2005 | Van Der Burg et al. | |
| 2005/0263152 A1 | 12/2005 | Fong | |
| 2006/0070626 A1 | 4/2006 | Frazier et al. | |
| 2006/0150986 A1 | 7/2006 | Roue et al. | |
| 2006/0157055 A1 | 7/2006 | Pflueger et al. | |
| 2006/0235264 A1 | 10/2006 | Vassalo | |
| 2007/0102004 A1 | 5/2007 | Nelson et al. | |
| 2007/0119463 A1 | 5/2007 | Nelson et al. | |
| 2007/0137655 A1 | 6/2007 | Paraschac et al. | |
| 2007/0144533 A1 | 6/2007 | Nelson et al. | |
| 2007/0144534 A1* | 6/2007 | Mery et al. ................... | 128/848 |

(Continued)

OTHER PUBLICATIONS

International Preliminary Report on Patentability; PCT/US09/06413; Jan. 7, 2011.
International Search Report and Written Opinion; PCT/US09/06413, Feb. 3, 2010.

*Primary Examiner* — Patricia Bianco
*Assistant Examiner* — Keri J Nelson
(74) *Attorney, Agent, or Firm* — Ryan Kromholz & Manion, S.C.

(57) ABSTRACT

Apparatus, systems, and methods constrain and/or support tissue structures along an airway.

21 Claims, 53 Drawing Sheets

(56) References Cited

U.S. PATENT DOCUMENTS

| | | |
|---|---|---|
| 2007/0209664 A1 | 9/2007 | Paraschac et al. |
| 2007/0261701 A1 | 11/2007 | Sanders |
| 2008/0035158 A1 | 2/2008 | Pflueger et al. |
| 2008/0041398 A1 | 2/2008 | Hegde et al. |
| 2008/0053461 A1 | 3/2008 | Hirotsuka et al. |
| 2008/0066766 A1 | 3/2008 | Paraschac et al. |
| 2008/0066767 A1 | 3/2008 | Paraschac et al. |
| 2008/0078411 A1 | 4/2008 | Buscemi et al. |
| 2008/0188947 A1 | 8/2008 | Sanders |
| 2009/0014012 A1 | 1/2009 | Sanders |
| 2009/0044814 A1 | 2/2009 | Iancea et al. |
| 2009/0142430 A1 | 6/2009 | Sanders et al. |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137905 A1 | 6/2010 | Weadok et al. |

* cited by examiner

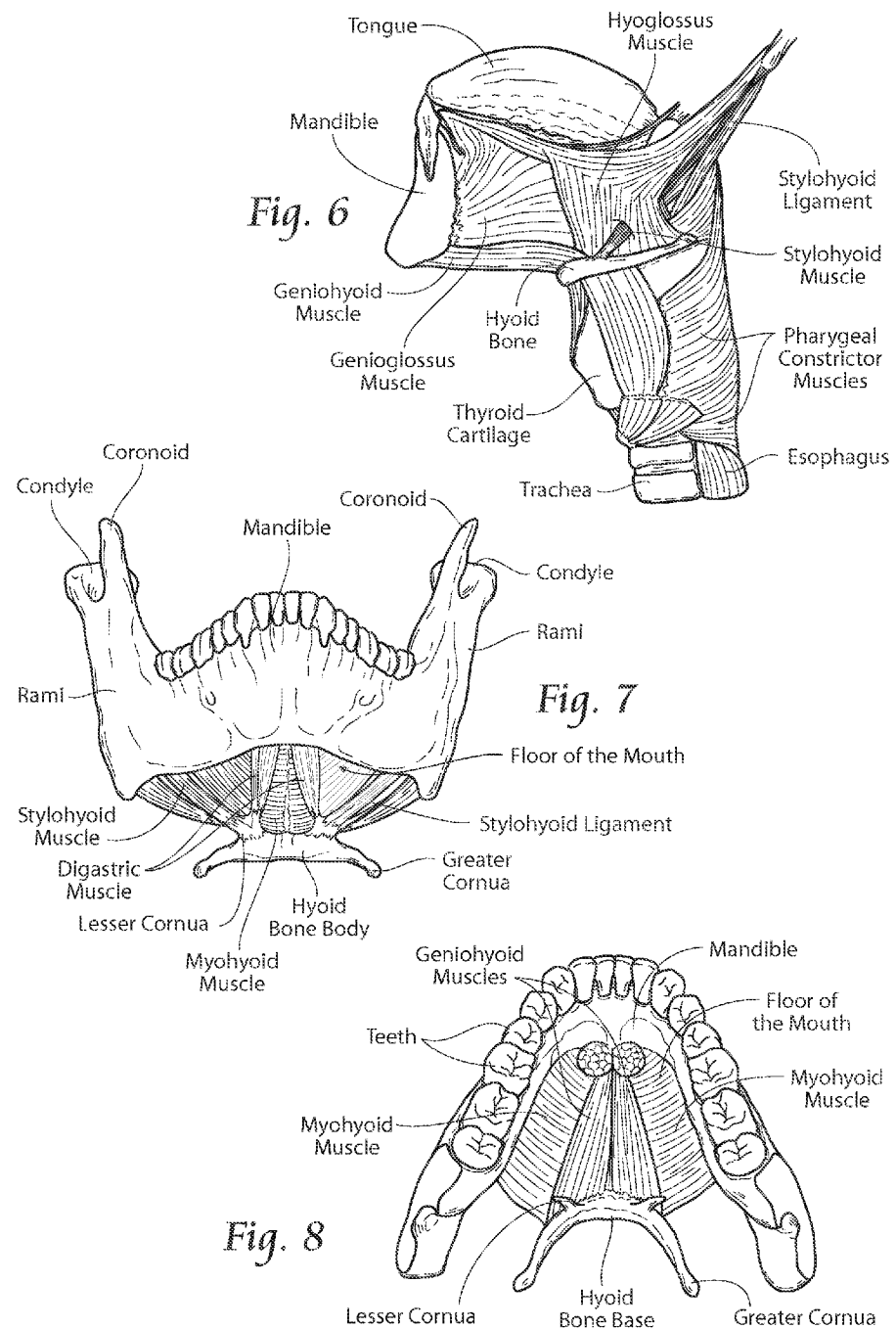

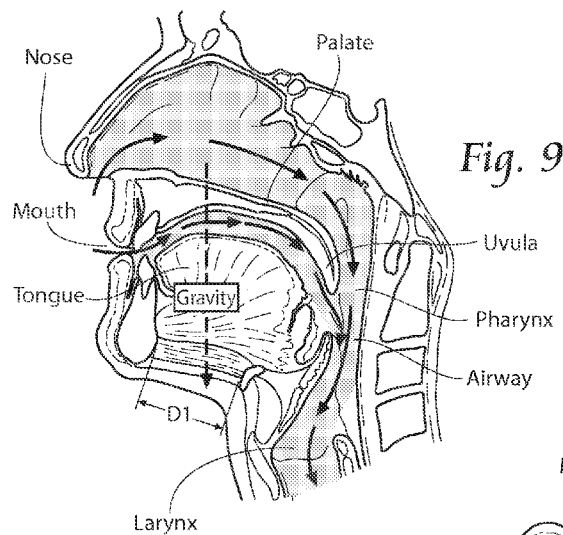
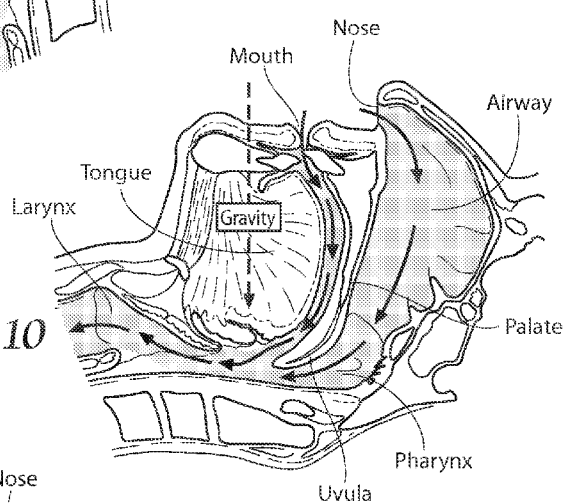
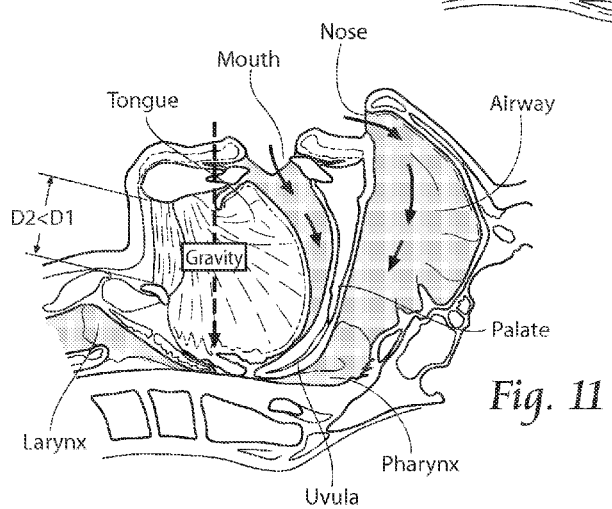

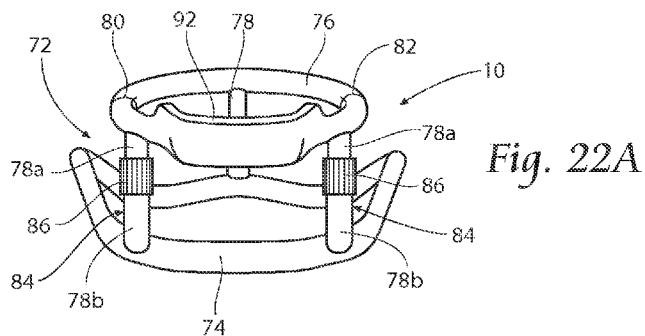
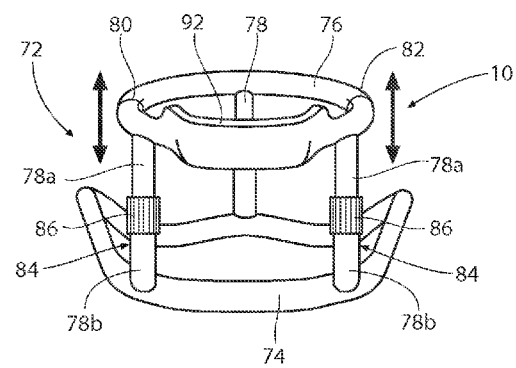
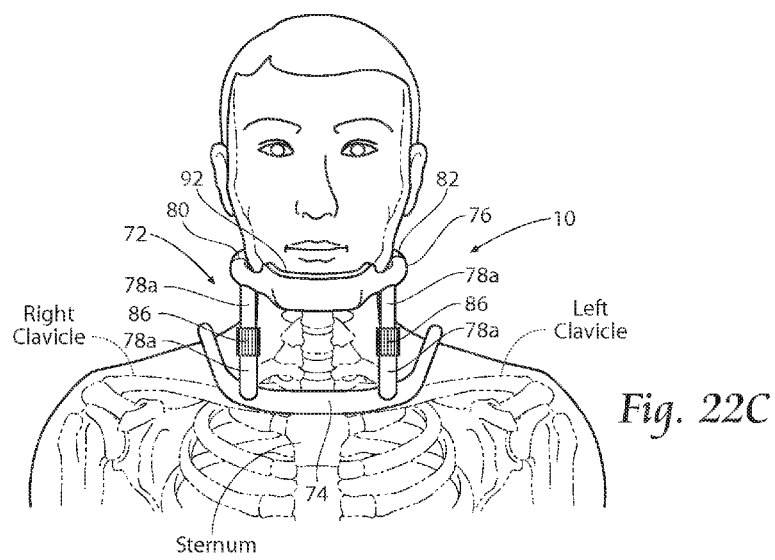

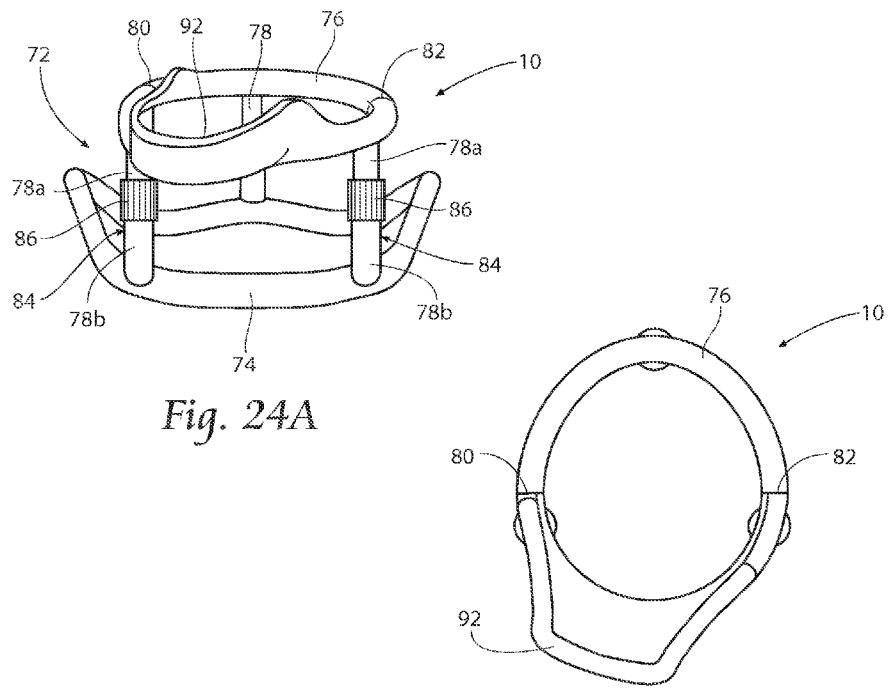
Fig. 24A
Fig. 24B
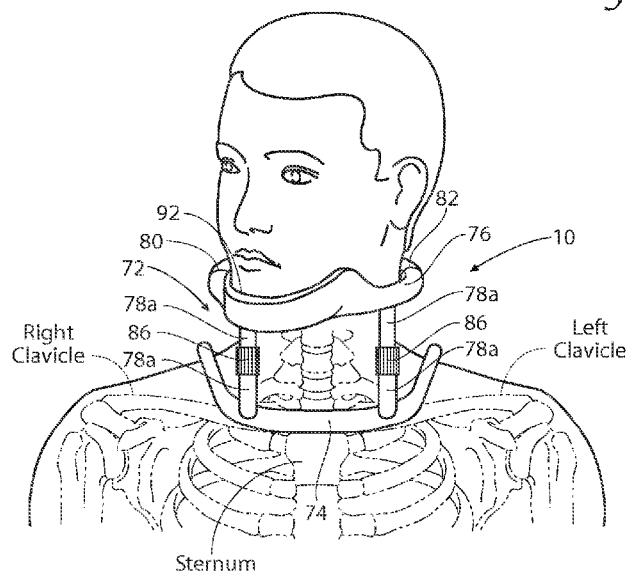
Fig. 24C

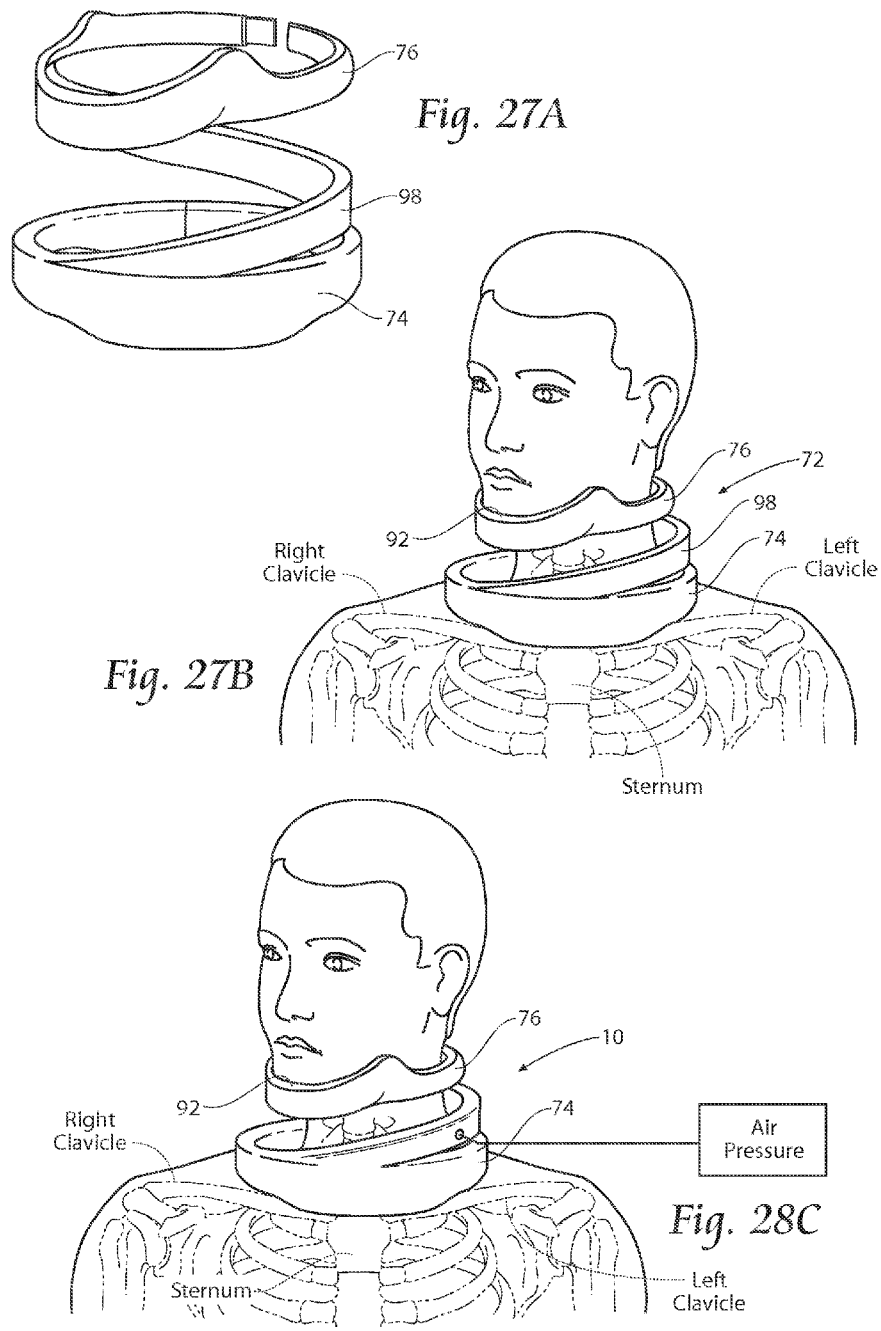

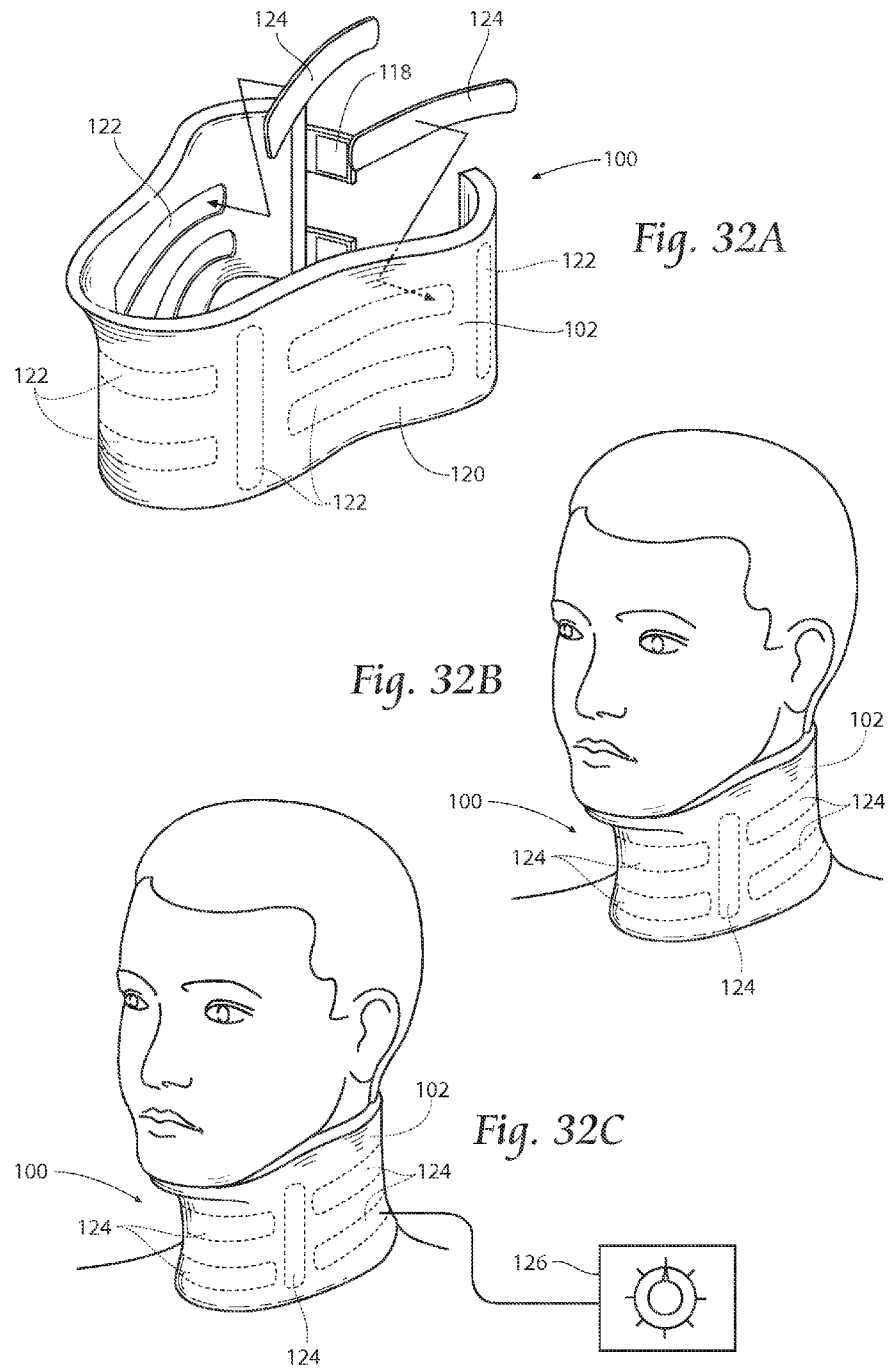

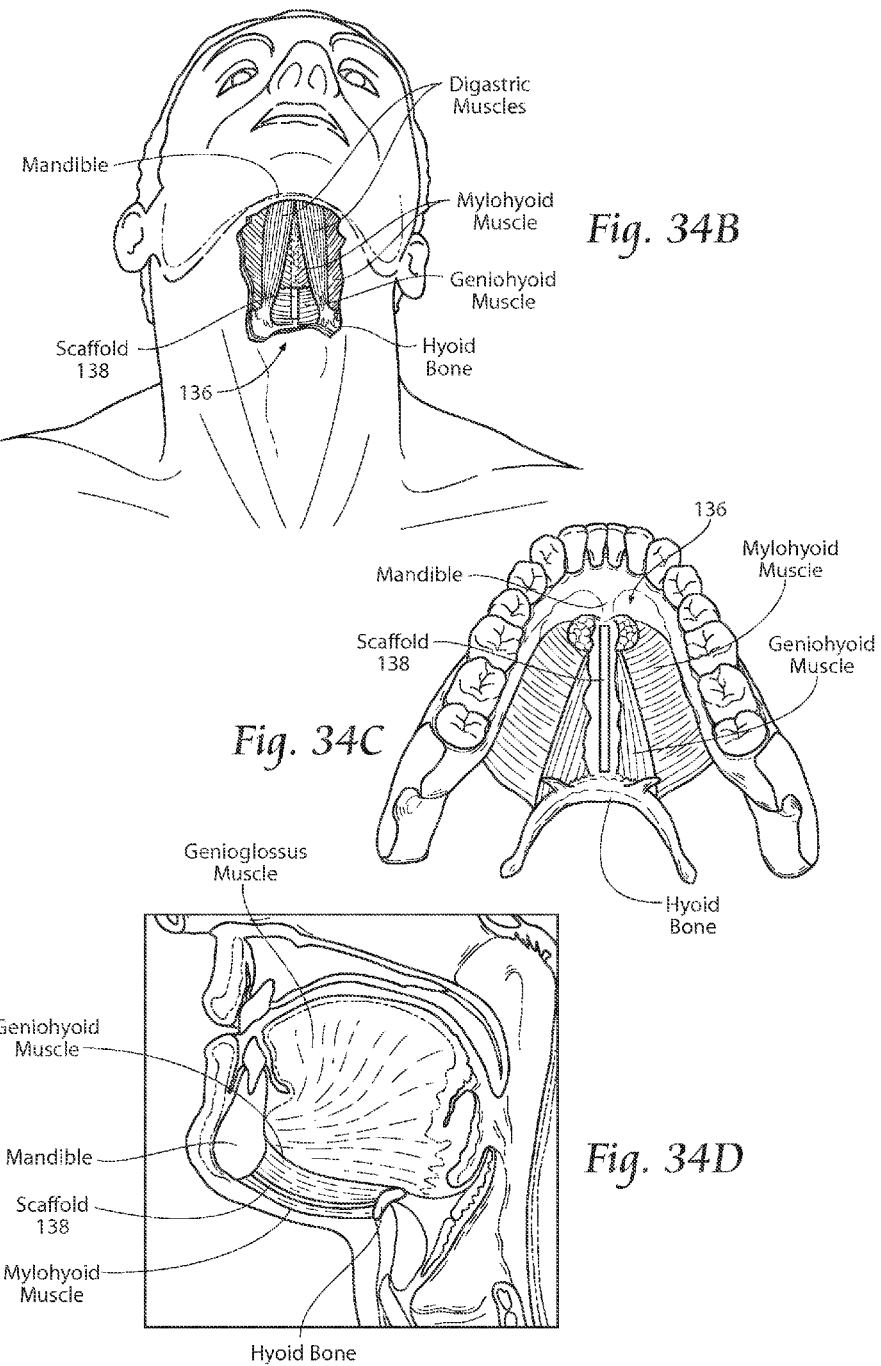

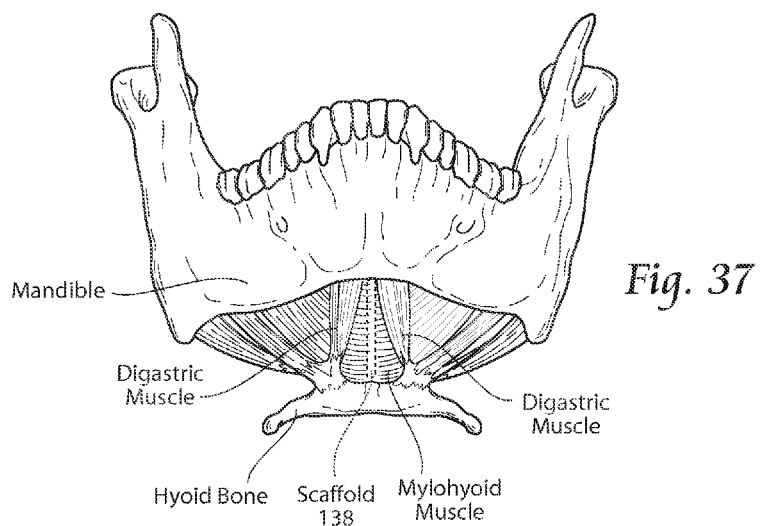
Fig. 37
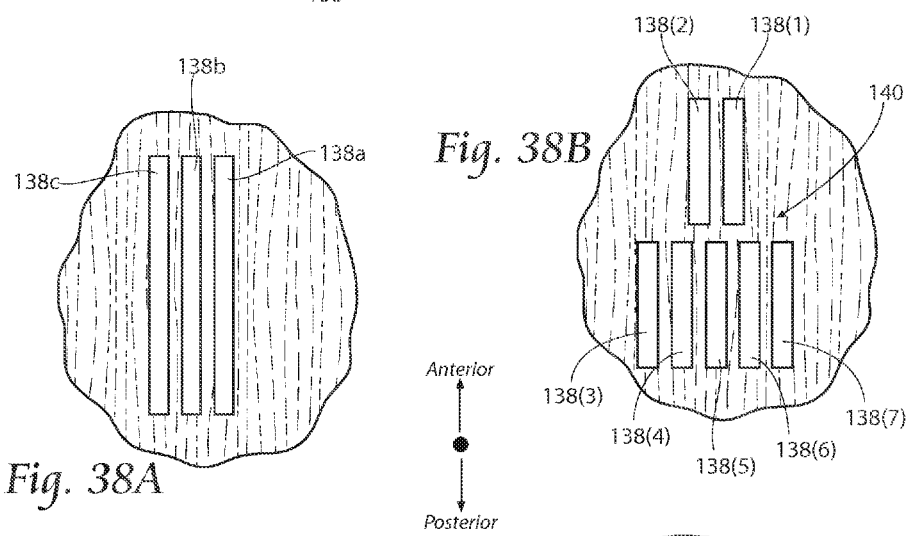
Fig. 38A
Fig. 38B
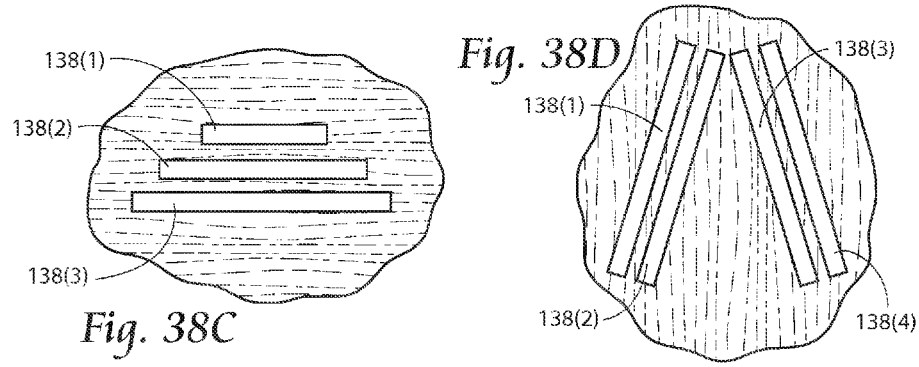
Fig. 38C
Fig. 38D

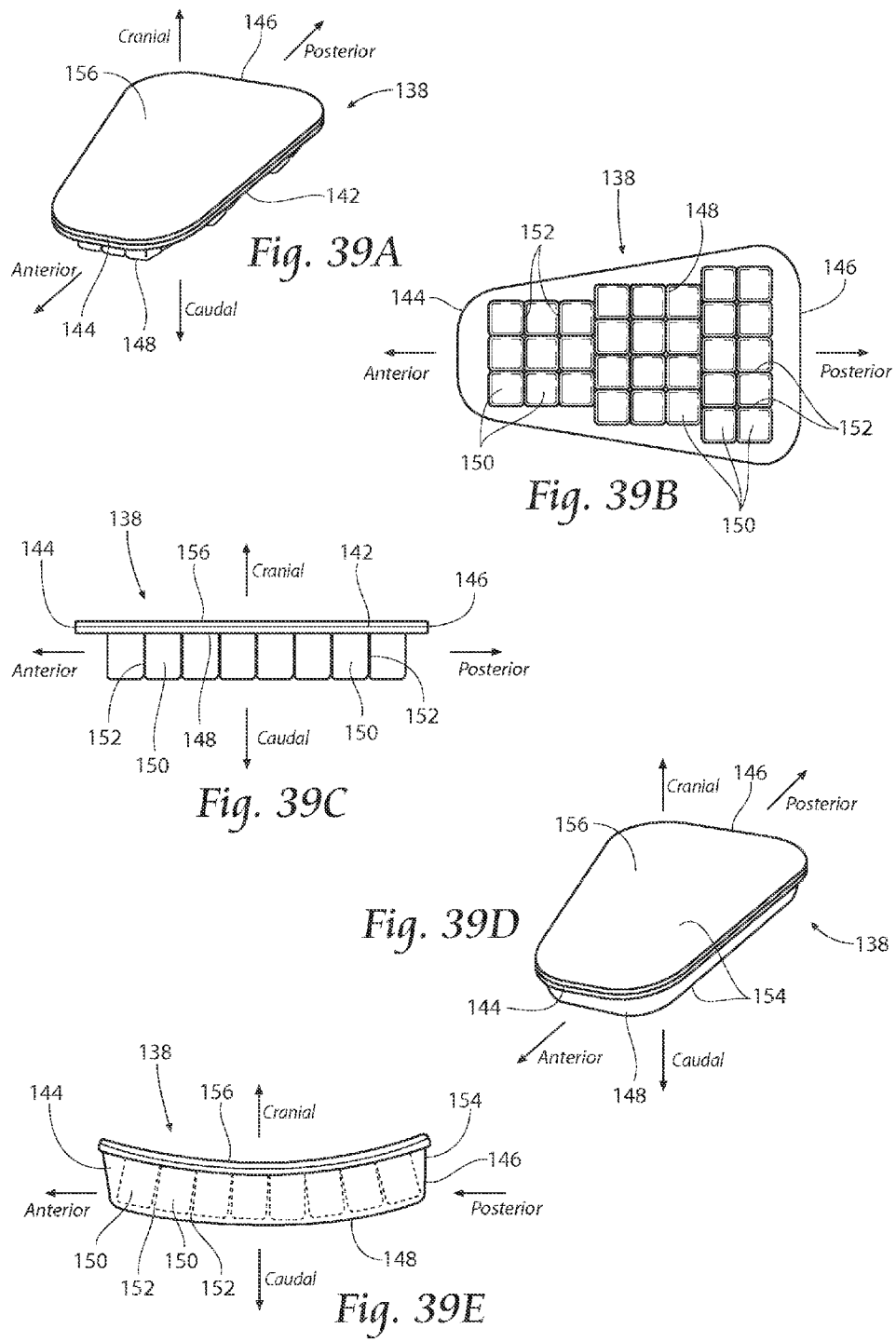

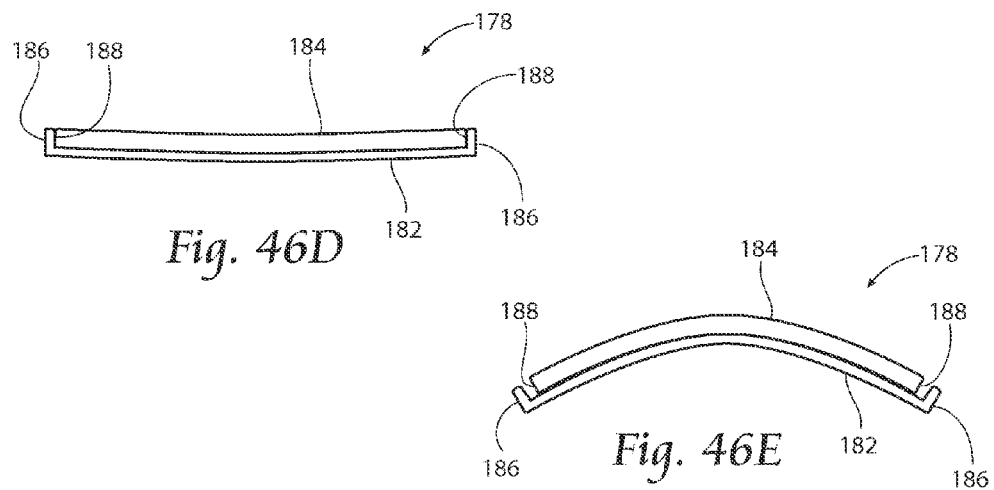
Fig. 46D
Fig. 46E
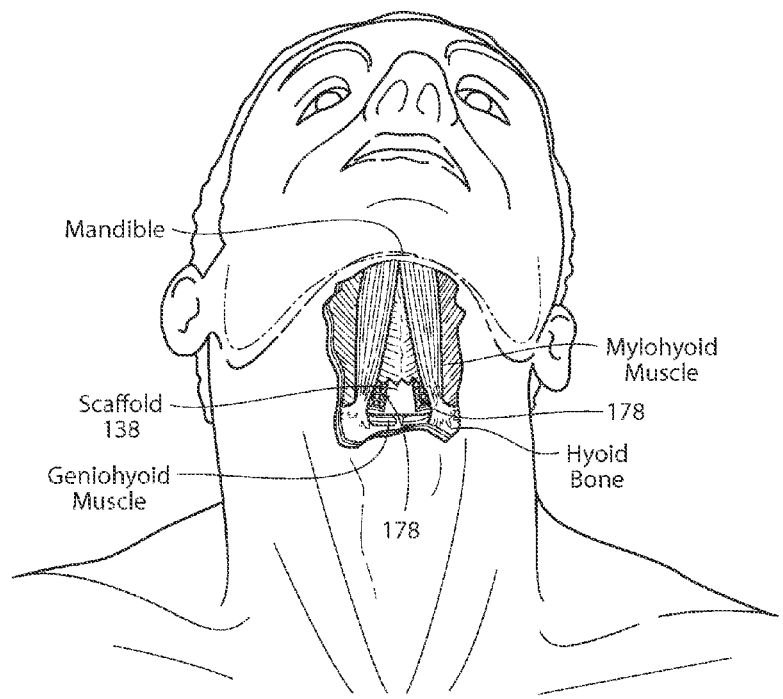
Fig. 47

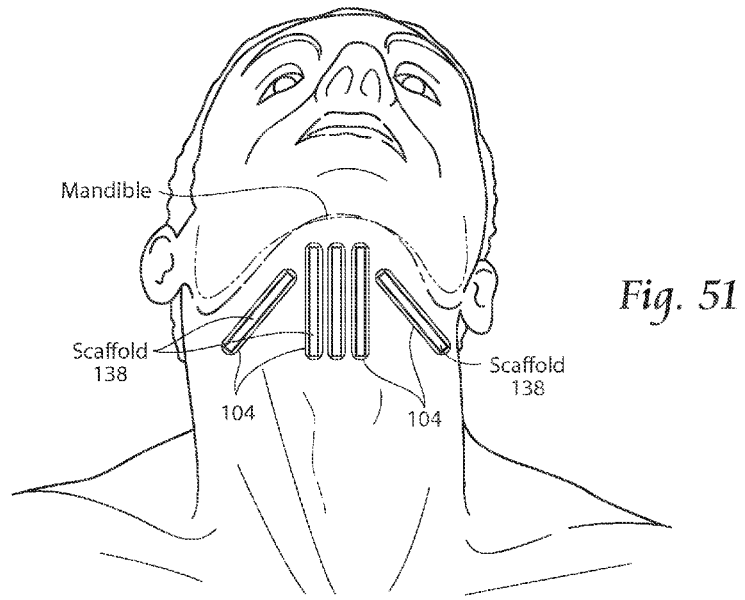
Fig. 51
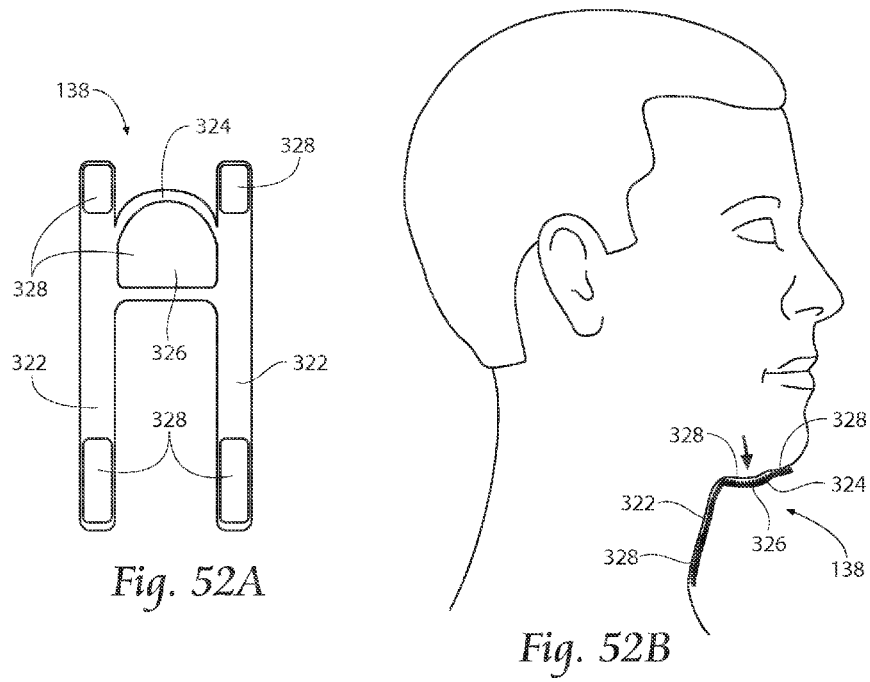
Fig. 52A
Fig. 52B

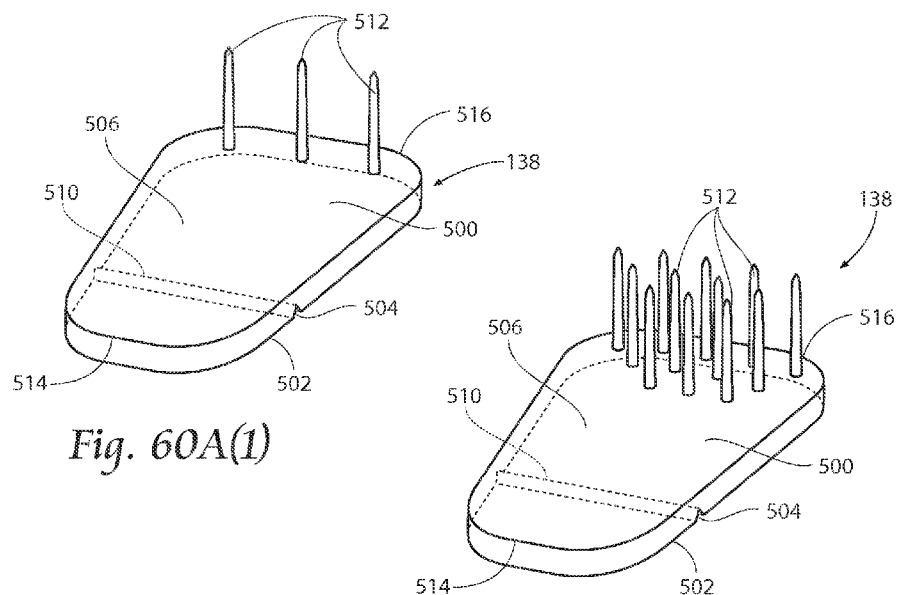
*Fig. 60A(1)*
*Fig. 60A(2)*
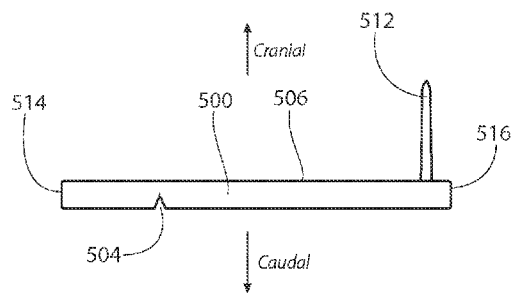
*Fig. 60B*
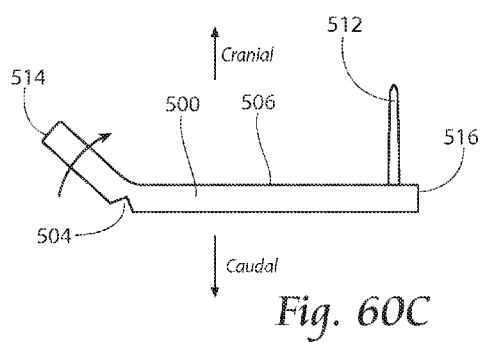
*Fig. 60C*

APPARATUS, SYSTEMS, AND METHODS FOR CONSTRAINING AND/OR SUPPORTING TISSUE STRUCTURES ALONG AN AIRWAY

RELATED APPLICATIONS

This application claims the benefit of U.S. Provisional Patent Application Ser. No. 61/201,256 filed 9 Dec. 2008, and entitled "Apparatus, Systems, and Methods for Constraining and/or Supporting Tissue Structures Along An Airway," which is incorporated herein by reference. This application also claims the benefit of U.S. Provisional Patent Application Ser. No. 61/276,222 filed 9 Sep. 2009, and entitled "Apparatus, Systems, and Methods for Constraining and/or Supporting Tissue Structures Along An Airway," which is also incorporated herein by reference.

BACKGROUND OF THE INVENTION

The Greek word "apnea" literally means "without breath." People with untreated sleep apnea stop breathing repeatedly during their sleep, sometimes hundreds of times during the night and often for a minute or longer.

Obstructive sleep apnea (OSA) is the most common category of sleep-disordered breathing. The muscle tone of the body ordinarily relaxes during sleep. At the level of the throat, the human airway is composed of collapsible walls of soft tissue which can obstruct breathing during sleep. Mild, occasional sleep apnea, such as many people experience during an upper respiratory infection may not be important, but chronic, severe obstructive sleep apnea requires treatment to prevent sleep deprivation and other complications.

Individuals with low muscle tone and soft tissue around the airway (e.g., due to obesity), and structural features that give rise to a narrowed airway are at high risk for obstructive sleep apnea. The elderly are more likely to have OSA than young people. Men are more typical sleep apnea sufferers than women and children, although it is not uncommon in the latter two.

Common symptoms include loud snoring, restless sleep, and sleepiness during the daytime. Diagnostic tests include home oximetry or polysomnography in a sleep clinic.

Sleep apnea is very common, as common as adult diabetes, and affects more than twelve million. Americans, according to the National Institutes of Health. Untreated, sleep apnea can cause high blood pressure and other cardiovascular disease, memory problems, weight gain, impotency, and headaches. Moreover, untreated sleep apnea may be responsible for job impairment and motor vehicle crashes.

Some treatments involve lifestyle changes, such as avoiding alcohol or muscle relaxants, losing weight, and quitting smoking. Many people benefit from sleeping at a 30 degree elevation of the upper body or higher, as if in a recliner. Doing so helps prevent the gravitational collapse of the airway. Lateral positions (sleeping on a side), as opposed to supine positions (sleeping on the back), are also recommended as a treatment for sleep apnea, largely because the gravitational component is smaller in the lateral position. Some people benefit from various kinds of oral appliances to keep the airway open during sleep. There are also surgical procedures to remove and tighten tissue and widen the airway, but these tend to be very intrusive. "Breathing machines" like continuous positive airway pressure (CPAP) may help.

The CPAP machine delivers a stream of compressed air via a hose to a nasal pillow, nose mask or full-face mask, splinting the airway (keeping it open under air pressure) so that unobstructed breathing becomes possible, reducing and/or preventing apneas and hypopneas. This has the additional benefit of reducing or eliminating the extremely loud snoring that sometimes accompanies sleep apnea. Prospective CPAP candidates are often reluctant to use this therapy, since the nose mask and hose to the machine look uncomfortable and clumsy, and the airflow required for some patients can be vigorous. Some patients will develop nasal congestion while others may experience rhinitis or a runny nose. Other conditions that can accompany the use of CPAP include flatulence caused by swallowing too much air; irritation of the skin due to wearing a CPAP mask; upper airway infection; red eye and tear flow; anxiety and feelings of suffocation and/or claustrophobia; and the need to cart around CPAP equipment during travel. Compliance requires self-discipline and resolve. Some patients adjust to the treatment within a few weeks, others struggle for longer periods, and many discontinue treatment entirely.

SUMMARY OF THE INVENTION

The invention provides apparatus, systems, and methods for constraining and/or supporting tissue structures along an airway.

One aspect of the invention provides apparatus, systems, and methods that mechanically support a mandible and/or head in a desired orientation. The apparatus, systems, and methods constrain movement of the head to affirmatively resist collapse of the tongue and tissue structures in, on, or near the floor of the mouth into the airway, thereby moderating or preventing the incidence of sleep apnea.

Another aspect of the invention provides apparatus, systems, and methods that externally brace tissue structures in, on, or near the neck, along the walls of the pharyngeal airway itself. The apparatus, systems, and methods mechanically support these tissue structures in, on, or near the neck in a desired orientation, biased away from the pharyngeal airway. The mechanical support that the apparatus, systems, and methods provide affirmatively resists collapse of the tissue structures in, on, or near the neck toward and into the pharyngeal airway, thereby moderating or preventing the incidence of sleep apnea.

Another aspect of the invention provides apparatus, systems, and methods that locate at least one scaffold in, on, or near tissue structures in the floor of the mouth, between the anterior part of the mandible and the hyoid bone. The scaffold mechanically supports the tissue structures in a desired orientation in the floor of the mouth, to affirmatively resist movement of the tissue structures out of the desired orientation and into the airway, thereby moderating or preventing the incidence of sleep apnea.

In every aspect of the invention, the apparatus, systems, and methods achieve beneficial therapeutic results, moderating or preventing the incidence of sleep apnea, without use of external positive pressure ventilation techniques, like CPAP. The apparatus, systems, and methods thereby avoid the discomfort of the CPAP mask, as well as the conditions that CPAP can cause, such as dryness in the nose and mouth.

Still, if desired, the apparatus, systems, and methods can be used in combination with external positive pressure ventilation techniques, like CPAP. Also, if desired, the apparatus, systems, and methods can be incorporated into overall therapeutic systems, which correct the orientation of tissue structures during sleep according to sensed sleep positions or sleep sound architectures.

BRIEF DESCRIPTION OF THE DRAWINGS

FIG. 6 is an anatomic side elevation view of the extrinsic muscles of the tongue, external larynx, and pharynx.

FIG. 7 is an anatomic anterior view of the mandible and suprahyoid muscles and floor of the mouth, viewed from below.

FIG. 8 is an anatomic superior view of the floor of the mouth and the mylohyoid and geniohyoid muscles.

FIG. 9 is an anatomic side section view of an oral cavity, pharynx, and larynx of an adult human, standing with the mouth closed, annotated to show the passage of air through a normal, unobstructed airway when the person is upright and active.

FIG. 10 is an anatomic side section view of an oral cavity, pharynx, and larynx of an adult human, in a supine sleep position with the mouth closed, annotated to show the passage of air through the airway when the person is asleep, and also showing the effects of gravity on tissue structures along airway that can narrow the airway during sleep.

FIG. 11 is an anatomic side section view of an oral cavity, pharynx, and larynx of an adult human, in a supine sleep position with the mouth opened, showing the effects of gravity and an opened mouth on tissue structures along airway, being annotated to show the collapse of certain tissue structures into the airway and the resultant obstruction of airflow.

FIGS. 22A, 22B, and 22C are perspective views of a representative embodiment of an apparatus like that shown in FIGS. 21A, 21B, and 21C, in which the load bearing structure can be mechanically adjusted in an axial direction.

FIGS. 24A, 24B, and 24C are perspective views of a representative embodiment of an apparatus like that shown in FIG. 12A, comprising a load bearing structure that is sized and configured to be supported between rigid bony anchoring points between the shoulder and mandible, and which constrains the head in a rotationally turned position.

FIGS. 27A, 27B, and 27C are perspective views of a representative embodiment of an apparatus like that shown in FIG. 12A, comprising a helical load bearing structure that is sized and configured to be supported between rigid bony anchoring points between the shoulder and mandible, and which constrains the head in a rotationally turned position.

FIG. 30A FIG. 11 is an anatomic side section view of an oral cavity, pharynx, and larynx of an adult human, in a supine sleep position with the mouth opened, showing the effects of gravity and an opened mouth on tissue structures along airway, being annotated to show the collapse of certain tissue structures into the airway and the resultant obstruction of airflow.

FIGS. 32A and 32B are perspective views of a representative embodiment of an apparatus like that shown in FIG. 28A, in which its ability to brace tissue structures in, on, or near the neck, pharyngeal airway, and/or floor of the mouth can be incremental adjusted by use of insertable stays.

FIG. 32C is a perspective view of a representative embodiment of an apparatus like that shown in FIG. 28A, in which its ability to brace tissue structures in, on, or near the neck, pharyngeal airway, and/or floor of the mouth can be incremental adjusted by use of actuator.

FIGS. 34A, 34B, and 34C are anatomic views of an oral cavity, pharynx, and larynx of an adult human, with the mouth closed, showing the presence of a scaffold implanted in, on, or near tissue structures in the floor of the mouth, which mechanically supports the tissue structures in a desired orientation to stabilize the tissue structures and affirmatively resist their movement into an airway.

FIG. 34D is a side section, more diagrammatic view of a scaffold implanted in, on, or near tissue structures in the floor of the mouth, like that shown in FIGS. 34A, 34B, and 34C, showing fixation of the scaffold to the rigid bone structures of the mandible and/or hyoid bone.

FIGS. 36 and 37 are anatomic views of an oral cavity, pharynx, and larynx of an adult human, with the mouth closed, showing the presence of a scaffold implanted in, on, or near tissue structures in the floor of the mouth, which mechanically supports the tissue structures in a desired orientation to stabilize the tissue structures and affirmatively resist their movement into an airway.

FIGS. 38A/B/C/D are plane views of scaffolds like that shown in FIGS. 34A/B/C and 36/37 implanted in arrays in, on, or near tissue structures in the floor of the mouth.

FIGS. 39A/B/C/D/E and 40 are views of a representative embodiment of a scaffold sized and configured for implantation in, on, or near tissue structures in the floor of the mouth having a preferential bending feature that mechanically supports the tissue structures in a desired orientation and affirmatively resist their movement into an airway.

FIG. 51 is an anatomic anterior view of an individual, showing an array of scaffolds affixed by adhesive material to the external skin along the neck and/or overlying the floor of the mouth.

FIGS. 52A and 52B are views showing a formed unitary flexible bracing structure affixed by adhesive material to the external skin along the neck and/or overlying the floor of the mouth.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

Contents

Figure 1A:
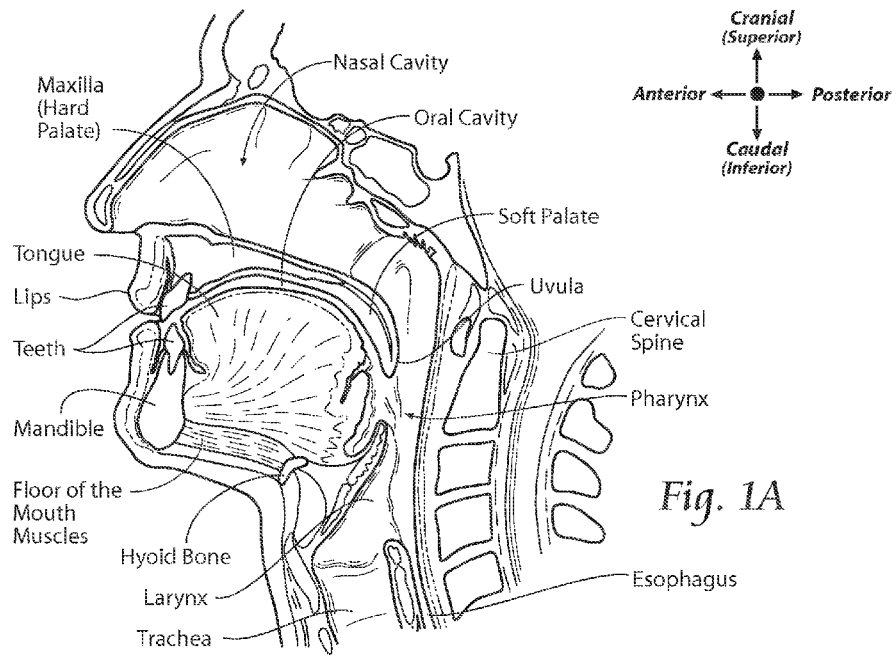
FIG. 1A is an anatomic side section view of an oral cavity, pharynx, and larynx of an adult human, with the mouth closed.

The description that follows is divided into the following main sections and sub-sections:

I. Pertinent Anatomy
  A. Oral Cavity or Mouth
    1. The Palate (Roof of the Mouth)
    2. The Floor of the Mouth
    3. The Tongue
    4. The Pharynx (Pharyngeal Airway)
  B. The Mandible
  C. The Neck
    1. The Hyoid Bone
    2. Extrinsic Muscles of the Tongue Attached to Hyoid
    3. Other Muscles in the Neck Attached to Hyoid
    4. Swallowing
II. Collapse of the Airway
III. Apparatus and Methods for Constraining The Mandible and/or Head
  A. Overview
    1. First Constraint Condition (Maintain Closure of the Mouth)
    2. Second Constraint Condition (Limit Inferior Rotation of the Head)
    3. Third Constraint Condition (Provide an Anterior Position to the Jaw)
    4. Fourth Constraint Condition (Twist/Elevate the Head)
  B. Representative Embodiments
    1. Mandible/Head Support
      (i) Chin Support with Neck Piece
      (ii) Pressure-Sensitive Adhesive
      (iii) Variable Constrain of Mandible and/or Head
      (iv) Dynamic Constrain of Mandible and/or Head
      (v) Anchored Load bearing Structures
      (vi) Helical Load Bearing Structure
IV. Apparatus and Methods for Bracing Tissue Structures In, On, or Near the Neck
  A. Overview
    1. Variable Neck Bracing/Reshaping
    2. Dynamic Neck Bracing/Reshaping
V. Scaffolds In, On, or Near the Floor of the Mouth
  A. Overview
  B. Representative Placement
    1. Mylohyoid-Geniohyoid
    2. Geniohyoid-Genioglossus
    3. Digastric-Mylohyoid
  C. Representative Scaffold Configurations
    1. General Physical Characteristics
    2. Preferential Bending Characteristic
    3. Representative Implantation Methods
    4. External Scaffolds and Combinations
VI. Enhanced Anchorage of the Tongue to Muscles in the Floor of the Mouth
VII. Preferential Bending in Floor of the Mouth with Interaction with Tongue
I. Pertinent Anatomy
  A. The Oral Cavity or Mouth FIG. 1A is an anatomic view (in section) of an oral cavity in the head of an adult human. In human anatomy, the oral cavity—which will also be called the mouth—constitutes the orifice through which food and air enter the body.

Figure 2A:
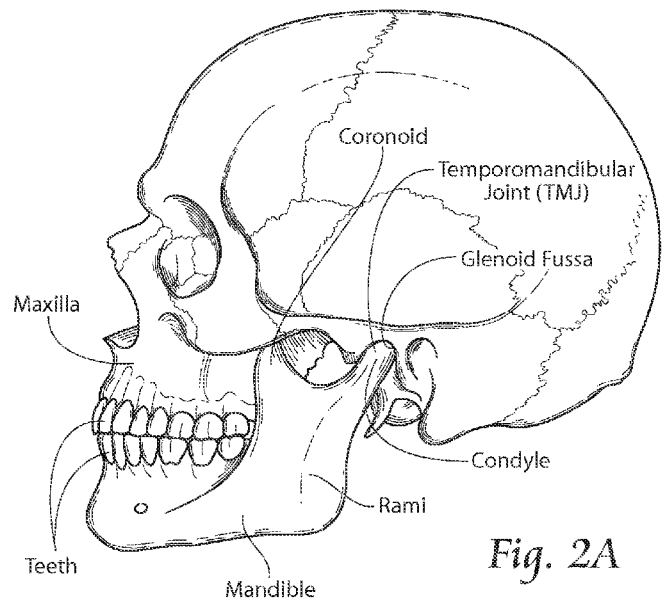
FIG. 2A is an anatomic side elevation view of a human skull, with the jaws closed.
Figure 2B:
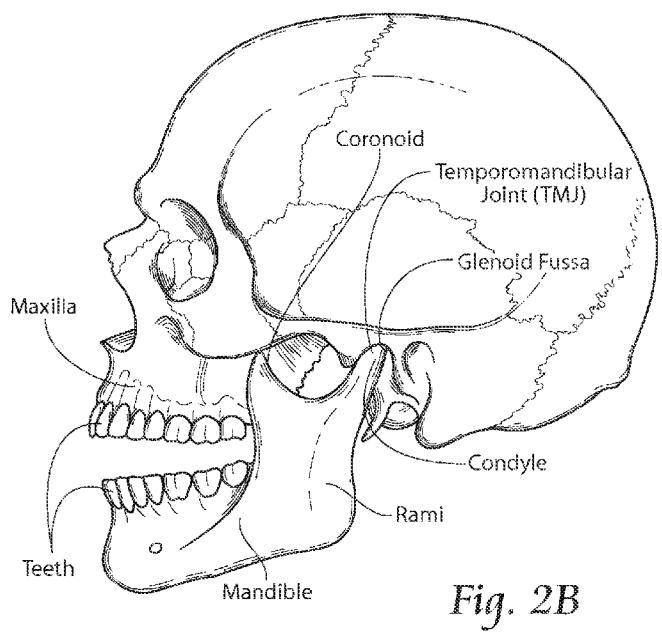
FIG. 2B is an anatomic side elevation view of a human skull, with the jaws opened.

As further delineated in FIGS. 2A and 2B, a pair of bones, called the jaws, form the skeletal framework of the mouth. The jaws contain teeth and include a movable lower jaw (the mandible) and a fixed upper jaw. The jaws function by moving in opposition to each other (as FIGS. 1A/B and 2A/B show) and are used for biting, chewing, and the handling of food.

Figure 1B:
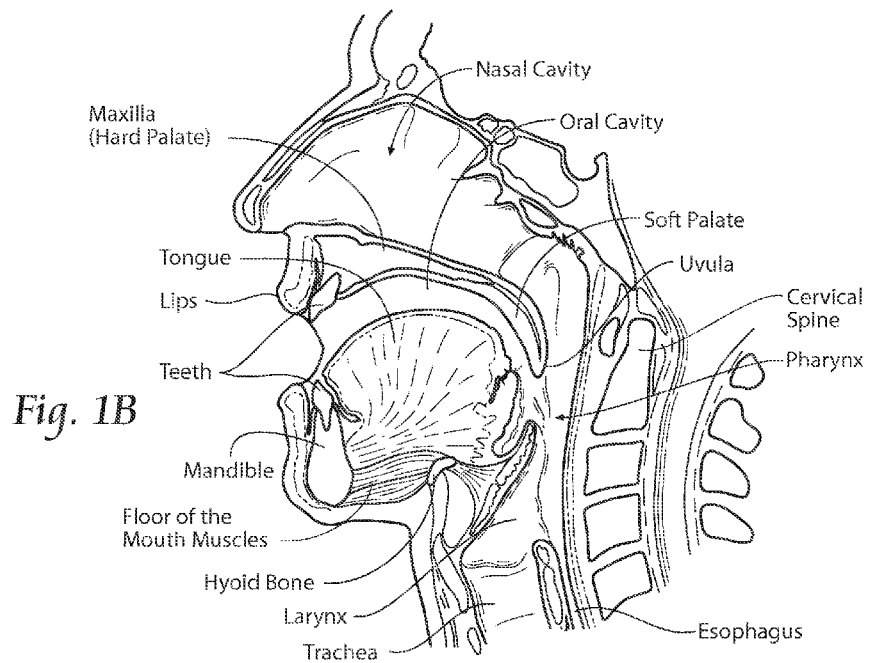
FIG. 1B is an anatomic side section view of an oral cavity, pharynx, and larynx of an adult human, with the mouth opened.

Referring back to FIGS. 1A and 1B, the interior non-skeletal boundaries of the oral cavity are defined by the lips, the cheeks (no shown), the hard and soft palates, and the throat or pharynx. The oral cavity or mouth opens to the outside at the lips (which will also be called the front or anterior region of the oral cavity). Lowering of the mandible relative to the maxilla opens the mouth, as FIG. 1B shows. The oral cavity empties into the pharynx (which will also be called the back or posterior region of the oral cavity).

FIG. 1A illustrated the nomenclature that will be used to depict direction. Anterior and posterior mean front and back, respectively, as just described. Superior or cranial and inferior or caudal mean up and down, respectively.

As FIGS. 1A and 1B show, the pharynx is a cone-shaped passageway leading from the oral cavity (and nasal cavity) to the esophagus and larynx. The esophagus leads to the stomach. It is the path through which food entering the oral cavity is carried into the stomach for digestion in the digestive system. The larynx is a hollow, tubular structure connected to the top of the windpipe (trachea). Air entering the oral cavity passes through the larynx on its way to the lungs. The larynx also produces vocal sounds, and for this reason is also called the voice box. The larynx also prevents the passage of food and other foreign particles into the lower respiratory tracts.

The chief structures of the mouth are the teeth, palate, and tongue. The teeth, carried by the articulating jaws, tear and grind ingested food into small pieces that are suitable for digestion. The palate separates the mouth from the nasal cavity, allowing separate passages for air and for food. The tongue is a large muscle firmly anchored to the floor of the mouth. The tongue positions and mixes food and also carries sensory receptors for taste. In addition to its primary role in the intake and initial digestion of food and the intake of air during breathing, the mouth and its structures are essential in humans to the formation of speech.

1. The Palate (the Roof of the Mouth)

The palate (see FIGS. 1A and 1B) constitutes the roof of the mouth. It separates the oral and nasal cavities. The palate consists of an anterior hard palate of bone and, in humans, a posterior soft palate that has no skeletal support and terminates in a fleshy, elongated projection called the uvula.

The hard palate composes two-thirds of the total palate area. The hard palate is a plate of bone covered by a moist, durable layer of mucous-membrane tissue, which secretes small amounts of mucus. This layer forms several ridges that help grip food while the tongue agitates it during chewing. The hard palate provides space for the tongue to move freely and supplies a rigid floor to the nasal cavity so that pressures within the mouth do not close off the nasal passage.

The soft palate is composed of muscle and connective tissue, which give it both mobility and support. This palate is very flexible. When elevated for swallowing and sucking, it completely blocks and separates the nasal cavity and nasal portion of the pharynx from the mouth and the oral part of the pharynx. While elevated, the soft palate creates a vacuum in the oral cavity, which keeps food out of the respiratory tract.

2. The Floor of the Mouth

The floor of the mouth (see FIG. 3) is a tissue region that is bounded anteriorly by the mandible and posteriorly by the hyoid. The floor of the mouth is immediately surrounded by other tissue structures, such as muscles attached to the hyoid and/or mandible (as will be described later), which are mutually interconnected and mutually affected by the condition and orientation of tissue in the floor of the mouth. The floor of the mouth can be seen only when the tongue is raised. In the midline is a prominent fold (called the frenulum linguae), to which the tongue is anchored.

3. The Tongue

Figure 3:
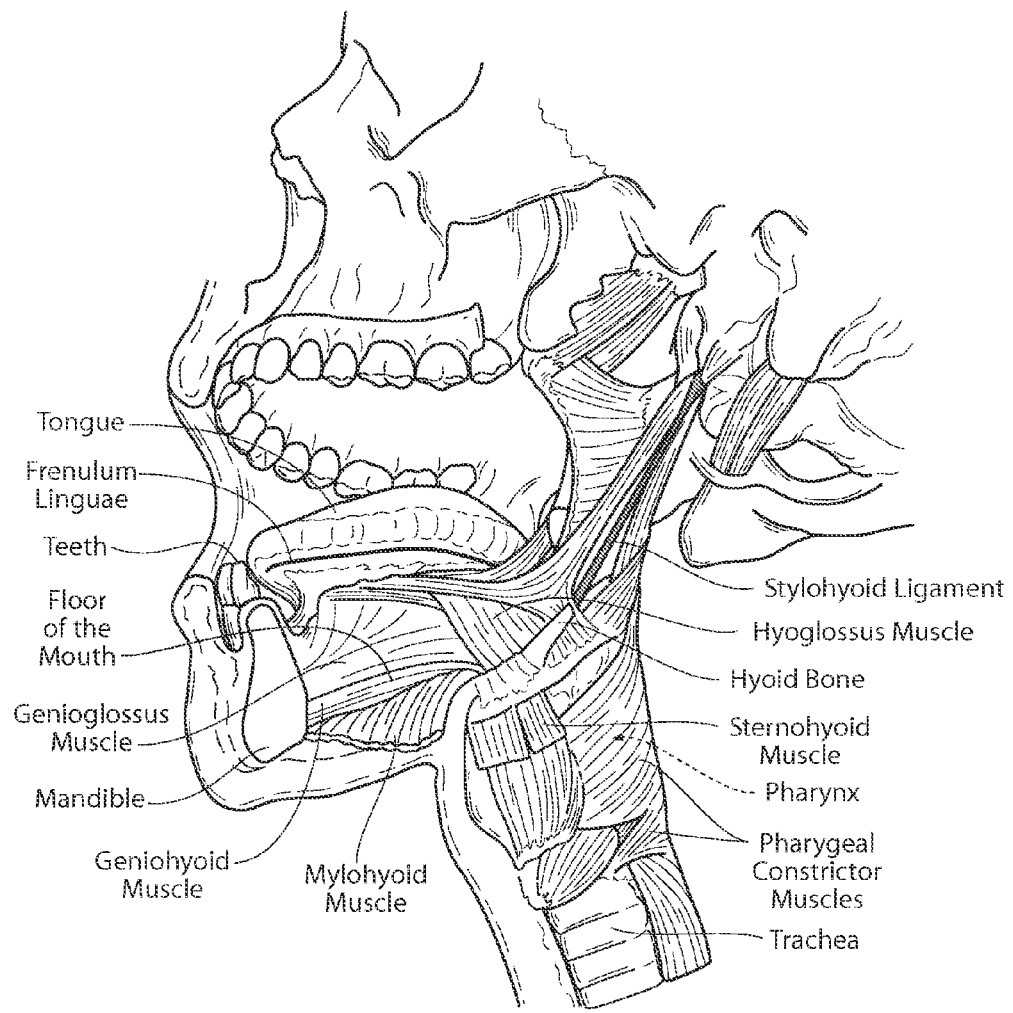
FIG. 3 is an anatomic lateral view of the oral cavity shown in FIG. 1B, with superficial and deep facial structures and left half of the mandible removed to show muscles of the tongue and pharynx, some of which have been cut for the purpose of illustration.

The tongue (shown enlarged in FIG. 4, and which is also shown in FIGS. 1A and 1B and 3) is a muscular organ located on the floor of the mouth. The tongue is a mobile muscular organ that can assume a variety of shapes and positions. The tongue rests partly in the oral cavity and partly in the pharynx (FIGS. 1A and 2B show).

The tongue is an extremely mobile structure in humans and an important accessory organ in such motor functions as speech, chewing, and swallowing. In conjunction with the cheeks, it is able to guide and maintain food between the upper and lower teeth until mastication is completed.

At rest, the tongue occupies essentially all of the oral cavity proper. The tongue is involved with mastication, taste, deglutition, and oral cleansing. Its two major functions are forming words during speaking and squeezing food into the pharynx when swallowing.

4. The Pharynx (Pharyngeal Airway)

Referring back to FIGS. 1A and 1B, the pharynx serves both respiratory and digestive functions. For the respiratory function, the pharynx serves as the essential airway for the body. Blockage of the airway of the pharynx can lead to a cessation of breathing and resultant disruption or interruption of the normal body functions.

As FIG. 6 shows, thick fibers of constrictor muscles and connective tissue attach the pharynx to the base of the skull and surrounding structures. Both circular and longitudinal constructor muscles occur in the walls of the pharynx. The circular muscles form constrictions that help push food to the esophagus and prevent air from being swallowed. The longitudinal muscles lift the walls of the pharynx during swallowing.

B. The Mandible

Please ref to FIGS. 2A and 2B. The mandible is the lower jaw. It is a U-shaped bone having alveolar processes that house the mandibular teeth.

The ascending parts of the mandible at the side are called rami (branches). The joints by means of which the lower jaw is able to make all its varied movements are between a rounded knob, or condyle, at the upper back corner of each ramus and a depression, called a glenoid fossa, in each temporal bone. The hinge-type joint that is formed between these articular surfaces is called the temporomandibular joint (TMJ). Another, rather sharp projection at the top of each ramus and in front, called a coronoid process, does not form part of a joint. Attached to it is the temporalis muscle, which serves with other muscles in shutting the jaws.

Several muscle groups (not shown) act on the TMJ to (i) elevate the mandible, closing the jaws; (ii) protrude the jaw; (iii) depress the chin; (iv) produce side-to-side movement of the jaw; (v) elevate the mandible, closing the jaws; and (vi) produce a grinding motion for cutting food.

C. The Neck

The neck (see FIG. 5) is the portion of the body joining the head to the shoulders and chest. The neck is a major conduit between the head, trunk, and limbs. Many important anatomic structures are crowded together in the neck, such as muscles, veins (e.g., the jugular veins), arteries (e.g., the carotid arteries), vertebrae (e.g., the seven cervical vertebrae and enclosed spinal cord), the pharynx, and part of the esophagus. A broad, thin plane of muscular fibers, called the platysma myoides or platisma, extends immediately beneath the superficial fascia of each side of the neck. Food and air entering the oral cavity must pass through the neck.

Also present in the neck is the hyoid bone, as FIG. 6 prominently shows. The hyoid bone lies in the anterior part of the neck at the level of the C3 vertebra in the angle between the mandible and the thyroid cartilage, which is the largest cartilage of the larynx.

1. The Hyoid Bone

Figure 5:
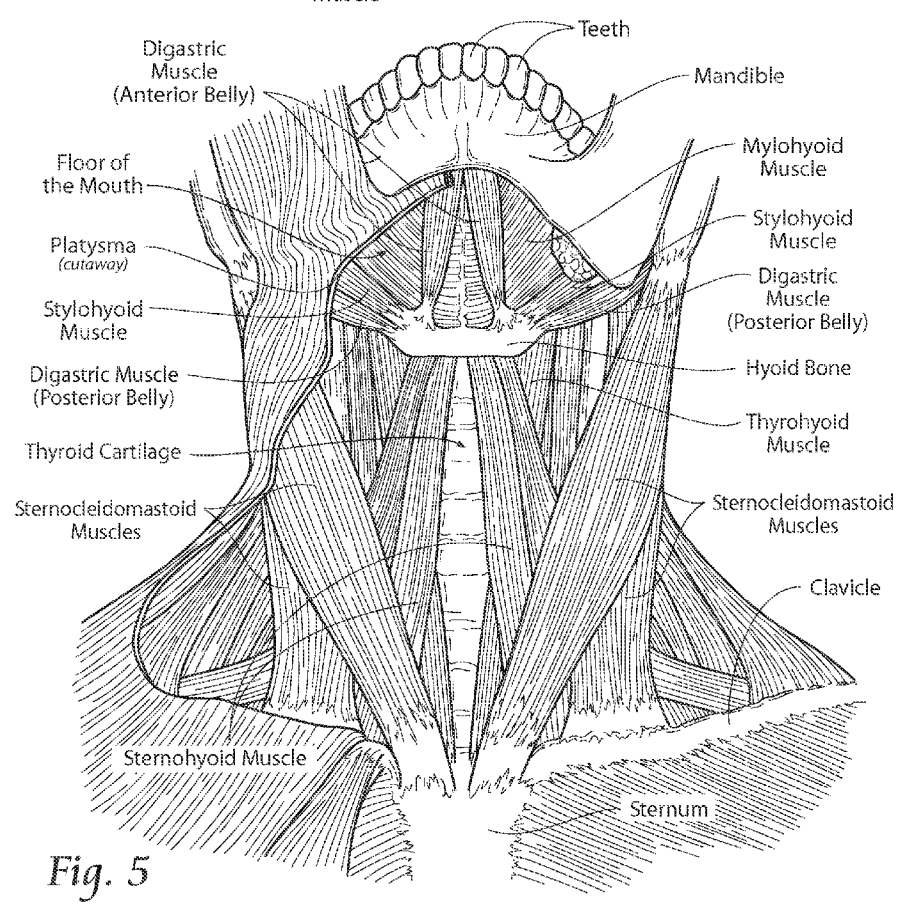
FIG. 5 is an anatomic anterior view of the major muscles of the neck, also showing the hyoid bone and the muscles connected to it.

A primary function of the hyoid bone is to serve as an anchoring structure for the tongue. As FIG. 6 shows, the hyoid bone is situated at the root of the tongue in the front of the neck and between the mandible and the thyroid cartridge. The hyoid bone has no articulation with other bones. It serves a purely anchoring function. The hyoid bone is suspended from the styloid processes of the temporal bones by the stylohyoid ligaments (as FIGS. 5 and 6 show, as as also shown in FIG. 3). The hyoid bone is firmly bound to the thyroid cartilage (as FIG. 5 shows in an anterior view). It serves as an anchoring point for muscles of the tongue and, thus, as a prop to the keep the tongue from blocking the airway, as will be described in greater detail later. As best shown in FIGS. 7 and 8, the hyoid consists of a body, a pair of larger horns (the greater cornua), and a pair of smaller horns (the lesser cornua). The hyoid bone is more or less in the shape of a U, with the body forming the central part, or base, of the letter. In the act of swallowing, the hyoid bone, tongue, and larynx all move upward rapidly.

The greater cornua are the limbs of the U. Their outer ends generally are overlapped by the large sternocleido-mastoid muscles (see FIG. 5), which run from the sternum and clavicle to the mastoid region at the base of the skull on each side of the head just below and behind the ear in humans. The lesser cornua are small projections from the places called the junctions of the body and the greater cornua.

2. Extrinsic Muscles of the Tongue Attached to the Hyoid

Certain extrinsic muscles of the tongue originate outside the tongue and attach to it. Extrinsic tongue muscles mainly alter the position of the tongue. The tongue also has intrinsic muscles, which serve to alter the shape of the tongue. However, the muscles of the tongue do not act in isolation. Some muscles perform multiple actions. Thus, extrinsic muscles can alter the shape of the tongue, as well.

Figure 4:
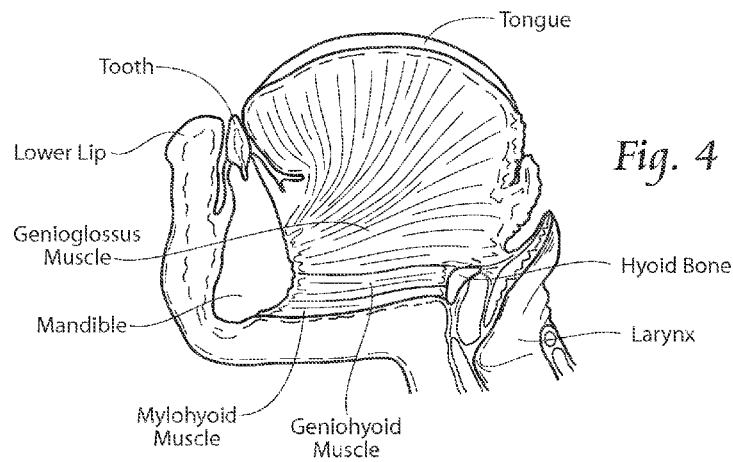
FIG. 4 is an anatomic side elevation view of the genioglossus and intrinsic muscles of the tongue.

Among the extrinsic muscles of the tongue that are attached to the hyoid bone are the genioglossus muscles (see FIGS. 3, 4, and 6). Fan-shaped muscles, they contribute to most of the bulk of the tongue. They arise by a short tendon from the superior part of the mental spine of the mandible, the region of the mandible that forms the prominence of the chin. They fan out as they enter the tongue inferiorly and their fibers attach to the outer dorsum of the tongue (i.e., the posterosuperior surface of the tongue). The most inferior fibers insert into the body of the hyoid bone and pull the root of the tongue anteriorly, for protruding or "sticking out" the tongue. The "root of the tongue" is defined as the inferior, relatively fixed part of the tongue that is attached to the hyoid bone and mandible. Acting bilaterally, the genioglossus muscles depress the central part of the tongue, creating a central groove or furrow. Acting unilaterially, the genioglossus will deviate (or "wag") the tongue toward the contralateral side.

Also among the extrinsic muscles of the tongue that are attached to the hyoid bone are the hyoglossus muscles (shown in FIGS. 3 and 6). They originate on each side from the whole length of the greater cornua, as well as from the body of the hyoid. They are inserted into the posterior half or more of the sides of the tongue. The hyoid bone anchors the muscles when they contract, to depress the tongue and to widen the oral cavity.

3. Other Muscles in the Neck That Are Attached to the Hyoid

In the anteriolateral part of the neck, the hyoid bone provides for attachments for other muscles that are not intrinsic or extrinsic muscles of the tongue. Among these are certain suprahyoid muscles superior (above or cranial) to the hyoid bone.

Suprahyoid muscles attached to the hyoid bone include the mylohyoid muscles (shown in FIGS. 3 and 4). The mylohyoid muscles originate from the mylohyoid line of the mandible (which lies along a lateral side of the mandible between the angle of the mandible and the front of the mandible, also called mental protuberance). The mylohyoid muscles form the mobile but stable floor of the mouth and a muscular sling interior to the tongue that serves as a diaphragm. These muscles support the tongue and elevate it and the hyoid bone when swallowing or protruding the tongue.

Suprahyoid muscles attached to the hyoid also include the two geniohyoid muscles (also shown in FIGS. 3 and 4). The two geniohyoid muscles originate close to the point at which the two halves of the mandible meet. The geniohyoid muscles are superior to the mylohyoid muscles, where they reinforce the floor of the mouth. The fibres of the muscles extend downward and backward, close to the central line, to be inserted into the body of the hyoid bone. Contraction of the muscles pulls the hyoid bone upward and forward, to shorten the floor of the mouth and widen the pharynx.

Suprahyoid muscles attached to the hyoid also include the two digastric muscles ((see FIGS. 5 and 7), which also originate from the diagastric fossa of the mandible and the mastoid notch of temporal bone. The diagratric muscles descend toward the hyoid bone and are joined by an intermediate tendon. A fibrous sling derived from the deep cervical fascia allows each muscle to slide anteriorly and posteriorly as it connects this tendon to the body and greater cornua of the hyoid bone. The digastric muscles depress the mandible, while also raising and steadying the hyoid bone during swallowing and speaking.

Inserting into the middle part of the lower border of the hyoid bone are the sternohyoids (shown in FIGS. 5 and 7), which are long muscles arising from the breastbone and collarbone and running upward and toward each other in the neck. Other muscles attached to the hyoid bone are the thyrohyoid (shown in FIG. 5), arising from the thyroid cartilage of the larynx (which depresses the hyoid bone and elevates the larynx); the omohyoid (not shown), which originates from the upper margin of the shoulder blade and the suprascapular ligament (which depresses, retracts, and steadies the hyoid bone); and the stylohyoid (shown in FIGS. 4, 5, and 7), arising from the styloid process of temporal bone (which elevate and retracts the hyoid bone, thereby elongating the floor of the mouth).

4. Swallowing

The position of the hyoid bone with relation to the muscles attached to it has been likened to that of a ship steadied as it rides when anchored "fore and aft." Through the muscle attachments, the hyoid plays an important role in mastication, in swallowing, and in voice production.

For example, at the beginning of a swallowing motion, the geniohyoid and mylohyoid muscles elevate the hyoid bone and the floor of the mouth simultaneously. These muscles are assisted by the stylohyoid and digastric muscles. The tongue is pressed upward against the palate and the food is forced backwards.

II. Collapse of the Airway

As shown in FIG. 9, the airway is the path that air follows to get into and out of the lungs. The mouth and nose are the normal entry and exit ports. Entering air passes through the mouth, between the tongue and palate, to the back of the throat (pharynx), and continues through the voice box (larynx), down the trachea, and finally out the branching tubes in the lungs, known as bronchi (not shown). A normal breath of air passes through the oral or nasal passages, behind the palate, uvula, and root of the tongue, then into and through the pharyngeal airway, and between the vocal cords of the larynx into the lungs.

As shown in FIG. 9, under normal breathing conditions, in a healthy person who is awake, active, and upright, the force of gravity naturally draws the tongue, tissue structures in the floor of the mouth, and tissue in the neck in a caudal direction, i.e., toward the feet. The force of gravity provides, when a person is upright, a natural bias to the tongue, tissue structures in the floor of the mouth, and tissue in the neck toward the feet mostly out of the path that air follows in the oral cavity. The caudal gravitational bias provided when a person is upright maintains a desired tongue orientation out of the airway in the oral cavity, thereby providing beneficial spacing between tongue and the palate, as well as maintains a desired orientation of neck tissue out of the airway.

Further, when a healthy person is awake and active, the coordinated activity of muscles of the tongue, floor of the mouth, neck, upper part of the pharyngeal airway or throat, and/or mandible serves also to keep the airway open to allow air to flow through the nasal passages, behind the palate, uvula, and tongue base, through the airway, and between the vocal cords and into the lungs.

However, during sleep (see FIG. 10), the tongue, tissue structures in the floor of the mouth, and/or tissue in the neck can shift or collapse as they lose tension and as the sleeping body position alters the influence of gravity, into the airway. The undesired shifting or collapse of the tongue, tissue structures in the floor of the mouth, and/or tissue in the neck into the airway during sleep can be attributed to one or a combination of causes.

One cause is gravity. During sleep, a person is no longer upright, but is instead lying down in a prone, supine, or side position. The pull of gravity on tissue of a person lying down is not toward the feet. Instead, the force of gravity on a person lying down serves to shift the orientation of the tongue, and/or tissue structures in the floor of the mouth, and/or tissue in the neck inward and/or toward the airway.

Another cause is that, during sleep, many of the muscles in or affecting the tongue, neck, upper part of the pharyngeal airway, and/or mandible can undergo phasic changes in their electrical activity synchronous with respiration, leading to relaxation of these muscles. During one particular stage of sleep, the stage of rapid eye movement (REM), the muscles may completely relax. The muscles also completely relax during exhalation, prior to the beginning of inhalation.

Also, during sleep, muscles affecting the mandible can relax. The mandible drops (as FIG. 11 shows), and the mouth opens. During sleep, the head may also rotate inferiorly in flexion, or translation may occur within the TMJ to cause a posterior sliding of the mandible. The shift in mandible and/or head orientation during sleep leads to a shortening of the native anterior-to-posterior distance between the mandible and hyoid within the floor of the mouth.

The native anterior-to-posterior distance between the mandible and hyoid is shown as D1 in FIG. 9. A shortened anterior-to-posterior distance between the mandible and the hyoid, caused by a shift in the mandible and/or head orientation during sleep is shown as D2 in FIG. 11. As a comparison between D1 (FIG. 9) and D2 (FIG. 11 shows, D2 is less than D1.

As the anterior-to-posterior distance is reduced by mandible and head orientation, the tongue and tissue structures in the floor of the mouth, which occupy this space, are shifted inward and toward the airway.

Also, during sleep, as a result of the diminution or absence of native muscle activity, the position of the root of the tongue can shift in a posterior direction, toward and into the airway. Further, during sleep, the diminution or absence of native muscle activity in the neck can lead to the collapse of tissue in the neck toward and into the airway.

AS FIG. 10 shows, for many individuals, the airway remains open enough, despite the sleep-related effects of gravity on tissue, and/or changes in mandible and head orientation, and/or relaxation of one or more of muscles affecting the tongue, floor of the mouth, or neck, to permit the flow of air during sleep.

As shown in FIG. 11, other individuals, however, are, for various reasons, more prone to experiencing more chronic or sever breathing restrictions as the airway narrows. For such individuals, narrowing of the airway during sleep can be accompanied by a sleep disordered breathing condition, such as habitual snoring or obstructive sleep apnea (OSA). Such individuals may even experience a cessation of breathing, which leads to a marked fall in blood oxygen levels, terminating in arousal, making it impossible to achieve deep, restorative sleep.

For example, in some individuals, due to hereditary, disease, or obesity, tissue structures within the mouth, such as the soft palate, uvula, and/or tongue may be enlarged or have lost compliance, or the walls of the pharyngeal airway itself may have narrowed due to tissue enlargement or lack of tissue compliance in regions of the neck. For such individuals, relaxation of muscles of the mandible, tongue, neck, and/or upper part of the pharyngeal airway, can lead to tissue in the floor of the mouth, and/or at the root of the tongue, and/or along the neck falling into the oral, nasal, or pharyngeal regions of the airway, thereby obstructing or completely closing the airway for breathing. In some individuals, this result is exacerbated if the person is resting in a supine position, flat on their back. Loud snoring and labored breathing can occur. When complete blockage of the airway occurs (as FIG. 11 shows), air cannot reach the lungs. Breathing stops, until the shortage of oxygen in the blood stream awakes the person, or causes the level of sleep to become more shallow. If these episodes repeatedly occur during sleep, the condition is called obstructive sleep apnea. Partial blockage of the airway can also lead to a drop in the blood oxygen level (called oxygen desaturation) and a condition called hypopnea. Hypopnea can also lead to obstructive sleep apnea.

III. Apparatus and Methods for Constraining the Mandible and/or Head

Figure 12A:
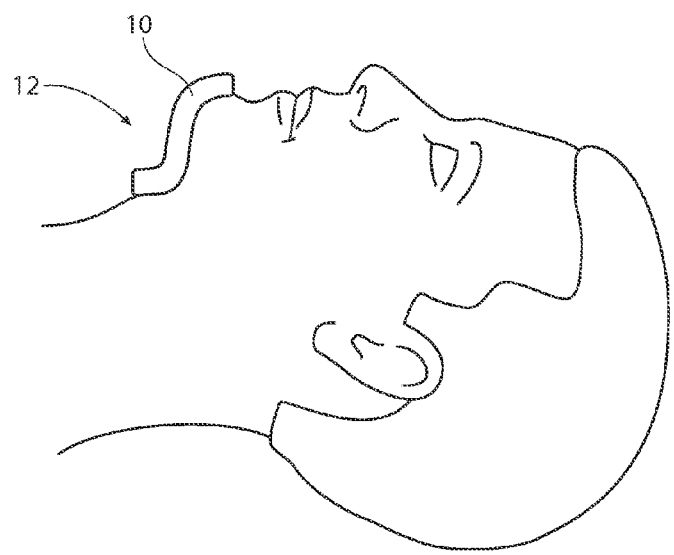
FIG. 12A is a side elevation view of the head of an individual in a supine sleep position, showing in basic terms an apparatus worn by the individual that mechanically supports the mandible and/or head in a desired orientation, to affirmatively resists movement of the mandible and/or head out of the desired orientation.

FIG. 12A shows in basic terms an apparatus 10 for constraining a mandible and/or head. In use, the apparatus 10 helps an individual with a sleep disordered breathing condition, such as habitual snoring or obstructive sleep apnea (OSA), to achieve deep, restorative sleep.

As will be described, the apparatus 10 functions without use of external positive pressure ventilation techniques, like CPAP and its attendant problem, previously described. However, if desired, the apparatus 10 can be used in combination with external positive pressure ventilation techniques, like CPAP. The apparatus 10 can also be used in combination with intraoral oral appliances used to position the tongue and/or jaw during sleep, or with the Pillar® Procedure (Restore Medical Inc.), or tissue removal or other surgical intervention techniques, such as maxillomandibular advancement (MA) or uvulopalatopharyngeoplasty (UPPP). The additive effects of the apparatus 10 can serve to moderate the required nature and extent of these often highly invasive surgical procedures, thereby reducing the often long recover time and increasing patient appeal. When used in combination with CPAP, oral appliances, and surgical procedures, the presence of the apparatus 10 can increase the success rates of conventional treatments.

A. Overview

In basic term, as FIG. 12A shows, the apparatus 10 mechanically supports the mandible and/or head in a desired orientation, particularly when the individual is in a sleep position. The mechanical support that the apparatus 10 provides affirmatively resists movement of the mandible and/or head out of the desired orientation.

Figure 12B:
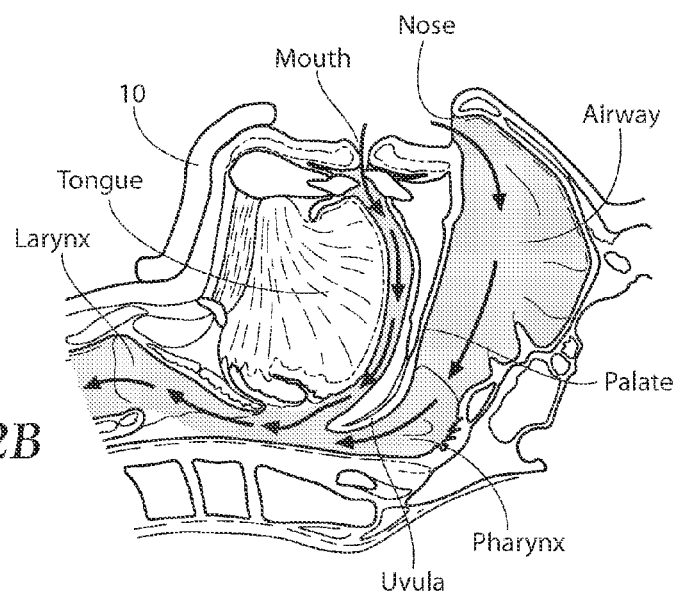
FIG. 12B is an anatomic side section view of the oral cavity of the individual shown in FIG. 11A, annotated to show the apparatus functioning to affirmatively resist movement of the mandible and/or head out of the desired orientation and thereby maintain an unobstructed airway.

A therapeutic result of the mechanical support that the apparatus 10 provides can include maintaining a desired anterior-to-posterior distance between the mandible and hyoid. In this arrangement, the desired anterior-to-posterior distance between the mandible and hyoid is selected to bias the tongue and tissue structures in the floor of the mouth toward an orientation that lies out of the airway, as FIG. 12B shows. The apparatus 10 thereby resists movement of the tongue and tissue structures in the floor of the mouth into orientations (as shown in FIG. 11) that lie toward and in the airway.

However, the mechanical support that the apparatus 10 provides to tissue need not include the maintenance of an anterior to posterior distance between the manidible and hyoid.

For example, another therapeutic result of the mechanical support that the apparatus 10 provides can include the application of tension to the muscles along the pharyngeal airway. The tension applied by the apparatus 10 creates a more rigid airway. The tension applied by the apparatus 10 conditions muscle structures in the neck to resist collapse of tissue in the neck toward and into the pharyngeal airway, as FIG. 12B shows.

The apparatus 10 can impose one or more different conditions to constrain the mandible and/or head. The different conditions complement one another in resisting movement of the tongue and tissue structures in the floor of the mouth into orientations that lie toward and in the airway. Compare the orientation of tissue shown in FIG. 11, in which the tongue and tissue structures have collapsed into the airway, with the orientation of tissue FIG. 12B, in which the presence of the apparatus 10 serves to resist movement of the tongue and tissue structures in the floor of the mouth into orientations that lie toward and in the airway. In a representative embodiment, the imposition of four conditions, singly or in combination, are disclosed.

1. First Constraint Condition (Maintain Closure of the Mouth)

Figure 13A:
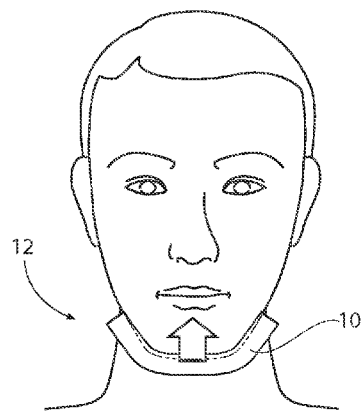
FIGS. 13A, 13B, 13C, and 13D are perspective views of an individual wearing an apparatus like that shown in FIG. 12A, showing different types of constraining forces that the apparatus can provide to a mandible and/or head.

As shown in FIG. 13A, the apparatus 10 may impose a first constraint condition 12, to affirmatively resist an articulation of the mandible that leads to opening the mouth. The first constraint condition 12 keeps the jaw (and thus the mouth) closed. This constraint condition 12 can establish and maintain a desired anterior-to-posterior distance between the mandible and hyoid.

2. Second Constraint Condition (Limit Inferior Rotation of the Head)

Figure 13B:
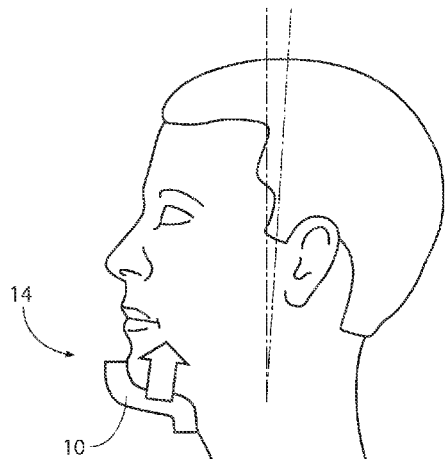

As FIG. 13B shows, the apparatus 10 may impose a second constraint condition 14, to affirmatively limit inferior rotation (nodding) of the head. The second constraint condition 14 lifts the chin and, therefore, the head. This constraint condition 14 can also establish and maintain a desired anterior-to-posterior distance between the mandible and hyoid. A lifting force on the chin and mandible can also serve to stretch and maintain an opened airway.

3. Third Constraint Condition (Provide an Anterior Position to the Jaw)

Figure 13C:
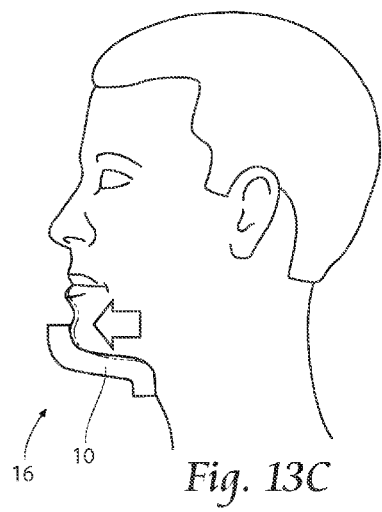

As FIG. 13C shows, the apparatus 10 may also impose a third constraint condition 16, to affirmatively resist inferior translational movement of the mandible within the TMJ. The third constraint condition 16 may move the mandible slightly forward into a protruding, under-bite position, which may not be the native position of the person's jaw. This constraint condition 16 can increase the anterior-to-posterior distance between the mandible and hyoid. Alternatively, the third constraint condition 16 may at least maintain a desired anterior-to-posterior position, without moving the mandible forward.

4. Fourth Constraint Condition (Twist/Elevate the Head)

Figure 13D:
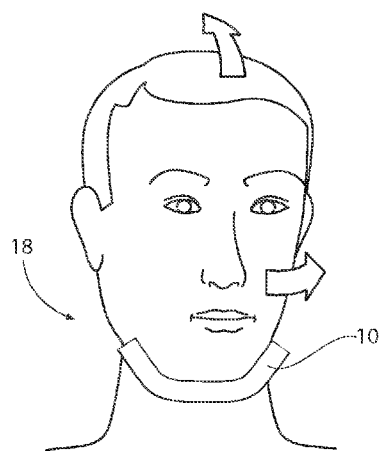

As FIG. 13D shows, the apparatus may impose a fourth constraint condition 18, to maintain a desired twist as well as elevation to the head. The fourth constraint condition 18 applies a side force or torque to the mandible to cause a slight twisting of the head to one side. This constraint condition 18 applies tension to muscles structures along the pharyngeal airway to create a more rigid airway.

B. Representative Embodiments

As will be described in greater detail later, the size, configuration, and mechanical properties of the apparatus 10 are selected to impose one or more of the above-described constraint conditions 12, 14, 16, 18 to the mandible and/or head particularly during sleep, in the absence of or diminution of native muscle activity and/or during sleep postures that can cause airway obstruction. The size, configuration, and mechanical properties of the apparatus 10 to achieve these objectives during sleep are counterbalanced with sufficient compliance and flexibility to reasonably accommodate normal activities willed by volitional muscle activity, to allow the jaw to be intentionally opened or the head to be intentionally turned. As will be described later, the particular size, configuration, and mechanical properties of the apparatus 10 can be tailored or customized to the individual patient.

1. Mandible/Head Support (i) Chin Support with Neck Piece

Figure 14A:
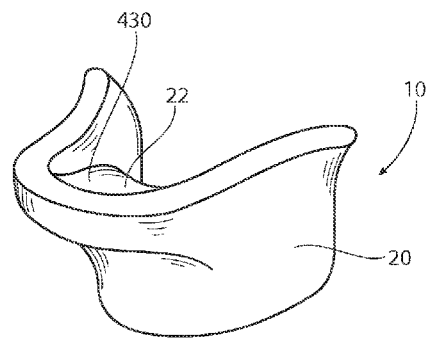
FIGS. 14A, 14B, and 14C are perspective views of a representative embodiment of an apparatus like that shown in FIG. 12A, sized and configured as a structure that is preformed to an anatomic shape that can be comfortably inserted onto the front of the neck (in the region of the larynx) just under the chin and likewise removed from the neck when use is not required.
Figure 14B:
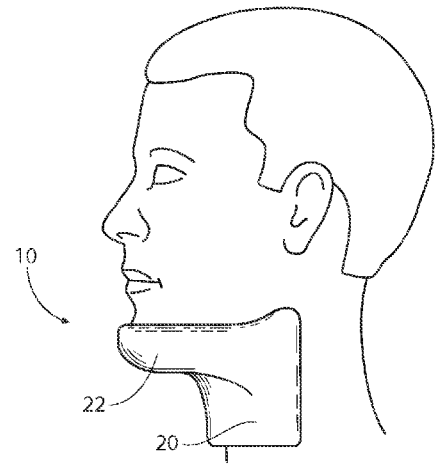
Figure 14C:
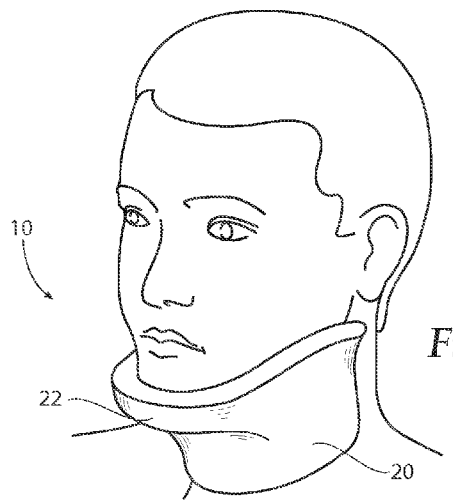

FIGS. 14A, 14B, and 14C show a representative basic embodiment of an apparatus 10 for constraining a mandible and/or head. The apparatus 10 comprises a neck piece 20 or holdfast and a chin support 22 carried by the neck piece 20. The chin support 22 preferably includes a concave pocket region 430 under the chin, which provides clearance between the chin support 22 and tissue in, on, or near the floor of the mouth. The clearance provided by the pocket region 430 assures that the chin support 22 does not, in use, inadvertently compress muscles or tissue in, on, or near the floor of the mouth. Compression of muscles or tissue in, on, or near the floor of the mouth by a chin support structure can interfere with the native anchoring function that the floor of the mouth provides to the mandible, hyoid bone, and tongue, which serves as a trampoline to stabilize the mandible, hyoid bone, and tongue while accommodating relative movement among them.

The neck piece 20 can be variously configured. In the embodiment shown in FIGS. 13A, 13B, and 13C, the neck piece 20 comprises a structure that is preformed to an anatomic shape sized and configured to be comfortably inserted onto the front of the neck (in the region of the larynx) just under the chin. The structure can be likewise removed from the neck when use is not required.

In this arrangement, the chin support 22 can comprise an integrally formed component, forming a unitary, pre-formed device. The device can be molded or formed from, e.g., from an elastic or semi-elastic polymer material. The pre-formed device can be shaped, sized, and contoured based upon the particular anatomy of the individual who will wear the device. However, the device can also be shaped, sized, and contoured based more upon a range of generic models of a human chin and neck.

The chin support 22 can comprise a structure made of a fabric material and be treated as a single or limited use, disposable item. The chin support 22 can be affixed to the front of the neck with a releasable adhesive, like a band-aid.

Figure 15A:
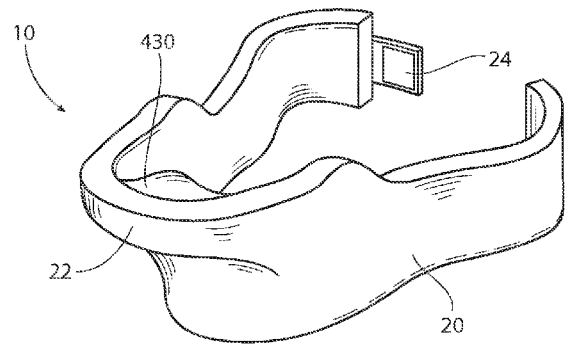
FIGS. 15A, 15B, and 15C are perspective views of a representative embodiment of an apparatus like that shown in FIG. 12A, sized and configured as a full collar structure that is worn about the entire neck at the level of the larynx and including releasable fasteners so that an individual can adjust the fit and form of the collar around their neck.
Figure 15B:
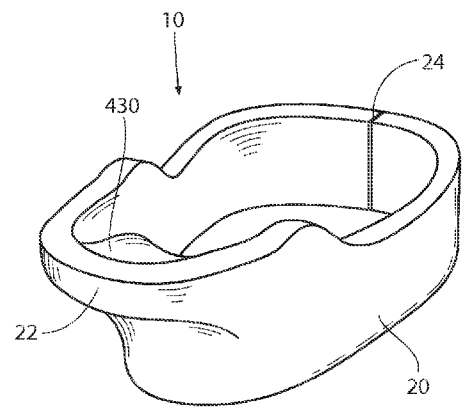
Figure 15C:
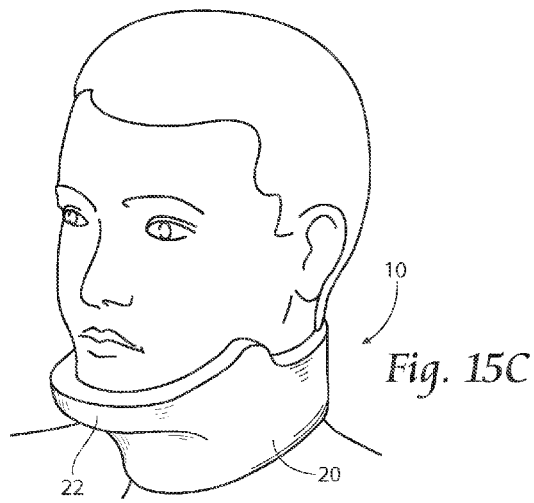

A somewhat different embodiment is shown in FIGS. 15A, 15B, and 15C. In this embodiment, the neck piece 20 comprises a full collar structure that is sized and configured to be worn about the entire neck at the level of the larynx. In this arrangement, the collar desirably includes releasable fasteners 24, e.g., such as snaps, magnets, buckles, straps, VELCRO® fabric, and the like, so that an individual can adjust the fit and form of the collar around their neck. In this arrangement, the collar can be made of a padded fabric.

In either embodiment, the chin support 22 desirably extends from the neck piece 20 in an anterior and slightly superior orientation. When the neck piece 20 is worn on the neck, the chin support 22 is sized and configured to fit comfortable beneath the chin when the mouth is closed. As before stated, the chin support 22 preferably includes a concave pocket region 430 under the chin, which provides clearance between the chin support 22 and tissue in, on, or near the floor of the mouth to avoid interference with the native anchoring function that the floor of the mouth provides to the mandible, hyoid bone, and tongue.

In either embodiment, the neck piece 20 and chin support 22 are sized and configured to be easily fitted on the neck when the features of the apparatus are desired (i.e., at night, during sleep). The fit and form of the neck piece 20 and chin support 22 permit easy removal of the neck piece 20 and chin support 22 from the body when the features of the apparatus 10 are not desired (i.e., during daytime hours when the individual is awake and active).

The mechanical properties of the materials for the neck piece 20 and chin support 22, as well as the attachment and orientation of the chin support 22 to the neck piece 20, are selected to provide enough mechanical resistances to prevent an unintended articulation due to a tilting of the head, or a dropping open of the mandible away from the upper jaw, particularly when there is an absence or diminution of native muscle activity to keep the head from tilting or keep the mouth close, as could occur during sleep.

Still, the mechanical properties of the materials for the chin support 22 and neck piece 20 are counterbalanced with sufficient flexibility and yield to accommodate a purposeful opening of the mouth as a result of volitional muscle activity. Desirably, the materials comprise soft, supple, breathable fabric for comfort.

As shown in FIGS. 14C and 15C, the apparatus 10 forms a yieldable buttress for the mandible in the closed position. The apparatus 10 can thereby serve to maintain a desired anterior-posterior distance between the mandible and hyoid by imposing the first constraint condition 12, which is keeping the mouth closed. The apparatus 10 also imposes the second constraint condition 14, which affirmatively limits inferior rotation of the head.

The size and configuration of the chin support 22 and neck piece 20 are selected and contoured to limit direct pressure on soft tissue under the chin and in the floor of the mouth. Limiting direct pressure on these tissue regions prevents an unintended inward movement of these tissue regions toward the airway and a resultant narrowing of the airway.

(ii) Pressure-Sensitive Adhesive

Figure 16A:
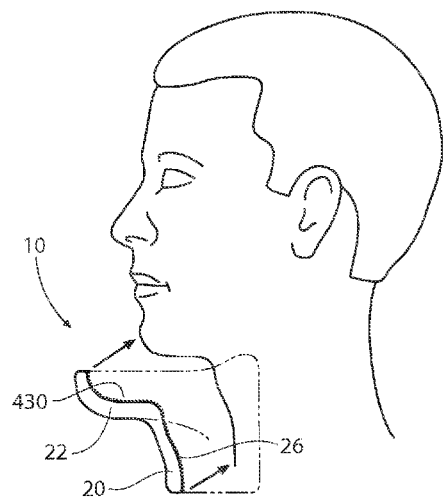
FIGS. 16A and 16B are side elevation views of a representative embodiment of an apparatus like that shown in FIG. 12A, including a pressure-sensitive medical grade adhesive gel or material applied to the inside of the apparatus to maintain intimate contact between skin and the apparatus during periods of use.
Figure 16B:
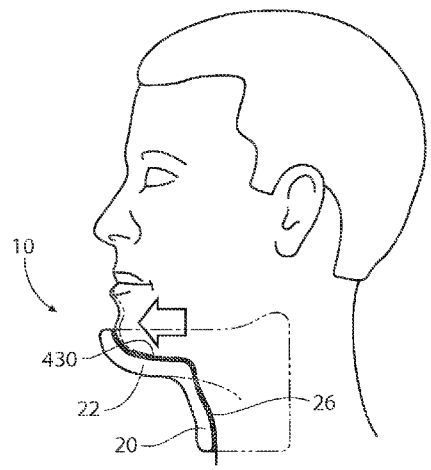

As shown in FIGS. 16A and 16B, the apparatus 10 can include a pressure-sensitive medical grade adhesive gel or material 26. The adhesive material 26 is applied to the inside of the neck piece 20 and/or chin support 22. The adhesive material 26 maintains intimate contact between skin and the neck piece 20 and/or chin support 22 during periods of use. As before stated the apparatus 10 can comprise a fabric material and be treated as a single or limited use, disposable item. The adhesive material 26 can comprise conventional pressure-sensitive compositions used for adhesion to the skin, particularly in the field of colostomy care. Examples of such adhesive materials 26 include Hollister Colostomy Adhesive (Hollister Inc, Libertyville, Ill.), Nu-Hope™ Adhesive (Bruce Medical), or Permatype™ Surgical Adhesive (edipMed.com).

Representative pressure sensitive adhesive materials 26 comprise a self-adhesive elastomeric matrix, in which water-absorbing, swelling particles, called hydrocolloids, are dispersed.

The adherence of the adhesive material 26 to tissue stabilizes the orientation of the mandible as dictated by the chin support 22. The inclusion of adhesive material 26 with the assembly can enhance the achievement of at least one additional desirable constraint condition, and thereby enhance the overall function of the apparatus.

For example, the application of an adhesive material 26 to the chin support 22 makes it possible to impose the third constraint condition 16, which is to provide and maintain an anterior position to the jaw (see FIG. 16B). The adhesive material 26 on the chin support 22 grabs chin tissue. A desired anterior orientation of the mandible can be established and then maintained by adhesive force by the chin support 22. The adhesive force can maintain the mandible in a desired slightly anterior (protruding) orientation and thereby affirmatively resist posterior translational movement of the mandible within the TMJ. However, it should be appreciated that the third constraint condition 16 can be achieved with the form and fit of the apparatus, without the use of an adhesive material 26. As before stated, the chin support 22 preferably includes a concave pocket region 430 under the chin, which normally provides clearance between the chin support 22 and tissue in, on, or near the floor of the mouth. Tissue in, on, or near the floor of the mouth can be drawn into this pocket region 430 without compressing the tissue, to thereby avoid, during use, interference with the native anchoring function that the floor of the mouth provides to the mandible, hyoid bone, and tongue.

(iii) Variable Constraint of the Mandible and/or Head

Figure 17A:
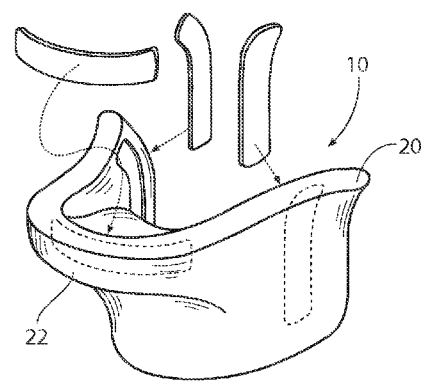
FIGS. 17A and 17B are perspective views of a representative embodiment of an apparatus like that shown in FIG. 12A, in which the magnitude and/or direction of the constraining force can be varied, altered, or titrated by use of insertable stays.
Figure 17B:
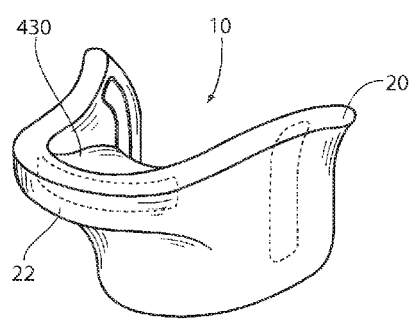

FIGS. 17A and 17B show a representative, more advanced embodiment of an apparatus 10 for constraining a mandible and/or head. In this embodiment, the magnitude and/or direction of the constraining force can be varied, altered, or titrated.

As shown in FIGS. 17A and 17B, the neck piece 20 and/or the chin support 22 includes pockets 28. The pockets 28 are sized and configured to receive reinforcing elements or stays 30. As shown, the stays 30 can comprise strips of plastic material, but other cross-sectional configurations, linear or curvilinear, and material choices are possible. Each stay 30 possesses one or more quantifiable physical properties, which can be expressed in terms, e.g., length, thickness, elasticity, tensile strength, flexure (Standard Gurley Units), compressibility, spring constant, torque, shape, etc. By the purposeful selection and insertion of stays 30, individually or in groups of two or more, the physical properties of the neck piece 20 and/or chin support 22, which affect its ability to constrain the mandible and/or head in a desired way, can be incremental adjusted. Over time, the physical properties of the neck piece 20 and/or chin support 22 can be titrated against the individual's sleep performance, to optimize for that individual the physical properties of the neck piece 20 and/or chin support 22 most conducive to deep, restorative sleep.

Figure 18A:
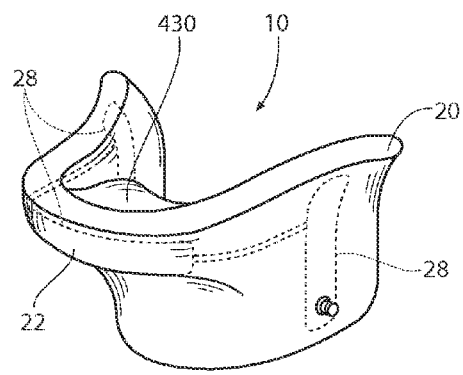
FIGS. 18A and 18B are perspective views of a representative embodiment of an apparatus like that shown in FIG. 12A, in which the magnitude and/or direction of the constraining force can be varied, altered, or titrated by use of a pressurized fluid or gas.
Figure 18B:
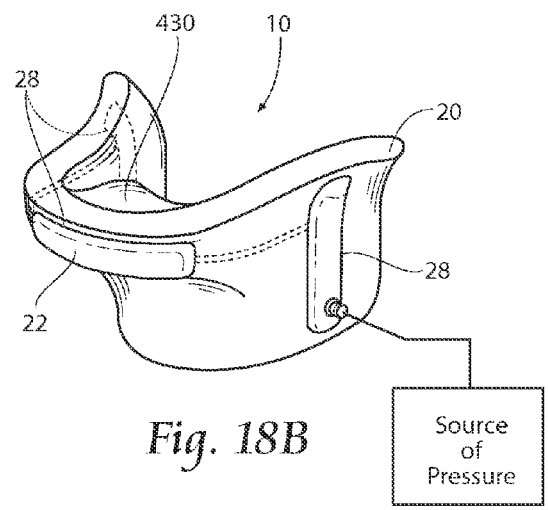

Alternatively, as shown in FIGS. 18A and 18B, the pockets 28 can comprise inflatable chambers, to receive gas or fluid pressure from an external source 32, or to otherwise be enlarged or expanded. By the purposeful expansion of the inflatable chambers 28, e.g., by introduction of gas or fluid pressure, individually or in groups of two or more inflatable chambers, the physical properties of the neck piece 20 and/or chin support 22, which affect its ability to constrain the mandible and/head in a desired way, can be incremental adjusted. Over time, the physical properties of the neck piece 20 and/or chin support 22 can be titrated against the individual's sleep performance, to optimize for that individual the physical properties of the neck piece 20 and/or chin support 22 most conducive to deep, restorative sleep.

In the preceding embodiments, and as before stated, it is desirable that the chin support 22 accommodate displacement of tissue in, on, or near the floor of the mouth without compressing the tissue, to thereby avoid, during use, interference with the native anchoring function that the floor of the mouth provides to the mandible, hyoid bone, and tongue.

(iv) Dynamic Constraint of the Mandible and/or Head

Figure 19A:
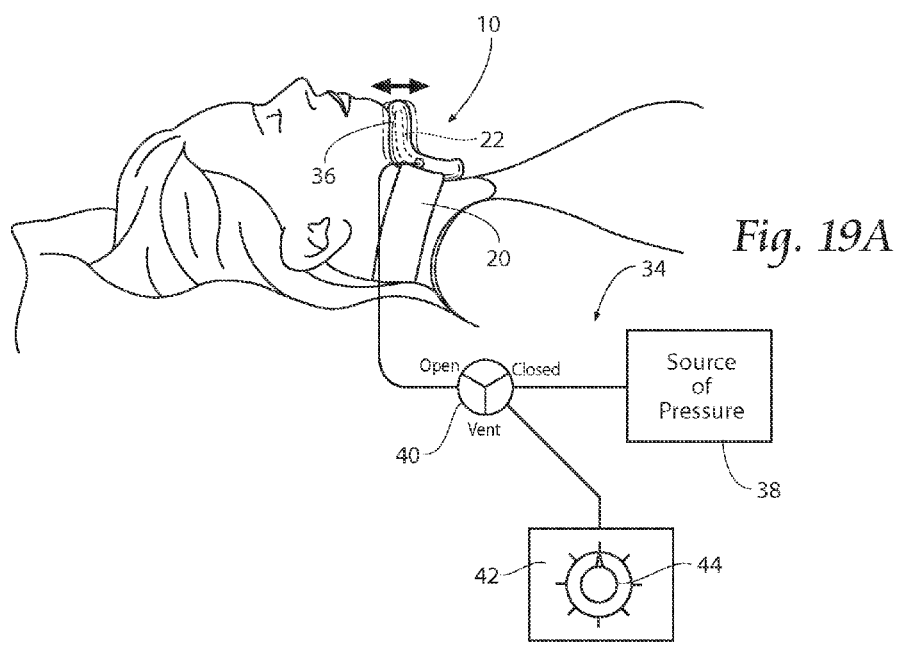
FIG. 19A is a side elevation view of a representative embodiment of an apparatus like that shown in FIG. 12A, including an actuator making it possible to adjust the constraining forces on an individual's mandible and head.

The magnitude and/or direction of the constraining force can be also varied in a dynamic manner. As shown in FIG. 19A, an apparatus 10 for constraining a mandible and/or head can include an actuator 34 coupled to the chin support 22, making it possible to articulate the chin support 22 by operation of the actuator 34. Operating the actuator 34, the chin support 22 can be incrementally articulated toward the chin, to exert a progressive lifting force and/or rotation force on an individual's mandible and head. Conversely, the actuator 34 can articulate the chin support 22 away from the chin, to moderate the lifting force. As previously mentioned, a lifting force and/or rotational force on the chin and mandible can also serve to stretch and maintain an opened airway.

The actuator 34 for articulating the chin support 22 can vary and can be controlled in various ways. For example, electromechanical lifters or shape activated materials may be incorporated into the chin support 22.

In an illustrated embodiment, the chin support 22 comprises inflatable chambers 36 that are expanded in response to the application of fluid (e.g., gas or air) pressure from a source 38 through a solenoid control valve 40. The solenoid control valve 40 includes an open condition, allowing conveyance of fluid pressure from the source to the chin support chambers 36; a closed condition, preventing conveyance of fluid pressure from the source to the chin support chamber 36; and a vent condition, venting fluid pressure from the chin support chamber 36.

The actuator 34 normally maintains the control valve 40 in the closed condition. The actuator 34 operates to open the valve 40, to expand the chin support chambers 36 under the individual's jaw. Progressive expansion of the chin support chambers 36 incrementally lifts the individual's jaw and/or and/or provides a rotational force and/or provides progressive resistance to mandible and/or head movement rotation.

The actuator 34 can be operated manually by the individual or by a healthcare assistant. The actuator 34 can include a manual control unit 42 with lift magnitude readings or settings. Using the manual control unit 42, the individual or healthcare assistant can select a desired magnitude of lift. Over time, the magnitude of lift can be titrated against the individual sleep performance, to optimize for that individual the magnitude of lift most conducive to deep, restorative sleep.

A dynamically controlled apparatus 10 for constraining a mandible and/or head can be integrated into an overall therapeutic system, which controls the actuator 34 in response to a sensed sleep condition, e.g., a physical sleep position and/or sleep posture of the individual, either with respect to the position of the torso of the individual, or the position of the head of the individual, or both; sleep sound or vibration architecture; blood pressure; the level of oxygen in the blood; heart rate; respiration rate; periodic cessation of breathing, and/or muscle strain, or other sensed physiologic or physical conditions, to adjust the magnitude of lift in real time in a manner most conducive to deep, restorative sleep.

Figure 19B:
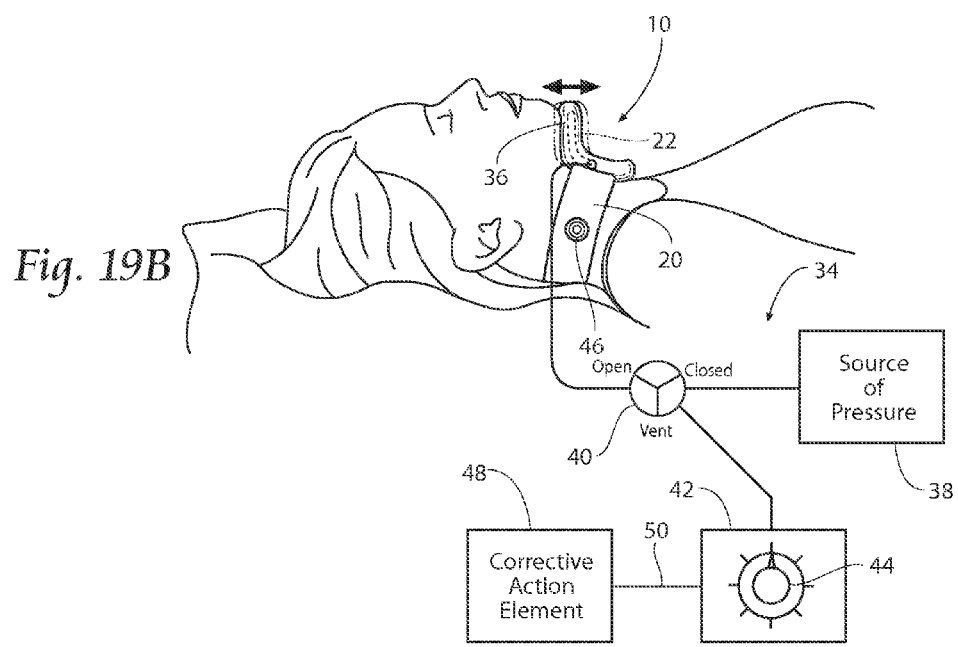
FIG. 19B is a side elevation view of the apparatus shown in FIG. 19A, integrated into an overall therapeutic system, which controls the actuator in response to a sensed sleep condition.

For example, in FIG. 19B, the neck piece 20 carries a sensor 46 for sensing a physical or physiological condition attending the individual's sleep. For example, in the illustrated embodiment, a sound sensitive element (e.g., one or more microphones) can be integrated into neck piece 20. The microphone 46 detects the sleep sound architecture of the individual. The sleep sound architecture is monitored and processed according to preprogrammed rules by a monitor element 48, which generates an alarm output 50 if the monitored sleep sound architecture does not conform to a "best" or desired benchmark.

The alarm output 50 is conveyed to the actuator 42. According to preprogrammed rules, the actuator 42 controls the control valve 40 to incrementally expand the chambers 36 and lift to exert a progressive lifting force and/or rotational force on the individual's jaw.

Progressive lifting the individual's jaw and/or incrementally turning the individual's head stretches the airway. This, in turn, leads to an opening of the airway and a change in the sleep sound architecture toward a benchmark condition. When the benchmark condition returns, the actuator 42 vents fluid pressure from the chin support chamber and returns the valve 134 to the closed condition.

Figure 20A:
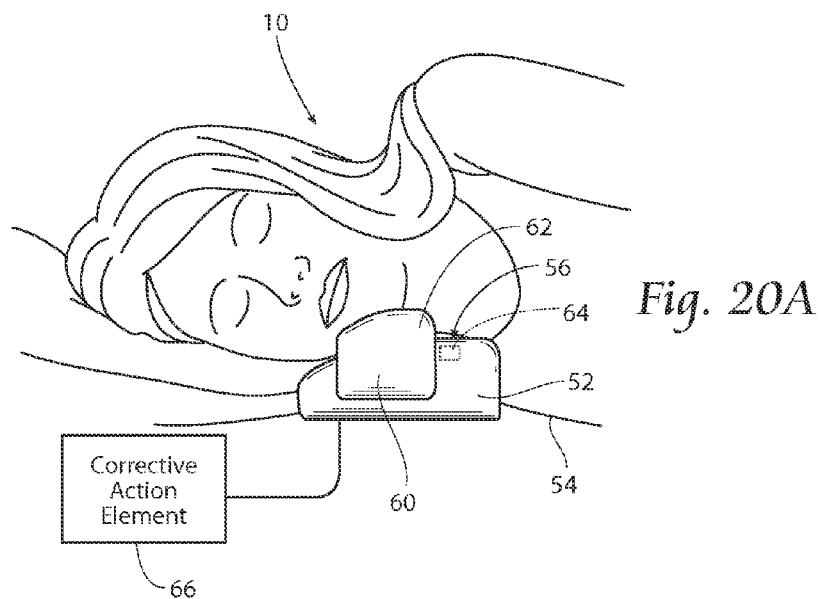
FIGS. 20A and 20B are, respectively, a side elevation view and top view of a representative embodiment of an apparatus like that shown in FIG. 12A, including an actuator making it possible to adjust the constraining forces on an individual's mandible and head, and integrated into an overall therapeutic system, which controls the actuator in response to a sensed sleep condition.
Figure 20B:
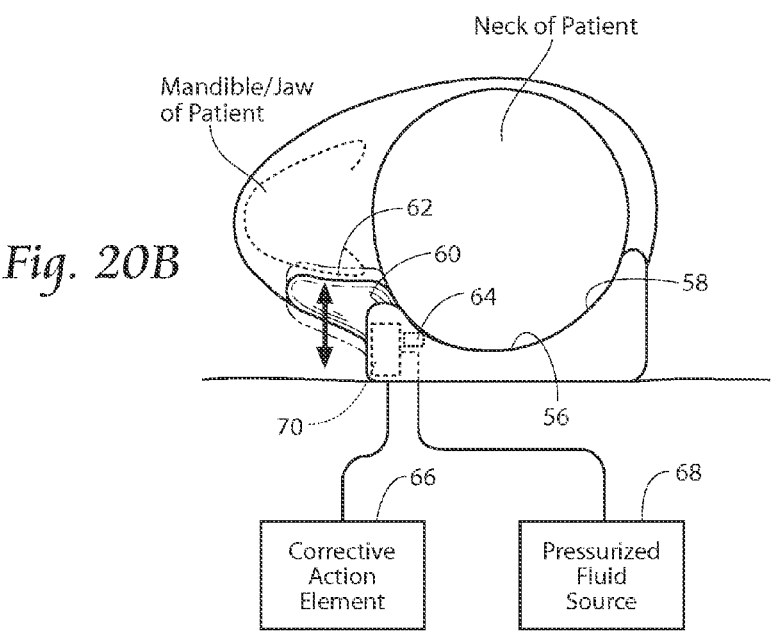

FIGS. 20A and 20B show another representative embodiment of a dynamically controlled apparatus 10 for constraining a mandible and/or head in response to sensed sleep conditions, as identified above.

In this embodiment, the apparatus 10 comprises a structure 52 sized and configured to support the neck of an individual while the individual rests in a side sleeping position on a sleeping surface 54 (as FIG. 20A shows). The structure 52 includes a neck support surface 56, on which the individual rests a side of their neck while their head rests on a pillow.

As FIG. 20B best shows, a posterior region 58 of the neck support surface 126 is contoured upward away from the sleep surface 54 to form a rest for the back of the neck, while the individual rests on a side of their neck in the remainder of the neck support surface 56. An anterior region 60 of the neck support surface 56 (the direction the individual's head faces) is also contoured upward, although not as much the posterior region, to form a forward rest for individual's chin. In this arrangement, the support surface takes the shape of a non-symmetric "U."

The structure includes a mandible positioning surface 62 located between the anterior and posterior regions of the neck support surface. The mandible positioning surface 62 is sized and configured to underlay the contour of the individual's jaw.

In this arrangement, a sensor 64 for sensing a physical or physiological condition attending the individual's sleep can be coupled to the apparatus. For example, in the illustrated embodiment, a sound sensitive element 64 (e.g., one or more microphones) can be integrated into the anterior region of the neck support surface 60 (as FIGS. 20A and 20B show). The microphone 64 detects the sleep sound architecture of the individual resting on their side in the neck support structure 56. The sleep sound architecture is monitored and processed according to preprogrammed rules, and an alarm output is generated if the monitored sleep sound architecture does not conform to the "best" or desired benchmark.

A corrective action element 66 controls the elevation of the mandible positioning surface 62 with respect to the neck support surface 56. Under the control of the corrective action element 66, the mandible positioning surface 62 can be incrementally lifted above the neck support surface to exert a progressive lifting force and/or rotational force on the individual's jaw.

The lifting and/or rotation of the mandible positioning surface 62 can be controlled in various ways. For example, electromechanical lifters or stiffeners may be used. In the illustrated embodiment, the mandible positioning surface 62 is lifted in response to the application of fluid pressure from a source 68 through a solenoid control valve 70. The solenoid control valve 70 includes an open condition, allowing conveyance of fluid pressure from the source 68 into the mandible positioning surface 62; a closed condition, preventing conveyance of fluid pressure from the source 68 into the mandible positioning surface 62; and a vent condition, venting fluid pressure from the mandible positioning surface to placed it in a collapsed condition.

The corrective action element 66 normally maintains the control valve 134 in the closed condition. In response to a sensed undesirable sleep condition (i.e., the alarm condition), the corrective action element 66 progressively opens the valve 70, to progressive lift the mandible positioning surface under the individual's jaw. Progressive lifting the mandible positioning surface incrementally lifts the individual's jaw, incrementally turns the individual's head, and stretches the airway. This, in turn, leads to an opening of the airway and a change in the sleep sound architecture toward a benchmark condition. Alternatively, the benchmark condition can comprise another sensed sleep condition, e.g., a physical sleep-position and/or sleep posture of the individual, either with respect to the position of the torso of the individual, or the position of the head of the individual, or both; sleep sound or vibration architecture; blood pressure; the level of oxygen in the blood; heart rate; respiration rate; periodic cessation of breathing, and/or muscle strain, or other sensed physiologic or physical conditions. When the benchmark condition returns, the corrective action element 66 vents fluid pressure from mandible positioning surface 62 and returns the valve 70 to the closed condition.

As before stated, the lifting of the jaw and chin in the preceding embodiments preferable avoids compressing tissue in, on, or near the floor of the mouth to avoid, during use, interference with the native anchoring function that the floor of the mouth provides to the mandible, hyoid bone, and tongue.

(v) Anchored Load Bearing Structure

Figure 21A:
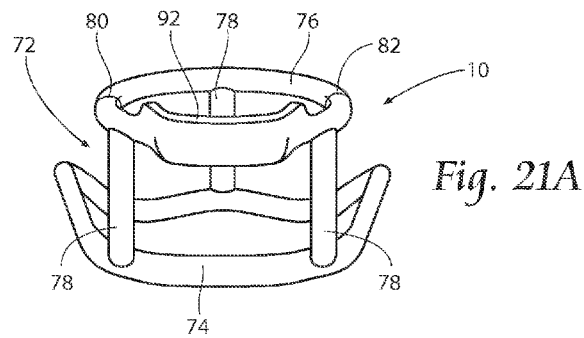
FIGS. 21A, 21B, and 21C are perspective views of a representative embodiment of an apparatus like that shown in FIG. 12A, comprising a load bearing structure that is sized and configured to be supported between rigid bony anchoring points between the shoulder and mandible.
Figure 21B:
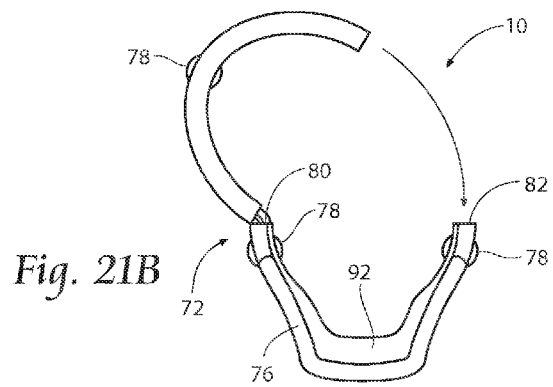
Figure 21C:
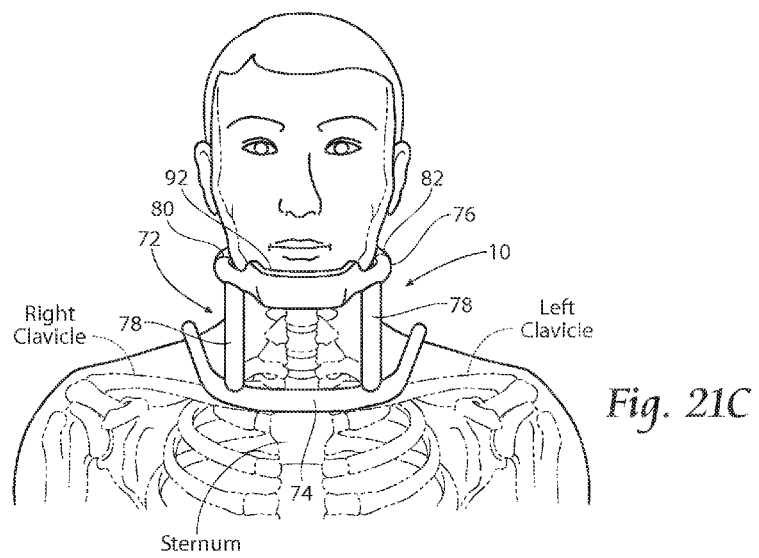
Figure 23A:
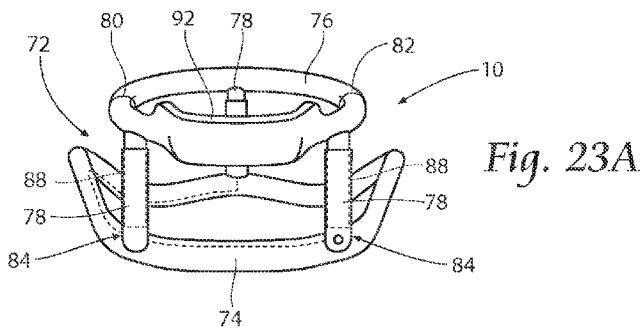
FIGS. 23A, 23B, and 23C are perspective views of a representative embodiment of an apparatus like that shown in FIGS. 22A, 22B, and 22C, in which the load bearing structure can be pneumatically adjusted in an axial direction.
Figure 23B:
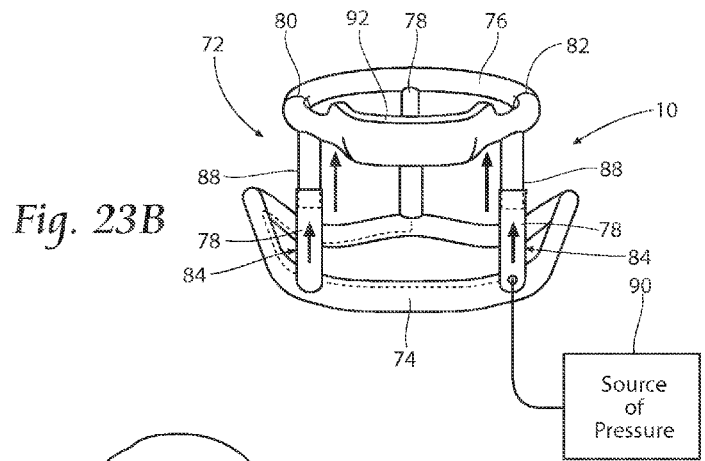
Figure 23C:
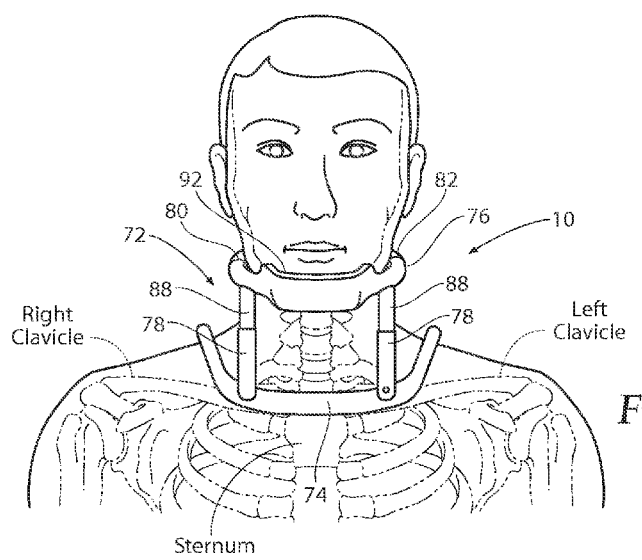

In the embodiment shown in FIGS. 21A, 21B, and 21C, the apparatus 10 includes a load bearing structure 72 that is sized and configured to be supported between rigid bony anchoring points between the shoulder and mandible (shown in FIG. 23C).

The load bearing structure 72 includes a caudal region 74. The caudal region 74 is sized and configured to engage the chest and back in contact, at least in part, with the left and right clavicle. The clavicle, also called the collar bone, is a long bone that makes up part of the shoulder girdle (pectoral girdle). The clavicle is also shown in FIG. 5 with respect to the tissue structures of the neck.

The load bearing structure 72 also includes a cranial region 76. The cranial region 76 is sized and configured to engage, at least in part, the bony perimeter of the mandible. For this purpose, the cranial region 76 can be contoured to include a channel 92 in which, during use, the bony periphery of the mandible rests. In this embodiment, the cranial region 76 is otherwise substantially free of contact with soft tissue under the chin.

The right and left clavicle and the bony perimeter of the mandible comprise, respectively, rigid caudal and cranial anchoring points for the load bearing structure 72. In the illustrated embodiment, the intermediate region of structure comprises load bearing trusses or spacers 78 coupled to the caudal and cranial regions 74 and 76. A hinge joint 80 allows the structure 72 to be opened (as FIG. 21A shows) and closed (as FIG. 21B shows) for insertion into position for use and removal after use. A releasable latch 82 locks the structure 72 in a closed position for use (as FIG. 21C shows). The releaseable latch 82 can comprise, e.g., releasable fasteners, e.g., such as snaps, magnets, buckles, straps, VELCRO® fabric, and the like, so that an individual can adjust the fit and form of the structure 72.

Inserted between bony, rigid anchor points of the clavicle and mandible when the mouth is closed, the load bearing structure 72 constrains the mandible and/or head in the manner previously described.

Axial Adjustment

In one embodiment (see FIGS. 22AA, 22B, and 22C, the load bearing trusses 78 in the intermediate region of the structure 72 include a mechanism 84 to permit adjustment of the axial distance between the caudal and cranial end regions 74 and 76. In the illustrated embodiment, load bearing trusses 78 comprise telescoping extension legs 78a and 78b. In this arrangement, the adjustment mechanism 84 comprises one or more screw clamps 86 at the telescopic junction of the legs 78a and 78b. Loosening the screw clamps 86 frees the legs for extension or retraction in an axial direction (as the arrows in FIG. 22B show), thereby increasing or reducing, respectively, the axial distance between the caudal and cranial regions 74 and 76. Tightening screw clamps 86 locks the legs 78a and 78b against extension or retraction, to holdfast a desired length as FIG. 22C shows.

The adjustment mechanism 84 makes it possible to adjust the axial length of the structure 72 according to an individual's anatomy and treatment objectives. In this way, the first and second constraint conditions 12 and 14, described above, that keep the mouth closed and that limit inferior rotation of the head can be optimized and/or titrated for a given individual.

The adjustment mechanism 84 also makes it possible to exert an enhanced lifting force on an individual's mandible and head to stretch and further open the airway.

Alternatively, as shown in FIGS. 23A, 23B, and 23C, the adjustment mechanism 84 can comprise telescoping, pneumatic chambers or cylinders 88 that enlarge in an axial direction in response to the introduction of gas or fluid pressure from an external source 90.

Rotational Bias

In another embodiment (see FIGS. 24A, 24B, and 24C), the load bearing structure 72 is sized and configured to provide a rotational offset to the cranial region 76 relative to the caudal region 74 about the axial axis. In the illustrated embodiment, the load bearing structure 72 is manufactured with a fixed, preset offset.

The rotational offset makes it possible to impose the fourth constraint condition 18, described above. The rotational offset establishes and maintains a desired twist or torque to the chin. Along with an axial length adjustment mechanism 84, the rotational offset also establishes and maintains a desired elevation of the chin. The rotational offset applies a side force or torque to the mandible to cause a twisting of the chin to one side. This constraint condition 14 applies tension to muscles structures along the pharyngeal airway to create a more rigid airway.

Mandible Adjustment

Figure 25A:
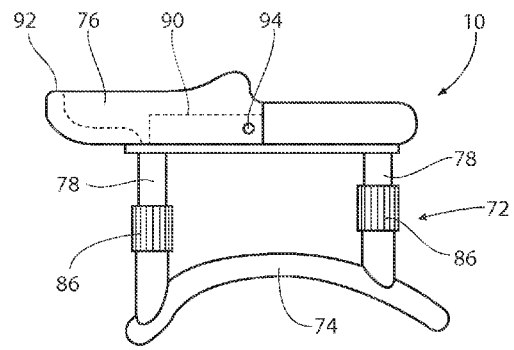
FIGS. 25A, 25B, and 25C are side elevation views of a representative embodiment of an apparatus like that shown in FIG. 12A, comprising a load bearing structure that is sized and configured to be supported between rigid bony anchoring points between the shoulder and mandible, and which can adjustably constrain the jaw in an anterior position.
Figure 25B:
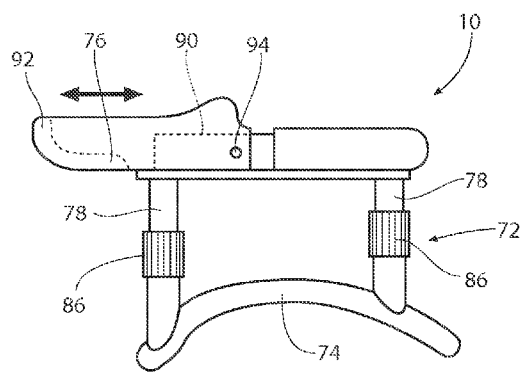
Figure 25C:
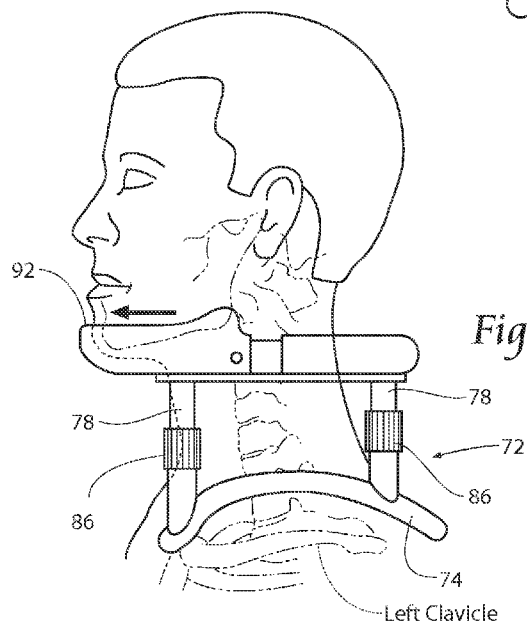

In the embodiment shown in FIGS. 25A, 25B, and 25C, the contoured channel 92 of the cranial region 76 slides on a track 90 for translating the channel 92 in an anterior direction. A locking screw 94 holdfasts the channel 92 in a desired translated position. The adjustable mandible resting channel 92 makes it possible to impose the third constraint condition 16, which is to provide and maintain an anterior position to the jaw. Resting the chin in the channel 92, and then translating the channel 92 forward moves the mandible forward, establishing a desired anterior orientation of the mandible. Upon being locked, the channel 92 maintains the mandible in a desired, slightly anterior (protruding) orientation, to thereby affirmatively resist inferior translational movement of the mandible within the TMJ.

Figure 26A:
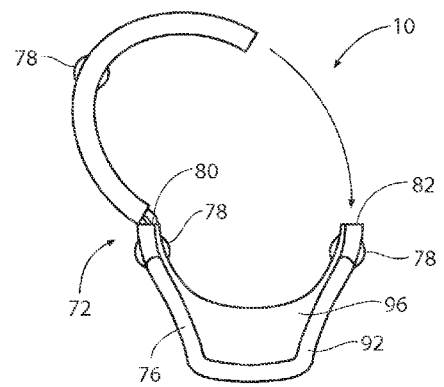
FIGS. 26A, 26B, and 26C are side elevation views of a representative embodiment of an apparatus like that shown in FIGS. 25A, 25B, and 25C, which includes a chin support surface to which an adhesive material can be applied to adhere to tissue.

Alternatively, in any of the above-described embodiments, the cranial region 76 of the structure 72 can include, instead of a formed, chin-fitting channel 92, a larger tissue support surface 96, as shown in FIG. 26A. In this embodiment, the tissue support region 96 is desirably formed of a flexible and soft material for user comfort, comprising, e.g., a soft, supple, breathable fabric, e.g., a webbing material.

Figure 26B:
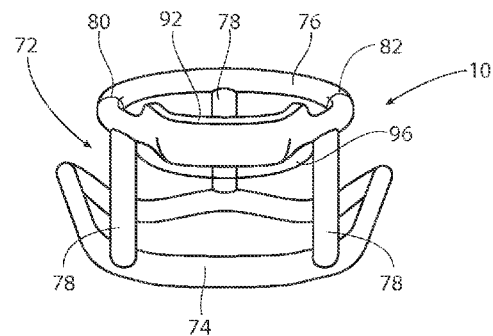
Figure 26C:
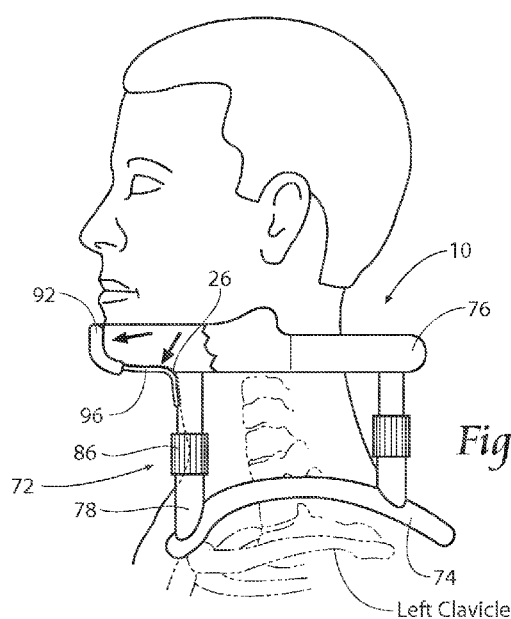

Further, as shown in FIG. 26B, an adhesive material 26 can be applied to the tissue support region 96. The adhesive material 26 adheres to surface tissue under the chin. The adherence of surface tissue to the tissue support region 96 can exert a stabilizing force on tissue structures in, on, or near the chin and the floor of the mouth. The stabilizing force draws the surface tissue in a caudial direction, away from the airway.

As will be described in greater detail later, because of the native, interconnected morphology of tissue structures in this region, the application of a stabilization force on surface tissue serves to also indirectly stabilize interior tissue structures in this region, e.g., intrinsic and extrinsic muscles of the tongue. The adherence of surface tissue to the tissue support region 96 braces tissue structures in, on, or near the chin and the floor of the mouth, to hold them in a desired orientation biased away from collapse into the airway. The mechanical stabilization and support can also serve to dampen vibration of these tissue structures, thereby moderating loud breathing or snoring during sleep.

The adherence of surface tissue to the tissue support region 96 can also enhance the anterior stabilization of the mandible, to resist inferior translational movement of the mandible within the TMJ and/or to impose the third constraint condition 16, which provides and maintain an anterior position to the jaw.

(vi) Helical Load Nearing Structure

FIGS. 27A and 27B show an alternative embodiment of a load bearing structure 72 that is sized and configured to be supported between rigid bony anchoring points between the shoulder and mandible.

The load bearing structure 72 includes a caudal region 74. The caudal region 74 is sized and configured to engage the chest and back in contact, at least in part, with the left and right clavicle, as FIG. 27C shows.

The load bearing structure 72 also includes a cranial region 76. The cranial region 76 is sized and configured to engage, at least in part, the bony perimeter of the mandible.

In the embodiment shown in FIGS. 27A, 27B, and 27C, the intermediate region of structure comprises a helical load bearing member 98, which spirals between the caudal and cranial regions 74 and 76.

As FIG. 27B shows, inserted between bony, rigid anchor points of the clavicle and mandible when the mouth is closed, the helically shaped load bearing member 98 applies a lifting force to the mandible, thereby constraining the mandible and/or head to keep the mouth closed and the chin lifted. The helically shaped load bear member 98 also applies a preferential torque to the mandible in the direction of the helical twist of the load bearing member 98. The helical load bearing member 98 thereby imposes an additional constraint condition, preferentially twisting the head to apply tension to muscles structures along the pharyngeal airway, thereby creating a more rigid airway.

The helical load bearing member 98 can comprise a preformed elastic or semi-elastic material. Alternately, the helical load bearing member 98 can comprise a structure that enlarges and expands in situ (e.g., in response to pneumatic fluid pressure) (see FIG. 27C) to fit and anchor itself in the space between the clavicle and mandible. In this arrangement, adjustment of the fluid pressure serves to adjust the lift and/or preferential torque that the helical structure 72 provides. As before described, the individual or healthcare assistant can select a desired magnitude of fluid pressure to achieve the therapeutic objectives of lift and/or preferential torque that are sought. Over time, the magnitude of fluid pressure can be titrated against the individual sleep performance, to optimize for that individual the magnitude of lift and/or preferential torque most conducive to deep, restorative sleep.

The expandable helical load bearing member 98 can be integrated into an overall therapeutic system, which controls the magnitude of the fluid pressure in response to a sensed sleep condition, e.g., a physical sleep position and/or sleep posture of the individual, either with respect to the position of the torso of the individual, or the position of the head of the individual, or both; sleep sound or vibration architecture; blood pressure; the level of oxygen in the blood; heart rate; respiration rate; periodic cessation of breathing, and/or muscle strain, or other sensed physiologic or physical conditions to adjust the magnitude of lift and torque in real time, most conducive to deep, restorative sleep.

As before stated, the load bearing structures as described above preferable avoid compressing tissue in, on, or near the floor of the mouth to avoid, during use, interference with the native anchoring function that the floor of the mouth provides to the mandible, hyoid bone, and tongue.

IV. Apparatus and Methods for Bracing Tissue Structures In, On, or Near the Neck Apparatus and methods have been described for constraining the mandible and/or head. The apparatus and methods have included, as a structural component, a neck piece 20. In these embodiments, the neck piece 20 serves as a carrier for a chin support 22, which was described as the structural component providing, in that embodiment, the primary therapeutic benefit of achieving a desired orientation of the mandible and/or head.

Figure 28A:
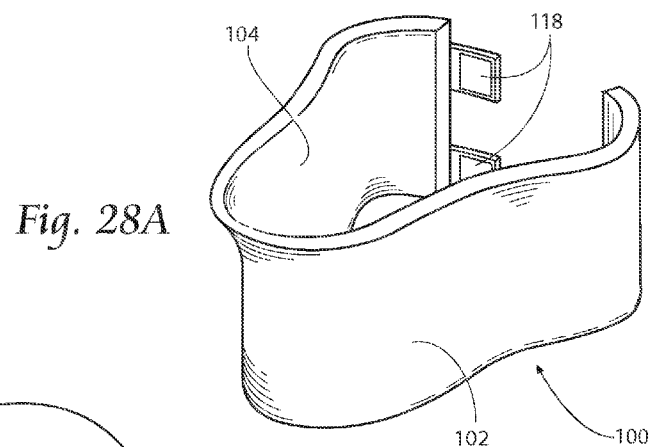
FIGS. 28A, 28B, and 28C are views of a representative embodiment of an apparatus comprising a neck piece to which an adhesive material is applied to externally brace tissue structures in, on, or near the neck, and/or along the walls of the pharyngeal airway, and/or the floor of the mouth.
Figure 28B:
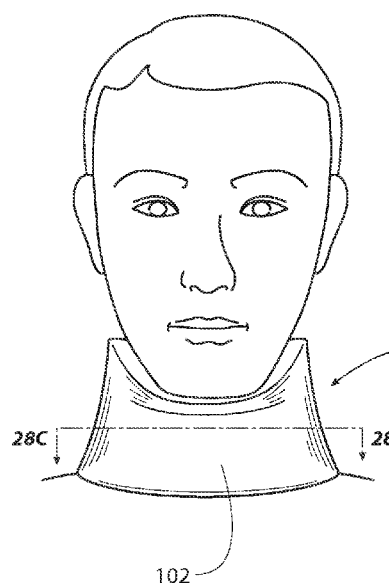
Figure 28C:
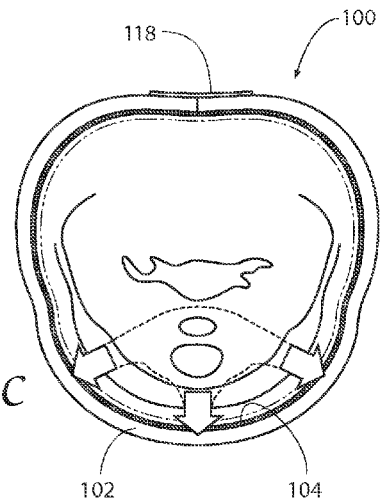

FIGS. 28A, 28B, and 28C shows an apparatus comprising a neck piece 100 that serves a different primary therapeutic benefit. This therapeutic benefit is to externally brace tissue structures in, on, or near the neck, and/or along the walls of the pharyngeal airway itself, and/or the floor of the mouth.

Diverse tissue structures occupy the neck, the pharyngeal airway, and floor of the mouth. These structures comprise layers of dermis, fat, and muscle, which are mutually interconnected from the epidermis inward to the tongue and base of the tongue. Due to their native, interconnected morphology, the application of a force to brace, move, or constrain one of these tissue structures in effect braces, moves, or constrains them all to various degrees. The neck piece 100 is sized and configured to mechanically stabilize and support these interconnected tissue structures in, on, near, or around (i.e., to fully circumferentially surround) the neck, pharyngeal airway, and floor of the mouth in a desired orientation biased away from collapse into the airway. The mechanical stabilization and support that the neck piece 100 provides affirmatively resists movement or collapse of, the tissue structures in, on, or near the neck, pharyngeal airway, and floor of the mouth toward and into the airway. The mechanical stabilization and support that the neck piece 100 provides can also serve to dampen vibration of these tissue structures, thereby moderating loud breathing or snoring during sleep.

As will be described, the neck piece 100 can function without use of external positive pressure ventilation techniques, like CPAP. However, the neck piece 100 can also be used in combination with CPAP, and/or intraoral oral appliances used to position the tongue and/or jaw during sleep, and/or with the Pillar® Procedure (Restore Medical Inc.), and/or tissue removal or other surgical intervention techniques, such as maxillomandibular advancement (MA) or uvulopalatopharyngeoplasty (UPPP). The additive effects of the neck piece 100 can serve to moderate the required nature and extent of these often highly invasive surgical procedures, thereby reducing the often long recover time and increasing patient appeal. When used in combination with CPAP, oral appliances, and surgical procedures, the presence of the neck piece 100 can increase the success rates of conventional treatments.

Desirably, structures that externally brace tissue structures in, on, or near the neck, and/or along the walls of the pharyngeal airway itself, and/or the floor of the mouth are sized and configured to avoid compressing tissue in, on, or near the floor of the mouth to avoid, during use, interference with the native anchoring function that the floor of the mouth provides to the mandible, hyoid bone, and tongue.

A. Overview

In FIGS. 28A, 28B, and 28C, the neck piece 100 takes the form of a collar 102 that is sized and configured to encircle the neck between the mandible and the clavicle (collar bone). The clavicle and mandible provide rigid, bony anchoring points for the collar 102. The collar 102 is flexible and soft for user comfort (desirably comprising a soft, supple, breathable fabric), but nevertheless possesses the requisite size and mechanical properties to perform in the manner described. The neck piece 100 can comprise a fabric material and be treated as a single or limited use, disposable item.

In the illustrated embodiment, the collar 102 is size and configuration to have an inside circumference that exceeds the native outer circumference of the neck by a small difference (e.g., less than 5 cm, and more desirably between about 0.5 cm to about 2 cm), which is determined by a healthcare provider based upon the anatomy and morphology of the individual wearing the collar 102. The slightly oversized collar 102 makes it possible to conform tissue structures in, on, or near the neck, the pharyngeal airway, and the floor of the mouth to an orientation away from the airway.

The neck piece 100 includes a pressure-sensitive medical grade adhesive gel or material 104 applied to the inside of the collar 102 (see FIGS. 28A and 28C). As previously described, the adhesive material 104 can comprise conventional pressure-sensitive compositions used for adhesion to the skin, particularly in the field of colostomy care. Representative pressure sensitive adhesive compositions comprise a self-adhesive elastomeric matrix, in which water-absorbing, swelling particles, called hydrocolloids, are dispersed.

Due to the presence of the adhesive material 104, the inside of the collar 102 adheres to surface tissue along the neck. As shown in FIG. 28C, because the inside circumference of the collar 102 is purposely slightly larger than the native circumference of the neck, the adhesive material 104 on the collar 102 draws tissue outward away from the tissue structures of the neck, pharyngeal airway, and floor of the mouth. The adhesive material 104 holds tissue in this position to exert a stabilizing force on tissue structures in, on, near, or around (i.e., to fully circumferentially surround) the neck, the pharyngeal airway, and the floor of the mouth.

Depending upon the anatomy and morphology of the individual wearing the collar 102, the inside circumference of the collar 102 may not need to significantly exceed the native outside circumference of the wearer's neck. The adhesion force created by the collar 102 and adhesive material 104 can mechanically brace and stabilize tissue structures in, on, or near the neck, pharyngeal airway, and floor of the mouth and thereby resist movement or collapse of these tissue structures into the airway. The collar 102 need not otherwise enlarge the circumference of the neck.

Still, if desired, the inside circumference of the collar 102 can be sized relative to the neck to also exert a pulling force on tissue structures in, on, or near the neck, the pharyngeal airway, and the floor of the mouth. The outward adhesive force reshapes these tissue structures toward the slightly larger circumference of the collar 102.

The collar 102 thereby serves to stabilize and/or reshape tissue structures in, on, or near the neck, pharyngeal airway, and floor of the mouth, holding and/or biasing them in a circumference and orientation, which is away from the collapse into the airway. The adhesion force between tissue along the neck and the adhesive material 104 on the oversized collar 102 braces tissue structures in, on, and near the neck, pharyngeal airway, and floor of the mouth against collapse into the airway. The adhesion force mechanically resists movement or collapse of the tissue inwardly toward the airway. In this respect, the collar 102 is unique in that it avoids inward pressure on soft tissue structure in, on, near the tongue and floor of the mouth. As before described, it is desirable to avoid compressing tissue in, on, or near the floor of the mouth to thereby avoid, during use, interference with the native anchoring function that the floor of the mouth provides to the mandible, hyoid bone, and tongue.

Figure 29A:
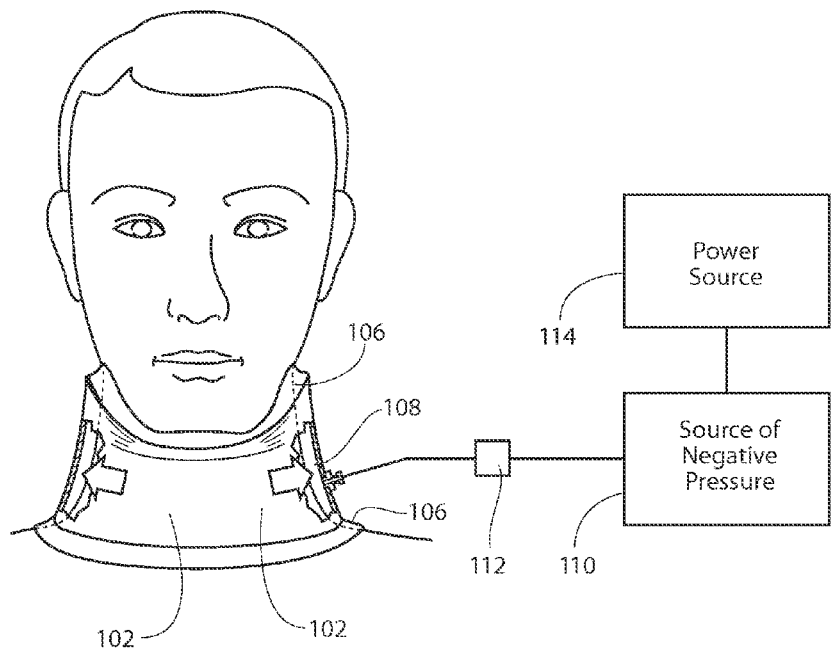
FIGS. 29A and 29B are views of a representative embodiment of an apparatus comprising a neck piece to which negative pressure is applied to externally brace tissue structures in, on, or near the neck, and/or along the walls of the pharyngeal airway, and/or the floor of the mouth.

The force that the adhesive material 104 on the collar 102 applies to the tissue structures can be augmented or enhanced, or replaced in its entirety, by the presence of negative pressure in the region between the inside of the collar 102 and the soft tissue of the upper neck and under the chin. As FIG. 29A shows, placement of a suitable sealing interface 106 between the mandible and clavicle anchor points can form a sealed chamber 108 along the interior of the collar 102. Applying negative pressure to the sealed chamber from an external source. 110 draws tissue away from the airway. The external source 110 can comprise, e.g., an air pump can be carried by the collar, or it can be located remote from the collar 102, e.g., bedside, and coupled by tubing to the air chamber 16, as FIG. 29A shows. The air pump 110 can comprise, e.g., a diaphragm pumping mechanism, or a reciprocating piston mechanism, or a centrifugal (turbine) air-moving mechanism. The air pump 110 may be manually operated, or a power source 114 may drive the air pump 110. The power source 114 can be, e.g., an electric motor that can be plugged into a conventional electrical receptacle, or be battery-powered, or both (in which case the battery can be rechargeable). When driven, the air pump 110 draws air from the chamber 108, to establish within the chamber 108 a pressure condition that is less than atmospheric.

A regulator 112 may be coupled to govern operation of the air pump 110 to establish and maintain a desired sub-atmospheric pressure condition within the chamber 108. The desired pressure condition is selected to be less than atmospheric pressure and is desirably less the minimum pressure condition expected experienced in the pharyngeal conduit, which is typically encountered during the inhalation phase of the respiration cycle. The pressure selected desirably nullifies the vector sum of the extralumenal forces, which are created by the interaction of atmospheric pressure, gravity, the contractive forces within the tissue due to upper airway muscle activity, and the inward forces generated by subatmospheric luminal pressure generated during inhalation. It is believed that the pressure condition established within the chamber 16 should be at least −1 cm $H_2O$ and desirable at least −10 cm $H_2O$. The pressure created desirably also takes into account different anatomical structural differences of individual airways.

Negative pressure can also be generated by use of a one way valve that allows air to escape (but not re-enter) when skin and the inside of the collar 102 are pressed together.

The presence of negative pressure complements the pulling force applied to tissue by the adhesive material 104 on the collar 102, to hold tissue structures in, on, or near the neck away from the airway.

Alternatively, negative pressure alone, without the use of adhesive material 104, can serve to hold tissue structures in, on, or near the neck away from the airway.

In another alternative arrangement (see FIG. 29B), the collar 102 can include an array of negative pressure ports 116 coupled to the external source 110. The ports 116 convey negative pressure and draw localized regions of tissue into contact with the interior of the collar 102, in the same fashion that an adhesive material 104 would and with the same beneficial affect of holding tissue structures in, on, or near the neck away from the airway.

In another alternative embodiment (see FIGS. 29C and 29D), a smaller, neck mask or cup 300 can be affixed by means of a flexible strap 302 in the region of the throat and/or floor of the mouth. The neck mask or cup 300 includes a sealing interface 304 about its periphery to form an interior air chamber 306 (see FIG. 29C). An air pump 308 can be coupled to the neck mask by tubing 310, to apply negative pressure to the air chamber 306, as FIG. 29C shows. When worn, as FIG. 29D shows, the presence of negative pressure within the air chamber 306 holds tissue structures in, on, or near the neck and/or floor of the mouth away from the airway.

B. Tissue Bracing

Figure 30A:
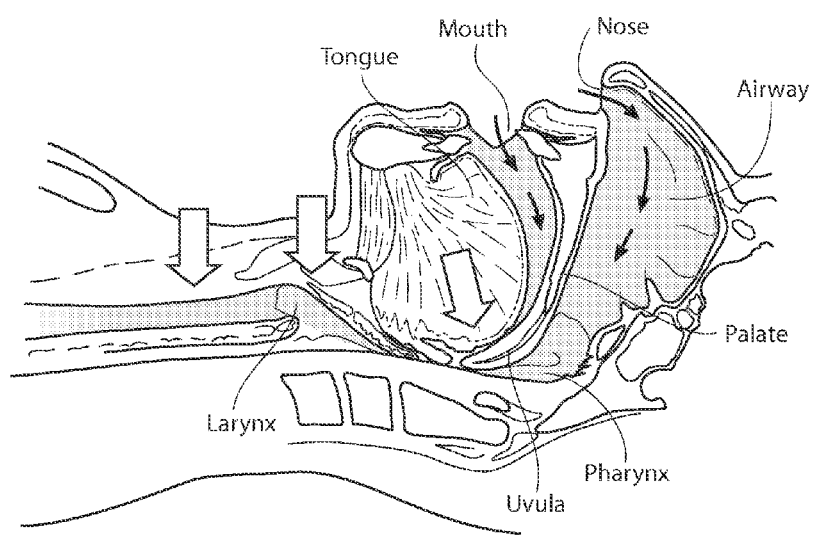

During sleep (see FIG. 30A), when a person is lying down in a prone, supine, or side position, and when muscles in or affecting neck, and/or the pharyngeal airway, and/or the floor of the mouth can relax, The mandible can drops (as FIG. 30A shows), and the mouth opens. During sleep, the head may also rotate inferiorly in flexion, or translation may occur within the TMJ to cause a posterior sliding of the mandible. The shift in mandible and/or head orientation during sleep leads to a shortening of the native anterior-to-posterior distance between the mandible and hyoid within the floor of the mouth. As the anterior-to-posterior distance is reduced by mandible and head orientation, the tongue and tissue structures in the floor of the mouth, which occupy this space, are shifted inward and toward the airway. Even in the absence of a reduction of the anterior-to-posterior distance between the mandible and hyoid bone, the diminution or absence of native muscle activity, and the force of gravity during sleep can shift the position of the root of the tongue in a posterior direction, toward and into the airway. Further, during sleep, the diminution or absence of native muscle activity in the neck can lead to the collapse of tissue in the neck toward and into the airway. As a result, the airway can be diminished or even blocked.

Figure 30B:
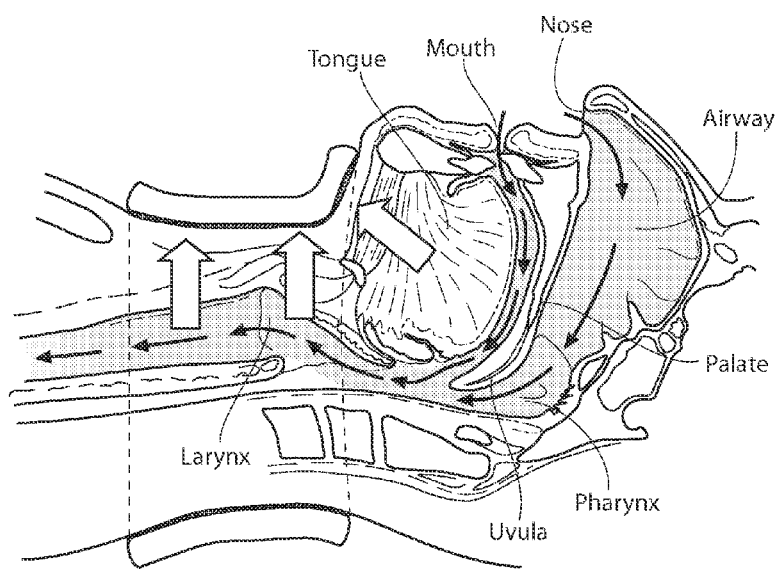
FIG. 30B is a side elevation view of the head of an individual in a supine sleep position, showing the an apparatus like that shown in FIGS. 28A/B/C or FIGS. 29A/B serving to externally brace tissue structures in, on, or near the neck, and/or along the walls of the pharyngeal airway, and/or the floor of the mouth, to resist collapse of tissue structures into the airway and thereby maintain airflow.

As shown in FIG. 30B, the presence of the collar 102 and the adhesive material 104 it carries conditions the tissue structures in, on, or near the neck, and/or the pharyngeal airway, and/or the floor of the mouth to resist collapse toward and into the airway. The presence of the collar 102 and the adhesive material 104 it carries braces these tissue structures outward, away from collapse into the airway. The collar 102 preferably includes a concave pocket region 430, which is sized and configured to receive tissue underlying the floor of the mouth, so that the collar 102, in use, does not compress the floor of the mouth to block the desirable lowering of the tongue and its beneficial effects upon the airway, as will be described in greater detail later.

The bracing effect of the apparatus is particularly advantageous for individuals having tissue structures that are enlarged or that otherwise lack normal tone or compliance. For such individuals, it may be warranted to tighten the skin of the neck prior to use of the collar 102. The skin of the neck can be tightened, e.g., surgically or by use of collagen tightening technologies, such injection of agents or by heat, or by liposuction, or by neck lifting techniques. The skin of the neck also may be locally tightened by wrapping with pressure sensitive tape prior to use of the apparatus.

As FIG. 29A shows, the collar 102 desirably includes releasable fasteners 118, e.g., such as snaps, magnets, buckles, straps, VELCRO® fabric, and the like, so that an individual can secure the collar 102 around their neck prior to use and remove the collar 102 from the neck after use. The adhesive material 104 releases upon remove of the collar 102. The fasteners 118 make it possible for the individual to loosen or tighten the collar 102 to adjusting the pulling force exerted on the tissue structures.

Figure 29B:
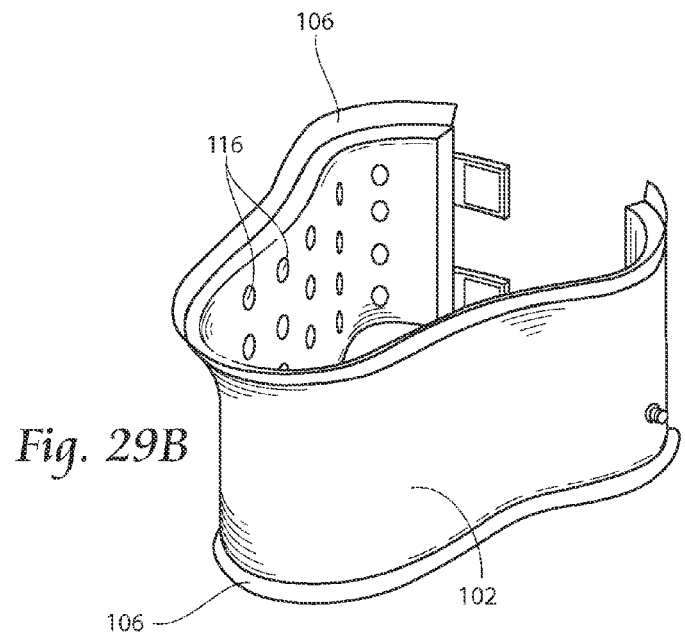
Figure 29C:
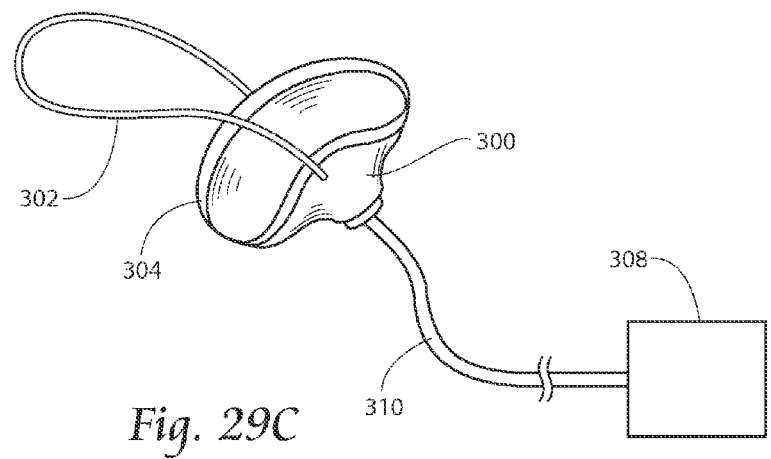
FIGS. 29C and 29D are views of a representative embodiment of an apparatus comprising a neck mask or cup to which negative pressure is applied to externally brace tissue structures in, on, or near the neck, and/or the floor of the mouth.
Figure 29D:
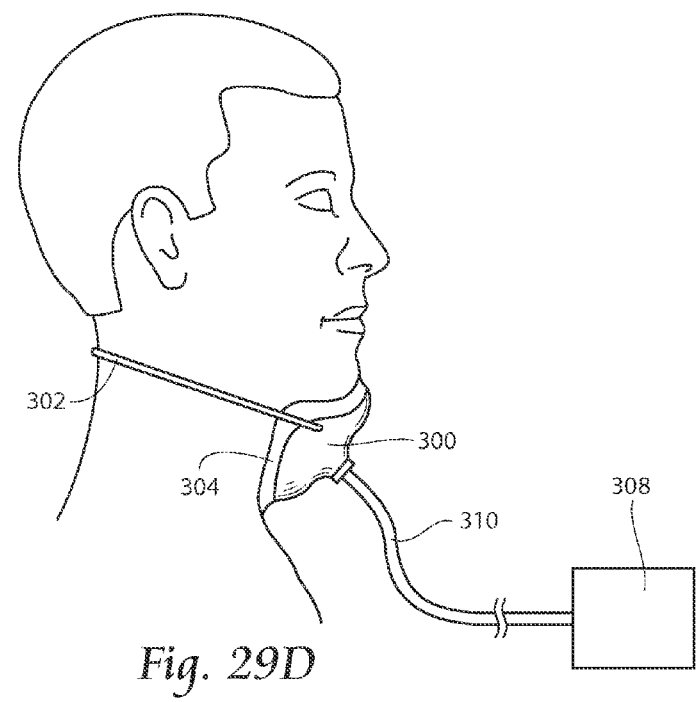
Figure 31A:
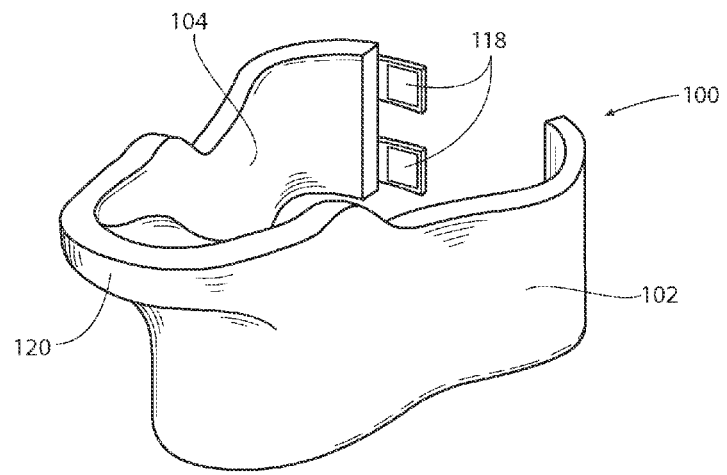
FIGS. 31A and 31B are perspective views of a representative embodiment of an apparatus comprising a neck piece and chin support to which an adhesive material is applied to externally brace tissue structures in, on, or near the neck, and/or along the walls of the pharyngeal airway, and/or the floor of the mouth.
Figure 31B:
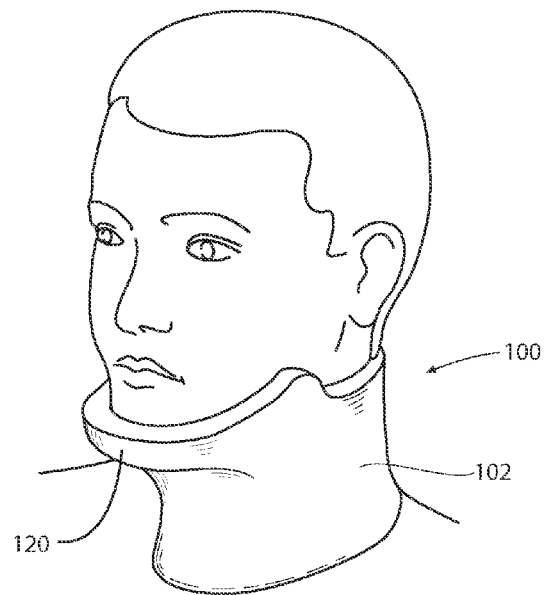

The collar 102 can be used by itself (as FIG. 29B shows), to achieve a beneficial bracing effect upon tissue structure in. on, or near the neck, the pharyngeal airway, and/or floor of the mouth. As FIGS. 31A and 31B show, the collar 102 can also include a chin support 120, like that previously described, to create a multi-function assembly 100 that combines neck bracing with mandible and/or head constraints.

The neck piece or collar 102 can be formed from elastic webbing material. Alternatively, the neck piece or collar 102 can comprise a pre-formed device made, e.g., from an elastic or semi-elastic polymer material. In either arrangement, the neck piece or collar 102 can be shaped, sized, and contoured based upon the particular anatomy of the individual who will wear the device. However, the neck piece or collar 102 can also be shaped, sized, and contoured based more upon a range of generic models of human anatomy.

The inside circumference of the collar 102, and the difference between it and the native outer circumference of the neck, can be assessed by medical professionals using textbooks of human skeletal anatomy, assisted by analysis of the morphology of the tissue structures in, on, or near the individual's neck, using, for example, plain films, MRI, or CRT scanning.

The inside circumference of the collar 102 can be titrated against the individual sleep performance, to optimize for that individual the inside circumference most conducive to deep, restorative sleep. The selection and application of adhesive material 104 used can also be titrated to optimize the desired results.

As discussed before, the size and configuration of the neck piece or collar 102, and the apparatus 100 in general, are also selected and contoured to limit direct pressure on soft tissue under the chin and in the floor of the mouth, to prevent an unintended inward movement of these tissue regions toward the airway and a resultant narrowing of the airway.

1. Variable Neck Bracing/Reshaping

The physical properties of the neck piece or collar 102 can be made variable. As shown in FIGS. 32A and 32B, the neck piece or collar 102 can include about its outer circumference pockets 122 that are sized and configured to receive reinforcing elements or stays 124. As previously discussed, the stays 124 can comprise strips of plastic material, but other cross-sectional configurations, linear or curvilinear, and material choices are possible. The physical properties of given stay 124 can be characterized in terms of, e.g., length, thickness, elasticity, tensile strength, flexure (Standard Gurley Units), compressibility, spring constant, torque, shape, etc. By the purposeful selection and insertion of stays 124, individually or in groups of two or more, the physical properties of the neck piece or collar 102, which affect its ability to brace tissue structures in, on, or near the neck, pharyngeal airway, and/or floor of the mouth can be incremental adjusted. Over time, the physical properties of the neck piece or collar 102 can be titrated against the individual sleep performance, to optimize for that individual the physical properties of the neck piece most conducive to deep, restorative sleep.

In one variation, the mechanical properties of the neck piece or collar 102 can be varied by control of an actuator 126. Operating the actuator 126, the mechanical properties of the neck piece in terms of its flexibility or stiffness and/or circumference can be incrementally varied. The mechanism for varying the mechanical properties of the neck piece can vary. For example, the stays 124 may comprise shape activated materials that stiffen, e.g., in result to the conduction of electrical current.

2. Dynamic Neck Bracing/Reshaping

In an illustrated embodiment (see FIGS. 33A and 33B), the neck piece or collar 102 includes chambers 128 that receive fluid pressure from a source 130 through a solenoid control valve 130. The fluid pressure expands or contacts the circumference of the neck piece or collar 102, and also makes the neck piece or collar 102 more or less flexible. The actuator operates to valve, to progressive introduce more or less fluid pressure into the chambers of the neck piece. Progressive fluid pressure alterations can stiffen or soften the neck piece and also constrict or expand its circumference.

The actuator 126 can be operated manually by the individual or by a healthcare assistant. The actuator 126 can include a manual control and pressure magnitude readings or settings. Using the actuator 126, the individual or healthcare assistant can select a desired magnitude of pressure. Over time, the magnitude of pressure can be titrated against the individual sleep performance, to optimize for that individual the magnitude of lift most conducive to deep, restorative sleep.

Figure 33A:
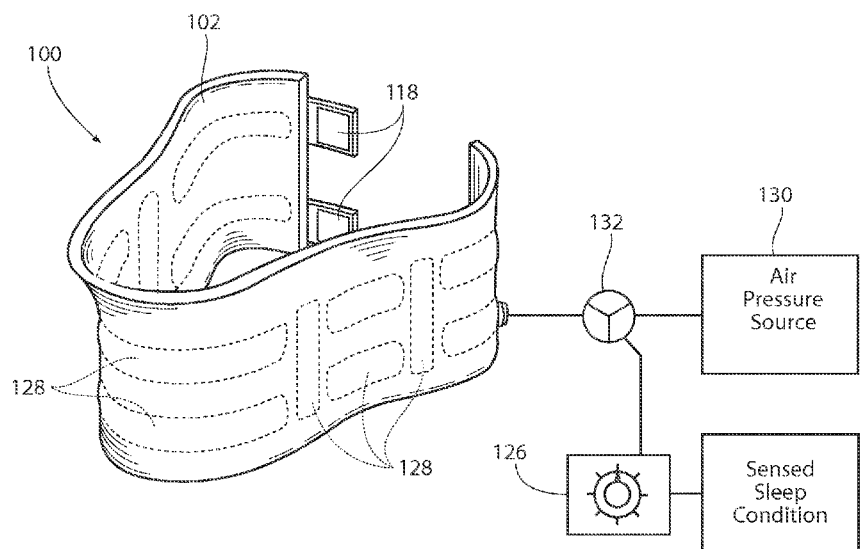
FIGS. 33A and 33B are perspective views of a representative embodiment of an apparatus like that shown in FIG. 28A, in which its ability to brace tissue structures in, on, or near the neck, pharyngeal airway, and/or floor of the mouth can be incremental adjusted by use of fluid or gas pressure, and which can be integrated into an overall therapeutic system, which controls tissue bracing in response to a sensed sleep condition.
Figure 33B:
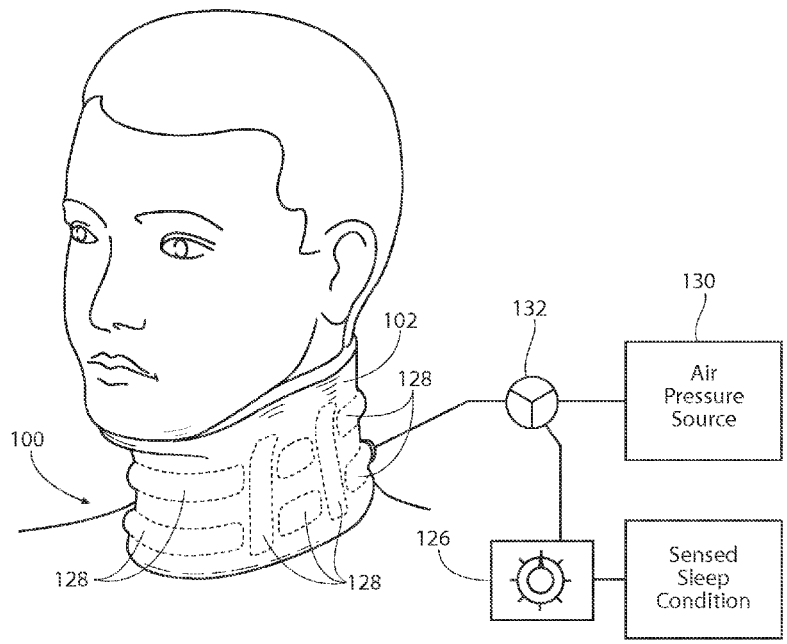

As FIGS. 33A and 33B show, a dynamically controlled apparatus 100 for shaping the neck can be integrated into an overall therapeutic system 134, which controls the actuator 126 in response to a sensed sleep condition, e.g., a physical sleep position and/or sleep posture of the individual, either with respect to the position of the torso of the individual, or the position of the head of the individual, or both; sleep sound or vibration architecture; blood pressure; the level of oxygen in the blood; heart rate; respiration rate; periodic cessation of breathing, and/or muscle strain, or other sensed physiologic or physical conditions, to provide deep, restorative sleep.

Moving the head or mandible may be one of the simplest and most effective means to correct an apnea event. Thus, the dynamically controlled apparatus 100 can also affect the magnitude and/or direction of constraining forces on the mandible and head in the manner previously described and disclosed in FIG. 19A. In this manner, an actuator 34 coupled to the chin support 22 makes it possible to articulate the chin support 22 by operation of the actuator 34, to exert a progressive lifting force and/or rotation force on an individual's mandible and head, in response to sensed conditions. As previously mentioned, a lifting force and/or rotational force on the chin and mandible can also serve to stretch and maintain an opened airway. Moving the head or mandible may be one of the simplest and most effective means to correct an apnea event.

This dynamically controlled apparatus 100 can also be integrated with positive air pressure systems, such that the magnitude of positive air pressure being applied becomes one of the sensed conditions that affects the orientation of collar. Positive pressure is applied to a nose mask, full face mask, or nasal pillow worn by the individual. A machine coupled to the mask delivers a stream of compressed air to the delivery device at a prescribed pressure, which is also called the titrated pressure. The intent of CPAP is to splint the airway (keeping it open under air pressure) so that unobstructed breathing becomes possible, reducing and/or preventing snoring, apneas, and hypopneas.

For example, when high titrated pressures are required, the mask must be tightened. This causes the mandible to drop and the tongue to fall back, thereby causing even higher pressures. Sensing this condition, and, in response, adjusting the collar 102 to exert a lifting force and/or rotation force on an individual's mandible and head, will reduce the pressure requirement or allow higher pressure to be applied without overly tightening the mask.

Therefore, the collar 102 can be integrated with positive airway pressure masks (pillows and the like) to effect head position and tissue stabilization while administering positive airway pressure therapy.

V. Scaffolds In, On, or Near the Floor of the Mouth

A. Overview

As FIGS. 1A and 1B show, the oral cavity is framed by relatively stable structures—i.e., the rigid structures comprising the hard palate and cervical spine—and the floor of the mouth. The floor of the mouth comprises superficial muscles such as the mylohyoid and geniohyoid. The floor of the mouth is bounded by the rigid, movable structures of the mandible (anterior) and the hyoid bone (posterior). The muscles of the floor of the mouth extend between these rigid, movable structures. Along with the mandible and the hyoid bone, the muscles in the floor of the mouth also serve as an anchoring structure for the tongue. The region behaves like a trampoline, stabilizing these structures, while accommodating relative movement among them.

Figure 1C:
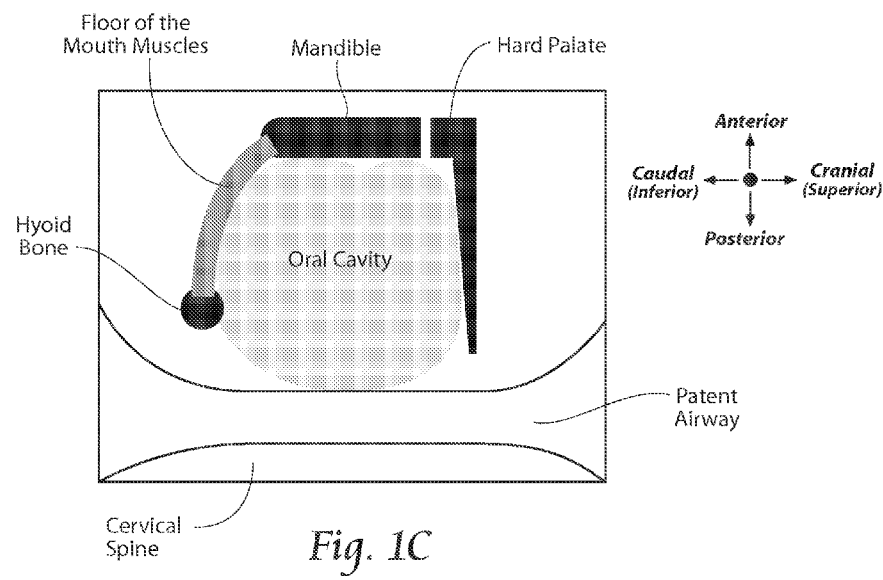
FIGS. 1C and 1D are diagrammatic views of an oral cavity and an airway, showing how a change in the frame size of the oral cavity affects airway patency.

While awake, the frame size is maintained by active tension in the floor of the mouth muscles (i.e., keeping the trampoline taunt). The active tension in the frame in turn maintains the anterior position of the mandible, creating more volume in the oral cavity and thus an airway of sufficient diameter. This is also shown diagrammatically in FIG. 1C.

Figure 1D:
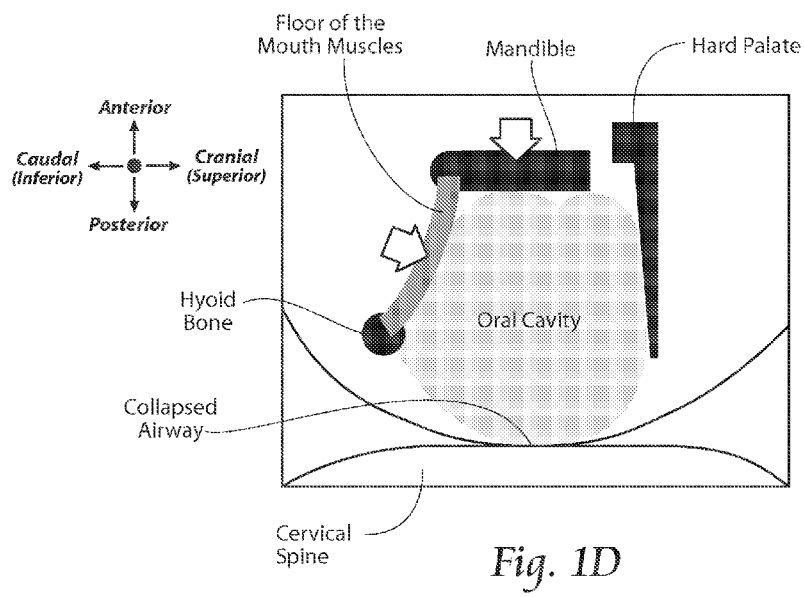

However, absence of muscle activity during sleep, gravity, and the negative pressure cascade during the breathing cycle all create conditions for the tongue to slide in a posterior direction and close the airway. This is shown diagrammatically in FIG. 1D. During sleep, the floor of the mouth muscles lose active tension, and the trampoline becomes slack. The mandible drops and falls back (in a posterior direction) due to lack of tension in other muscles. The slack muscles in the floor of the mouth buckle or bend inward, because the tongue pulls the muscles in the floor of the mouth inward. The mandible repositions toward the airway, shortening the distance between the mandible and the hyoid. The frame size of the oral cavity decreases. The tongue slides to the posterior and closes the airway.

Figure 34A:
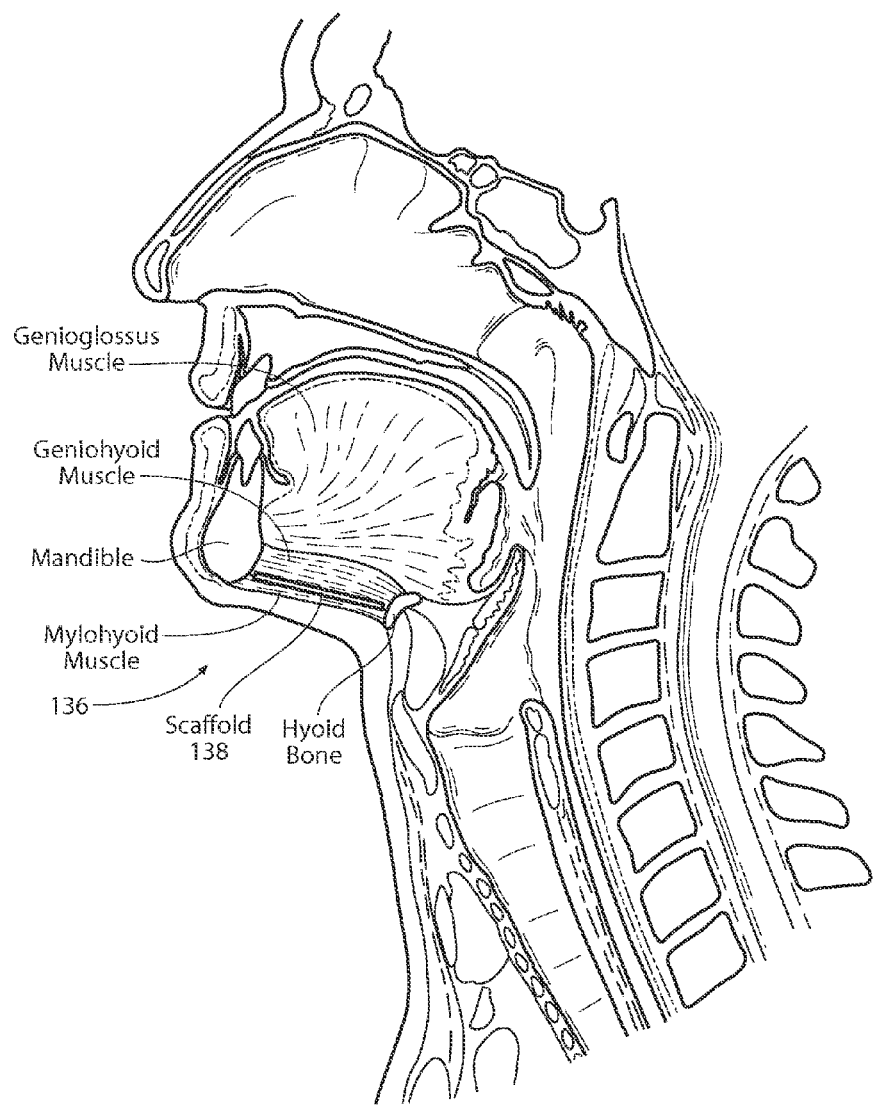

FIGS. 34A, 34B, and 34C show a system 136 comprising at least one scaffold 138 placed in, on, or near selected tissue regions in the floor of the mouth. In use, the scaffold 138 helps an individual with a sleep disordered breathing condition, such as habitual snoring or obstructive sleep apnea (OSA), achieve deep, restorative sleep. As FIGS. 34A, 34B, and 34C show, at least one of the scaffolds 138 is placed in, on, or near the selected tissue regions in the floor of the mouth between the anterior part of the mandible and the hyoid bone.

The diverse tissue structures occupying the floor of the mouth comprise layers of dermis, fat, and muscle, which are mutually interconnected from the epidermis inward to the genioglossis muscle, tongue and base of the tongue. Due to their native, interconnected morphology, the application of a force to brace, move, or constrain one of these tissue structures in effect braces, moves, or constrains them all to various degrees. By analogy, this structure has previously compared to a trampoline, which provides for both motion and stabilization of the tongue. The scaffold 138, in effect, stiffens and shapes the trampoline.

The scaffold 138 comprises a shaped, elongated body made from a biocompatible metallic or polymer material, or a metallic or polymer material that is suitably coated, impregnated, or otherwise treated with a material to impart biocompatibility, or a combination of such materials.

The physical characteristics of the scaffold 138 body are selected in term of length, thickness, elasticity, tensile strength, flexure (Standard Gurley Units), compressibility, spring constant, torque, shape, etc., so that, when placed in tissue, the scaffold 138 mechanically supports the selected tissue region in a desired orientation in the floor of the mouth, even in the absence or diminution of native muscle activity in that region. To achieve this function, the scaffold 138 comprises mechanical supporting means for bracing and resisting inward buckling of suprahyoid muscles in or on the floor of the mouth into the airway during sleep that comprise a rigid material, or a semi-rigid, or an elastic material with a selected spring constant (e.g., a spring constant similar to tongue tissue), or an electrically actuated shaped material, or a thermally activated shaped material, or combinations thereof. The scaffold 138 can also comprise a fluid or material that is injected into the floor of the mouth and that stiffens or cures in situ by itself (e.g., by cross-liking) or in response to applied external energy such as light, ultrasound, heat, or radio frequency energy. The scaffold 138 can also comprise a region of tissue in the floor of the mouth that has been ablated, e.g., by the application of radio frequency energy, heat, laser, or cold, to form lesions and stiffen. The mechanical support that the scaffold 138 provides stabilizes the tissue region, thereby providing affirmatively resistance to movement of the selected tissue region out of the desired orientation, which would otherwise occur due to the absence or diminution of native muscle activity in that region. The mechanical support that the scaffold 138 provides can also serve to dampen vibration of the tissue region, thereby moderating loud breathing or snoring during sleep.

Figure 35A:
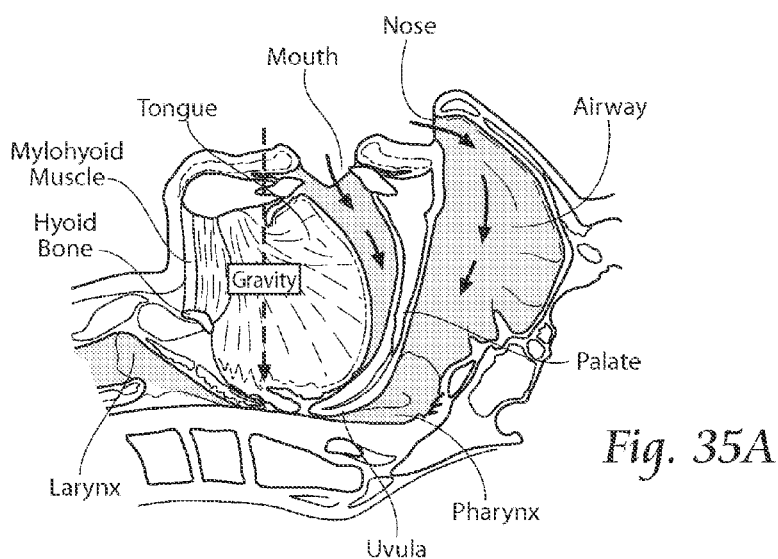
FIG. 35A is an anatomic side section view of an oral cavity, pharynx, and larynx of an adult human, in a supine sleep position with the mouth opened, showing the effects of gravity and an opened mouth on tissue structures along airway, being annotated to show the collapse of certain tissue structures into the airway and the resultant obstruction of airflow.
Figure 35B:
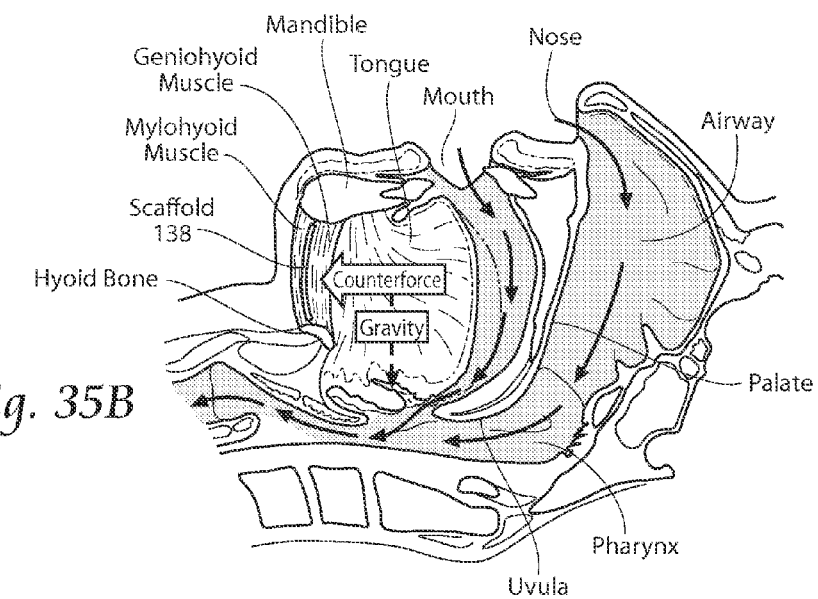
FIG. 35B is an anatomic side section view of the oral cavity of the individual shown in FIG. 35A, annotated to show the scaffold shown in FIGS. 34A/B/C functioning to mechanically support tissue structures in, on, or near the floor of the mouth and affirmatively resist their movement into an airway.

As shown in FIGS. 35A and 35B, the desired orientation provided by the scaffold's mechanical support can, e.g., serve to resist undesired posterior movement of a tongue during sleep. As previously described with respect to FIG. 1D (and as also shown anatomically in FIG. 35A), a lack of native muscle activity in the floor of the mouth during sleep can cause the root of the tongue to fall posteriorly, to narrow or obstruct the airway. As previously described, the mandible drops and falls back (in a posterior direction); the muscles in the floor of the mouth buckle or bend inward; and the mandible repositions toward the airway, shortening the distance between the mandible and the hyoid. This change in distance and tension between the mandible and hyoid leads to a decrease in the frame size of the oral cavity. The decrease in frame size causes the tongue to collapse into the airway. The tongue slides in a posterior direction and closes the airway.

Figure 35C:
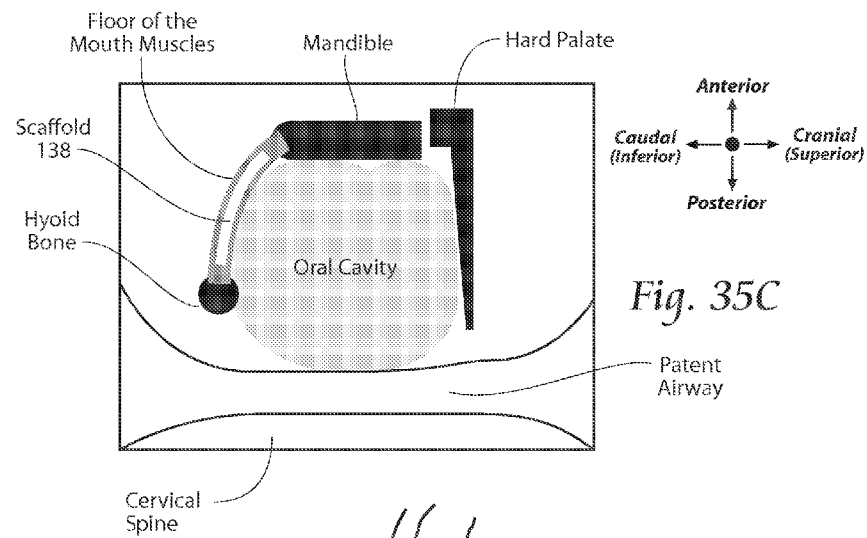
FIG. 35C is a diagrammatic side view of an oral cavity and an airway, like that shown in FIGS. 1C and 1D, showing how the presence of a scaffold as shown in FIG. 35B affects airway patency.

As FIG. 35B shows, the mechanical support of the scaffold 138 in the floor of the mouth conditions tissue to support the tongue in a desired anterior orientation, in effect mimicking native muscle activity that supports the tongue through interaction with the hyoid bone. Referring again to the analogy, the scaffold 138 stiffens and shapes the trampoline. This is shown diagrammatically in FIG. 35C. The scaffold 138 increases the tension in the floor of the mouth, preventing inward buckling and stabilizing the floor of the mouth to increase resistance to posterior tongue collapse. The scaffold 138 increases the distance and maintains tension between the mandible and hyoid, biasing the position of the mandible toward a mouth closed, chin up, jaw forward orientation. The mechanical support of the scaffold 138 in the floor of the mouth stabilizes the tissue region in the absence of the native muscle activity during sleep, to resist posterior movement of the tongue into the pharyngeal airway.

The desired orientation provided by the scaffold's mechanical support can also, e.g., serve to bias the displacement of tissue structures in, on, or near the floor of the mouth away from the airway when the mandible opens. As previously described, when the mandible opens (articulates downward), the anterior-to-posterior distance between the mandible and hyoid shortens, and tissue structures in, on, or near the floor of the mouth shift. Typically, due to the gravity position of the individual when sleeping (no longer upright), and the relaxation of muscles during sleep, when the mouth opens, tissue structures in, on, or near the floor of the mouth tend to shift toward the airway. The scaffold's mechanical support resists this tendency, by the creation of a counter force that directs the tissue structures out of the airway, as shown by the counterforce arrow in FIG. 35B. The scaffold 138 thereby reshapes the floor of the mouth. The outward force counteracts the inward force due to gravity. The scaffold 138 thereby increases the frame size of the oral cavity, increasing the oral cavity volume, while also stabilizing the frame in this condition. The presence of the scaffold 138 provides a subtle shift in the balance of forces in the oral cavity during sleep, to stabilize the tongue base and maintain oral cavity volume by increasing and stabilizing the frame size. Even a small increase in the cross sectional area of the airway results in an exponential improvement in airway stability.

The desired orientation provided by the scaffold's mechanical support can also, e.g., affirmatively serve to resist posterior translation of the TMJ, without opening the mouth during sleep. As previously described, a lack of native muscle activity can cause a posterior translation of the TMJ, which, in turn, can cause a narrowing of the pharyngeal airway. The mechanical support of the scaffold 138 in the floor of the mouth conditions tissue to resist posterior translation of the TMJ during sleep, to stabilize the tissue region in the absence of the native muscle activity during sleep, to resist narrowing or closure of the pharyngeal airway.

B. Representative Placement in Selected Tissue Regions In, On, or Near the Floor of the Mouth The scaffold 138 can be placed anywhere in the floor of the mouth from the superficial dermis of the skin to within the genioglossis muscle. This is because of the interconnected nature of tissue structures in this region. By stabilizing or bracing one of the tissue structures within the region, other interconnected tissue structures to can be stabilized and/or constrained.

Representative embodiments will now be described for the sake of illustration and not limitation.

1. Between Mylohyoid and Geniohyoid Muscles FIGS. 34A/B/C, 35A/B

In one representative embodiment (shown in FIGS. 34A/B/C and FIG. 35B), the scaffold 138 is placed between a mylohyoid muscle and a geniohyoid muscle in, on, or near the floor of the mouth. Both suprahyoid muscles originate at the mandible and are inserted in the hyoid bone.

The mylohyoid serves to elevate the hyoid bone, the floor of the mouth, and tongue during swallowing and speaking.

The geniohyoid serves to pull the hyoid bone anterosuperiorly (forward and up), shorten the floor of the mouth, and widen the pharynx.

Placement of a scaffold 138 between these two suprahyoid muscles in, on, or near the floor of the mouth provides mechanical support within the tissue region that resists the formation of undesired physiologic conditions in the floor of the mouth caused by a diminution or absence of the native activities of these suprahyoid muscles during sleep.

For example, when placed between the mylohyoid muscle and a geniohyoid muscle in, on, or near the floor of the mouth, the scaffold 138 provides mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold 138 and muscles can also serve to stabilize a desirable tissue orientation affected by the mylohyoid muscle, which is favorable to maintaining an open airway. The mechanical support of the scaffold 138 thereby resists formation of a contrary tissue orientation when the muscles relax during sleep, contrary gravity conditions exist, and/or the mouth opens, characterized by a lack of resistance to a posterior dropping of the floor of the mouth and the tongue, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, would otherwise arise due to a diminution or absence of the native activity or the mylohyoid during sleep. By resisting this contrary tissue orientation, the scaffold 138 resists a narrowing or obstruction of the pharyngeal airway and resulting apneic episode.

When placed between a mylohyoid muscle and a geniohyoid muscle in, on, or near the floor of the mouth, the interaction between the scaffold 138 and muscles can also provide mechanical support to tissue in the floor of the mouth that stabilizes a desirable tissue orientation affected by the geniohyoid muscle, which is favorable to maintaining an open pharyngeal airway. The mechanical support of the scaffold 138 thereby resists formation of a contrary tissue orientation, when the muscles relax during sleep, contrary gravity conditions exist, and/or the mouth opens, characterized by a lack of resistance to movement of the hyoid bone posteriorly and inferiorly (backward and down), widening the floor of the mouth, and narrowing the pharynx, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, could otherwise arise due to a diminution or absence of the native activity or the geniohyoid during sleep. By resisting this other contrary tissue orientation, the scaffold 138 further resists a narrowing or obstruction of the pharyngeal airway and resulting apneic episode.

The scaffold 138 may be implanted in muscles tissue in the floor of the mouth without attachment to the rigid structures of the mandible and/or hyoid bone. Alternatively, the scaffold 138 may be attached to one or both of these rigid bone structures, e.g., by screws, suture, or clamping. A representative embodiment of a scaffold 138 fixed to both the mandible and hyoid bone is shown in FIG. 34D. By attaching the ends of a flexible scaffold 138 to rigid structures, the shape of the implant can be influenced. As shown in FIG. 34D, the flexible scaffold 138 can be fixed with an outward bend, to bias the muscle structures in the floor of the mouth in an outward orientation for the creation of the counter force that directs the tissue structures out of the airway, drawing the hyoid forward. Alternatively, the flexible scaffold 138 can be activated by an energy source, e.g., electrical or thermal energy or the like, to assume the outward bend or to stiffen upon demand. The connection point between the scaffold 138 and the rigid bone structure or structures can include a hinge or a spring-loaded hinge to enhance the tissue shaping functions of the scaffold 138.

2. Between Geniohyoid and Genioglossus Muscles

Figure 36:
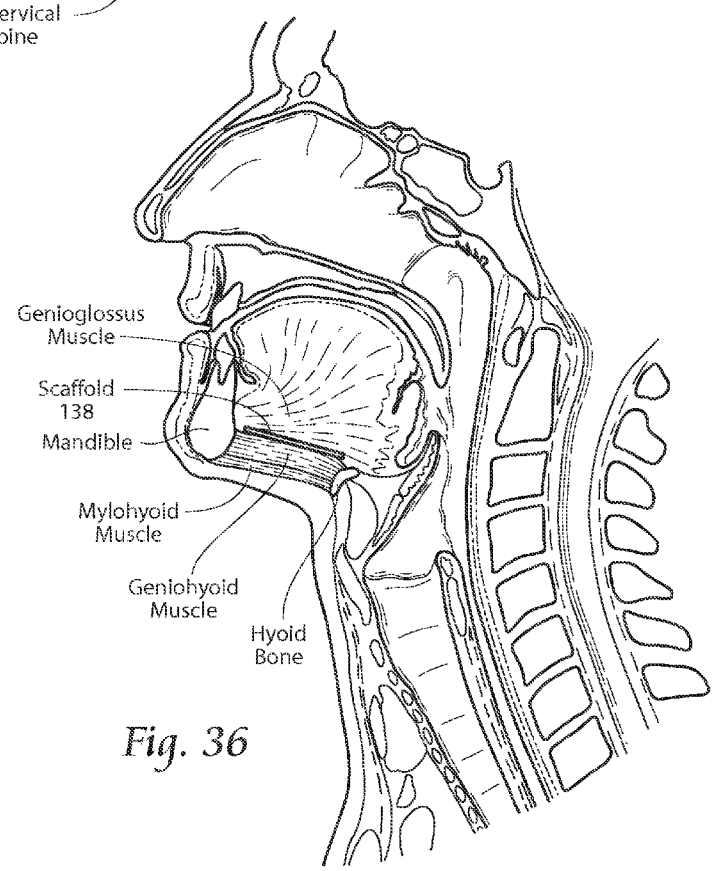

In another representative embodiment (shown in FIG. 36), the scaffold 138 is placed between a geniohyoid muscle and a genioglossus muscle in, on, or near the floor of the mouth.

The geniohyoid muscle is a suprahyoid muscle that originates at the mandible and is inserted in the hyoid bone. The geniohyoid muscle serves to pull the hyoid bone anterosuperiorly (forward and up), shorten the floor of the mouth, and widen the pharynx.

The genioglossus muscle is an extrinsic muscle of the tongue that originates at the superior part of the mental spine of the mandible and is inserted in the dorsum of the tongue as well as the body of the hyoid bone. The genioglossus muscle serves pull the tongue anteriorly for protrusion.

Placement of a scaffold 138 between an extrinsic muscle of the tongue (which inserts into the hyoid bone) and a suprahyoid muscle (which also inserts into the hyoid bone) provides mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold 138 and muscles can also serve to resist the formation of undesired physiologic conditions in the floor of the mouth caused by a diminution or absence of the native activities of these muscles during sleep.

For example, when placed between a geniohyoid muscle and a genioglossus muscle in, on, or near the floor of the mouth, the scaffold 138 can provide mechanical support to tissue in, on, or near the floor of the mouth that stabilizes a desirable tissue orientation affected by the geniohyoid muscle, which is favorable to maintaining an open pharyngeal airway. The mechanical support of the scaffold 138 thereby resists formation of a contrary tissue orientation, when the muscles relax during sleep, contrary gravity conditions exist, and/or the mouth opens, characterized by a lack of resistance to movement of the hyoid bone posteriorly and inferiorly (backward and down), widening the floor of the mouth, and narrowing the pharynx, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, would otherwise arise due to a diminution or absence of the native activity or the geniohyoid during sleep. By resisting this contrary tissue orientation, the scaffold 138 resists a narrowing or obstruction of the pharyngeal airway and resulting apneic episode.

Furthermore, when placed between the geniohyoid muscle and a genioglossus muscle in, on, or near the floor of the mouth, the scaffold 138 provides mechanical support to tissue in the floor of the mouth that stabilizes a desirable tissue orientation affected by the genioglossus muscle, which is favorable to maintaining an open pharyngeal airway. The mechanical support of the scaffold 138 thereby resists formation of a contrary tissue orientation, when the muscles relax during sleep, contrary gravity conditions exist, and/or the mouth opens, characterized by a lack of resistance to posterior movement of the tongue, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, could otherwise arise due to a diminution or absence of the native activity or the genioglossus during sleep. By resisting this contrary tissue orientation, the scaffold 138 resists a narrowing or obstruction of the pharyngeal airway and resulting apneic episode.

As before explained, the scaffold 138, if desired, may be attached to one or both of the rigid bone structures of the mandible and hyoid bone, e.g., by screws, suture, or clamping, as previously shown in FIG. 34D. By attaching the ends of a flexible scaffold 138 to rigid structures, the shape of the implant can be influenced. As shown in FIG. 34D, the flexible scaffold 138 can be fixed with an outward bend, to bias the muscle structures in the floor of the mouth in an outward orientation for the creation of the counter force that directs the tissue structures out of the airway, drawing the hyoid forward. Alternatively, the flexible scaffold 138 can be activated by an energy source, e.g., electrical or thermal energy or the like, to assume the outward bend or to stiffen upon demand. The connection point between the scaffold 138 and the rigid bone structure or structures can include a hinge or a spring-loaded hinge to enhance the tissue shaping functions of the scaffold 138.

3. Between Digastric and Mylohyoid Muscles

In another representative embodiment (shown in FIG. 37), the scaffold 138 is placed between a digastric muscle and a mylohyoid muscle in, on, or near the floor of the mouth. Both are suprahyoid muscles that originates at the mandible and is inserted in the hyoid bone.

The digastric muscle serves to depress (close) the mandible and raise the hyoid bone during swallowing and speaking.

The mylohyoid serves to elevate the hyoid bone, the floor of the mouth, and tongue during swallowing and speaking.

For example, when placed between the suprahyoid digastric and mylohyoid muscles, the scaffold 138 can provide mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold 138 and muscles can also serve to resist the formation of undesired physiologic conditions in the floor of the mouth caused by a diminution or absence of the native activities of these muscles during sleep.

For example, when placed between a digastric muscle and a mylohyoid muscle in, on, or near the floor of the mouth, the scaffold 138 provides mechanical support to tissue in, on, or near the floor of the mouth that stabilizes a desirable tissue orientation affected by the digastric muscle, which is favorable to maintaining an open pharyngeal airway. The mechanical support of the scaffold 138 thereby resists formation of a contrary tissue orientation, when the muscles relax during sleep, contrary gravity conditions exist, and/or the mouth opens, characterized by a lack of resistance to the depression (closing) of the mandible, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, would otherwise arise due to a diminution or absence of the native activity or the digastric during sleep. By resisting this contrary tissue orientation, the scaffold 138 resists a narrowing or obstruction of the pharyngeal airway and resulting apneic episode.

Furthermore, when placed between the digastric muscle and the mylohyoid muscle in, on, or near the floor of the mouth, the scaffold 138 provides mechanical support to tissue in the floor of the mouth that stabilizes a desirable tissue orientation affected by the mylohyoid muscle, which is favorable to maintaining an open pharyngeal airway. The mechanical support of the scaffold 138 thereby resists formation of a contrary tissue orientation, when the muscles relax during sleep, contrary gravity conditions exist, and/or the mouth opens, characterized by a lack of resistance to a dropping of the floor of the mouth and the tongue, which is not favorable to maintaining an open pharyngeal airway and which, instead, leads to a narrowing or obstruction of the pharyngeal airway. The mechanical support of the scaffold 138 moderates the undesirable physiologic conditions that, in the absence of the scaffold 138, would otherwise arise due to a diminution or absence of the native activity or the mylohyoid during sleep. By resisting this contrary tissue orientation, the scaffold 138 resists a narrowing or obstruction of the pharyngeal airway and resulting apneic episode.

As before explained, the scaffold 138, if desired, may be attached to one or both of the rigid bone structures of the mandible and hyoid bone, e.g., by screws, suture, or clamping, as previously shown in FIG. 34D. By attaching the ends of a flexible scaffold 138 to rigid structures, the shape of the implant can be influenced. As shown in FIG. 34D, the flexible scaffold 138 can be fixed with an outward bend, to bias the muscle structures in the floor of the mouth in an outward orientation for the creation of the counter force that directs the tissue structures out of the airway, drawing the hyoid forward. Alternatively, the flexible scaffold 138 can be activated by an energy source, e.g., electrical or thermal energy or the like, to assume the outward bend or to stiffen upon demand. The connection point between the scaffold 138 and the rigid bone structure or structures can include a hinge or a spring-loaded hinge to enhance the tissue shaping functions of the scaffold 138.

C. Representative Scaffold Configurations

1. General Physical Characteristics

FIGS. 34A/B/C show a basic representative embodiment of a scaffold 138.

As shown, the scaffold 138 desirably includes a side profile, measured in the inferior to superior direction when implanted, which is as thin as possible. Representative side profiles can range, e.g., up to about 10 mm; however, a side profile of between about 1 mm and 4 mm is believed to be most desirable. This attributes lends comfort to the scaffold 138 when implanted.

Desirably, the scaffold 138 is generally rectangular in shape, having a length greater than its width, to maintain a desired orientation when implanted. Further, as shown, the scaffold 138 is sized in length to rest comfortably in the anterior-to-posterior space between the hyoid. A representative length ranges between about 30 mm and about 40 mm. In one representative embodiment, the anterior region and the posterior region of the scaffold 138 rest about 5 mm from the mandible and hyoid, respectively. In other representative embodiments, the scaffold 138 can rest closer to or farther from the mandible and/or hyoid, e.g., as far as 1 cm from the mandible and/or hyoid.

The scaffold 138 may be sutured to surrounding tissue, as desired, for stabilization. However, suturing is not believed to be necessary in all instances. Local tissue morphology will dictate whether suturing is required for stabilization. The most desired location for suturing is around the hyoid or to the connective tissue attached to the hyoid.

The scaffold 138 can comprise a rigid or semi-rigid material. In use, the scaffold 138 is implanted in a tissue structure in, on, or near the floor of the mouth with the longitudinal length of the scaffold 138 oriented in an anterior-to-posterior direction. Inferior/posterior rotation or posterior translation of the mandible will tends to shorten the anterior-to-posterior distance between the hyoid and the mandible. As before described, a reduction in the anterior to posterior distance between the mandible and hyoid, if not resisted, will displace tissue structures in, on, or near the floor of the mouth cranially, toward the airway. The presence of the rigid or semi-rigid scaffold 138 will stiffen tissue structures in, on, or near the floor of the mouth, thereby resisting their displacement toward the airway. In this way, the scaffold 138 serves to bias tissue structures against collapse in a cranial direction into the airway. The physical properties of the scaffold 138 should be moderated so that presence of the scaffold 138 does not cause posterior motion of the hyoid with mandible motion.

An exterior surface of the scaffold 138 can be roughened to prevent migration within tissue. The roughened surface can comprise, e.g., a microporous surface to prevent migration and/or promote tissue in-growth. In this arrangement, a resorbable suture material can be used to initially stabilize the scaffold 138's position in tissue, until tissue in-growth occurs.

As FIG. 38A shows, more than a single scaffold 138 may be placed within a targeted tissue region in, near, or on the floor of the mouth. For example, as shown in FIG. 38A, three scaffolds 138a, 138b, and 138b, each having a width of about 3 mm can be placed in along the anterior-to-posterior distance of the tissue region, for a composite width of about 10 mm. Thus, a plurality of scaffolds 138 of lesser width (e.g., 1 mm to 3 mm) can be implanted in tandem to create wider transverse array of scaffolds. As FIG. 38B shows, the position of scaffolds 138 can also be staggered along the anterior-to-posterior distance, forming an anterior-to-posterior array 140 of scaffolds 138(1) to 138(7). The number of scaffolds 138 (n), and thus the composite transverse width and anterior-to-posterior length of the array vary. The array 140 of scaffolds can increase in width in an anterior-to-posterior direction (as FIG. 38B shows), so that the anterior width of the array (e.g., 10 mm to 20 mm) increases to a greater posterior width (e.g., 20 mm to 30 mm), providing with multiple scaffolds a trapezoid shaped array. An array of scaffolds, if desired, can extend in a transverse orientation (as FIG. 38C shows), or in an oblique orientation (as FIG. 38D shows), or in combinations of anterior-to-posterior, transverse, and/or oblique orientations.

2. Preferential Bending Characteristic

First Representative Embodiment

FIGS. 39A/B/C/D/E show another representative embodiment for a scaffold 138. In this embodiment, the scaffold 138 comprises a rigid or semi-rigid core body 142 formed from a polymer material. The core body 142 is trapezoidal in shape in plane view (along its anterior-to-posterior axis, as FIG. 39B best shows), having an anterior region 144 that is narrower than its posterior region 146. A representative width for the anterior region 144 ranges between about 10 mm to about 20 mm. A representative width for the posterior region 146 ranges between about 20 mm to 30 mm. The longitudinal taper in an anterior to posterior direction serves to resists migration of the scaffold 138 when implanted.

A surface 148 of the core body 142 is interrupted with spaced-apart areas of reduced thickness arranged in intersecting crossing patterns. As best shown in FIG. 39B, these patterns form an array of bumps 150 separated by flexible hinges 152 along this surface 148. The pattern does not extend to the other surface 156 of the core body 142, as FIG. 39A best shows.

The hinges 152 form regions of reduced thickness on the surface 148 of the core body 142. The hinges 152, being on one side 148 of the core body 142 and not the other side 156, impart preferential flexibility to the core body 142 of the scaffold 138 in one direction. Due to the purposeful pattern of bumps 150 and hinges 152 on the side 148, when subject to compression, the scaffold 138 will bend easier in a first direction outward in the direction of the side 148 (as shown in FIG. 39E) than in the opposite second direction outward in the direction of the side 156. This is because the hinged bumps 150 contact and interfere to prevent bending in the second direction, but open and do not interfere when bending in the first direction occurs (as FIG. 39E shows). A flexible material 154 encases the entire core body 142, as FIGS. 39D and 39E show, enclosing the bumps 150 and hinges 152, so that tissue does not enter into and be pinched within the hinges 152 during flexure.

Figure 40:
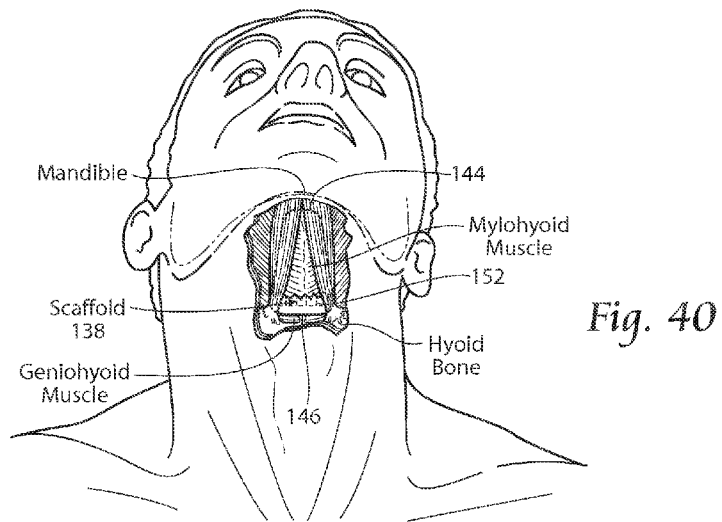
Figure 41A:
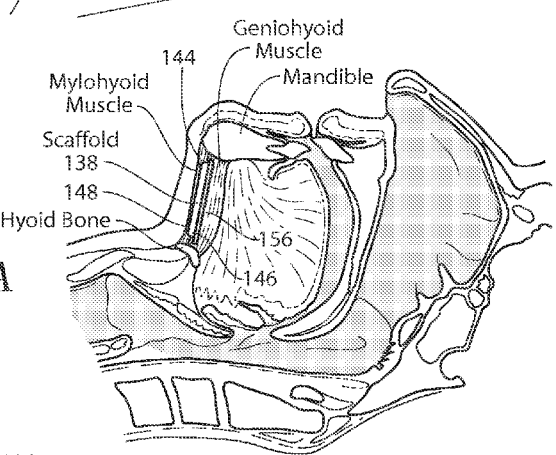
FIGS. 41A and 41B are anatomic side section views of the oral cavity of an adult human in a supine sleep position, the mouth being closed in FIG. 41A and being opened in FIG. 41B annotated to show the scaffold shown in FIGS. 39A/B/C/D/E functioning to mechanically support tissue structures in, on, or near the floor of the mouth and affirmatively resist their movement into an airway, FIG. 41B also showing the preferential bending feature of the scaffold.

In use (see FIGS. 40 and 41A), the scaffold 138 is implanted in a tissue structure in, on, or near the floor of the mouth. When implanted, the scaffold 138 is oriented with the narrower anterior region 144 facing the mandible and the wider posterior region 146 facing the hyoid bone (see FIGS. 40 and 41A). When implanted, the hinged bumped surface 148 of the scaffold 138 is oriented toward the feet, i.e., in a caudal direction, as FIGS. 40 and 41A also show.

The presence of the scaffold 138 (which is less flexible than tissue) braces tissue structures in, on, or near the floor of the mouth. Further, compression of the scaffold 138 will occur in response to compression of tissue structures in the floor of the mouth between the mandible and hyoid. As FIG. 41B shows, the tissue structures will be compressed, e.g., in response to opening the mouth, or posterior translation of the mandible.

The tissue structures are compressed when this occurs, because the anterior-to-posterior distance between the hyoid and the mandible shortens.

Figure 41B:
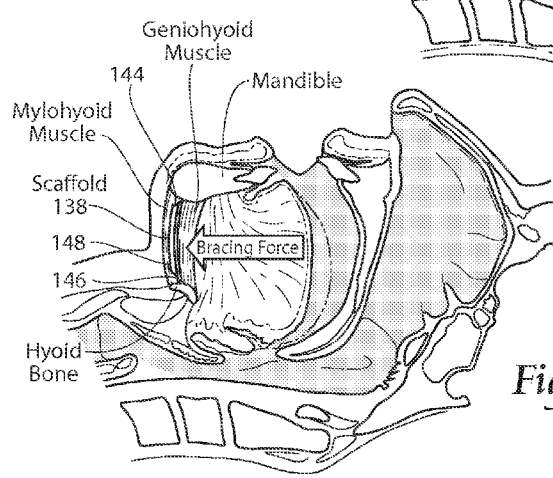

When compressed, the scaffold 138 responds by preferentially bending in a caudal direction (as FIG. 41B shows). In this way, the scaffold 138 serves to dynamically brace or bias the tissue structures against collapse in a cranial direction into the airway.

A scaffold 138 can, if desired, be made from a flexible material with a spring constant. This scaffold 138, when bent, will impart an active spring force in the desired caudal direction. However, as shown in FIGS. 39A to 39E, a rigid or semi-rigid structure, not having a spring constant per se, can be used, if it is preferably weakened to provide the preferential bending characteristics desired (as FIG. 39E shows).

Further, the preferential bending of the scaffold 138 can affirmatively restrict mandibular motion. However, even without affirmatively restricting mandibular motion, the scaffold 138 can nevertheless respond to mandibular motion in a beneficial way, to force compressed tissue in the floor of the mouth to bend out (away from the floor of the mouth), rather than bend inward toward the airway (which is its native inclination, which is further assisted by the force of gravity when the individual is in a sleeping position).

Representative Embodiments with Tissue Stabilization

Figure 42:
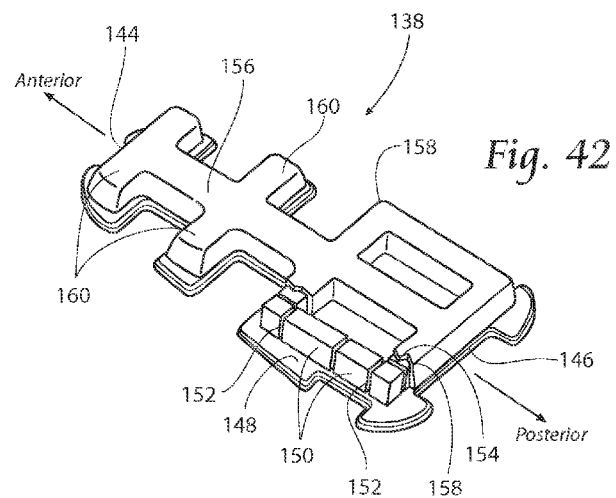
FIGS. 42 and 43 are perspective views of a representative embodiment of a scaffold like that shown in FIGS. 39A/B/C/D/E and 40, and further including features that help stabilize the scaffold in tissue.
Figure 43:
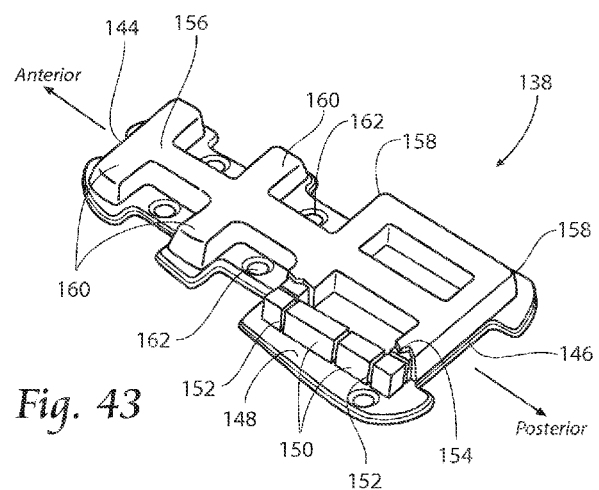

FIGS. 42 and 43 show other representative configurations for a scaffold 138 having a preferential bending property. The scaffolds 138 shown in FIGS. 42 and 43 comprise generally the same structural features that impart preferential bending as shown in FIGS. 39A to 39D (the bumps 150 and hinges 152 are covered by flexible material 154, as shown in cut-away section in FIGS. 42 and 43). In FIG. 42, the scaffold 138 further includes contoured edges 158 and extended "wings" 160 for enhanced stabilization in tissue. In FIG. 43, the scaffold 138 further includes through-holes 162 for tissue in growth and enhanced, long term tissue stabilization. Stabilization in tissue resists migration of the scaffold 138 when implanted.

Another Representative Embodiment

Figure 44A:
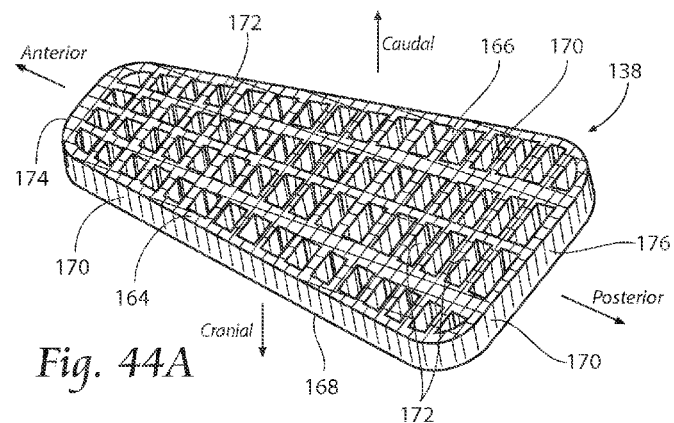
FIGS. 44A/B/C/D/E and 45 are views of a representative embodiment of a scaffold sized and configured for implantation in, on, or near tissue structures in the floor of the mouth having a preferential bending feature that mechanically supports the tissue structures in a desired orientation and affirmatively resist their movement into an airway.
Figure 44B:
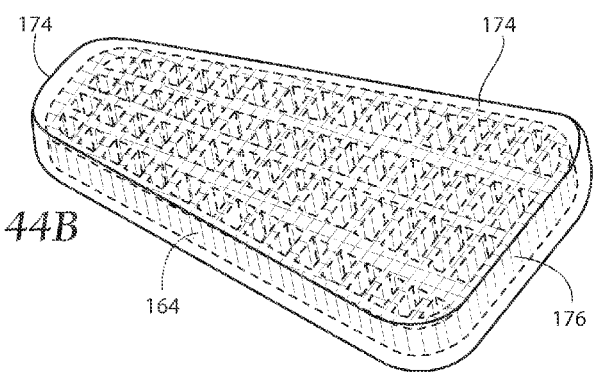
Figure 44C:
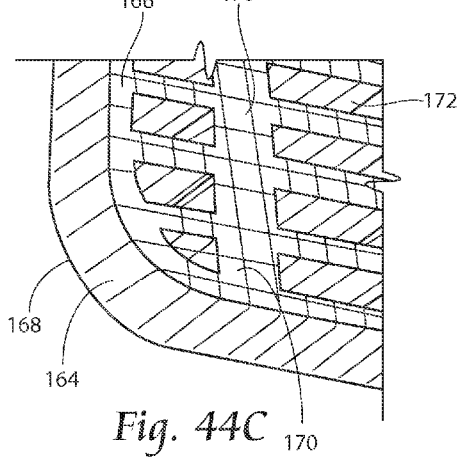
Figure 44D:
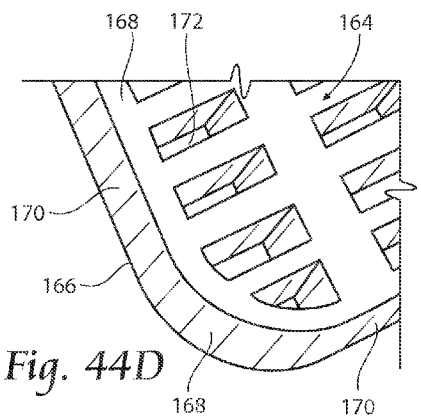

FIGS. 44A/B/C/D/E/F show another representative scaffold 138 having preferential bending characteristics. As shown in FIG. 44A, the scaffold 138 comprises a core body 164 formed from a metal or polymer material. The core body 164 is trapezoidal in shape in plane view (along its anterior-to-posterior axis, as FIG. 44A best shows), having an anterior region 174 that is narrower than its posterior region 176. The core body 164 includes opposite facing surfaces 166 (shown in enlarged view in FIG. 44C) and 168 (shown in enlarged view in FIG. 44D). The surface 166 includes a pattern of spaced-apart cuts 170 that extend uniformly into the core body 164 (see FIGS. 44A and 44C), along and across the longitudinal axis of the core body 164. Each cut 170 is thin and does not extend all the way through the material of the core body 164 to the other surface 168 (as FIG. 44D shows). A thin, continuous uncut layer of material remains along the surface 168 of the body, as FIG. 44D shows. Thus, the surface 166 of the core body 164 is slotted and weakened by the cuts 170, and the other surface 168 is not.

Figure 44E:
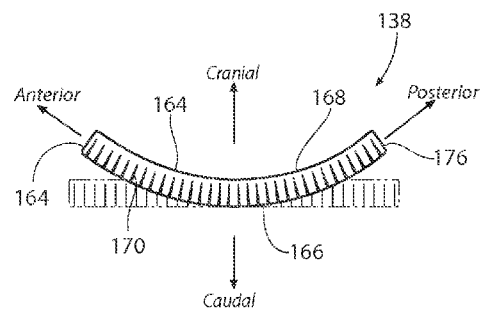

The pattern of cuts 170 preferentially weakens the core body along the surface 166. The slotted surface accommodates preferential bending of the core body 164 in a direction that opens the cuts, the continuous layer 168 flexing at an array of flexible hinge points between the cuts 170. The core body 164 will flex between anterior to posterior ends in a direction toward the slotted surface 166, as FIG. 44E shows. The core body 164 will also flex between side edges in the same direction toward the slotted surface 166, as FIG. 44F shows. The cuts 170 close and interfere to resist bending of the body in the opposite direction toward the continuous surface 168.

As FIG. 44A shows, the core body 164 desirably includes a pattern of large through holes 172 extending through the core body 164, which also serves to reduce the overall stiffness of the core body 164. As FIG. 44B shows, polymer material 174, e.g., silicone or urethane, encases the core body 164 and through holes 172 to protect surrounding tissue during bending.

Figure 45:
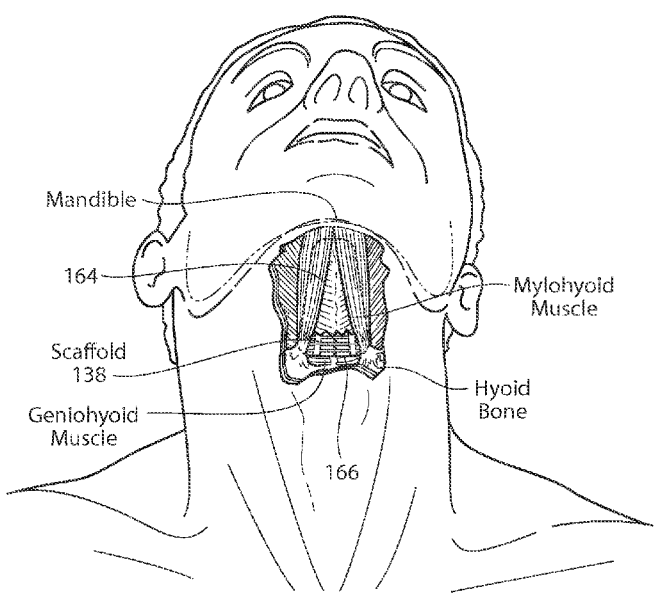

In use (see FIG. 45), the slotted scaffold 138 is implanted in a tissue structure in, on, or near the floor of the mouth with the longitudinal axis oriented along the anterior-to-posterior direction. The narrower anterior end 174 faces the mandible, and the wider posterior end 176 faces the hyoid bone. The continuous surface 168 is oriented in a cranial direction toward the roof of the mouth (i.e., the slotted surface 168 faces the caudal direction), as is also shown in FIGS. 44E and 44F. The presence of the scaffold 138 (which is less flexible than tissue) braces tissue structures in, on, or near the floor of the mouth. Further, as earlier explained, compression of the scaffold 138 will occur in response to compression of the tissue structures in, on, or near the floor of the mouth. When compressed, the slotted scaffold 138 responds by preferentially bending caudally (as FIGS. 44E and 44F show). In this way, the slotted scaffold 138 serves to bias tissue structures against collapse in a cranial direction into the airway.

Another Representative Embodiment

Figure 46A:
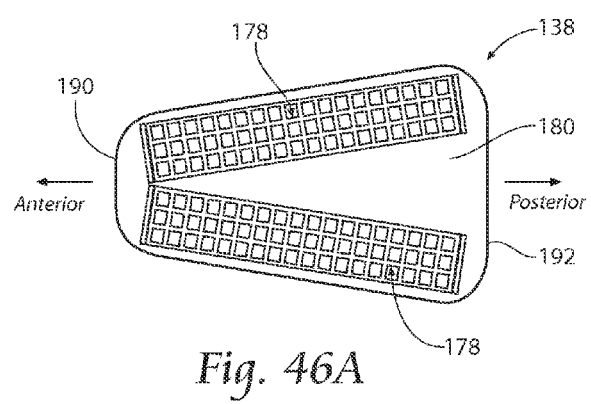
FIGS. 46A/B/C/D/E and 47 are views of a representative embodiment of a scaffold sized and configured for implantation in, on, or near tissue structures in the floor of the mouth having a preferential bending feature that mechanically supports the tissue structures in a desired orientation and affirmatively resist their movement into an airway.

FIGS. 46A/B/C/D/E and 47 show another representative embodiment of a scaffold 138 having a preferential bending property. In this embodiment (see FIG. 46A), the scaffold 138 includes two or more bar assemblies 178 (either metal or polymer) encapsulated within a soft, flexible polymer material 180.

Figure 46B:
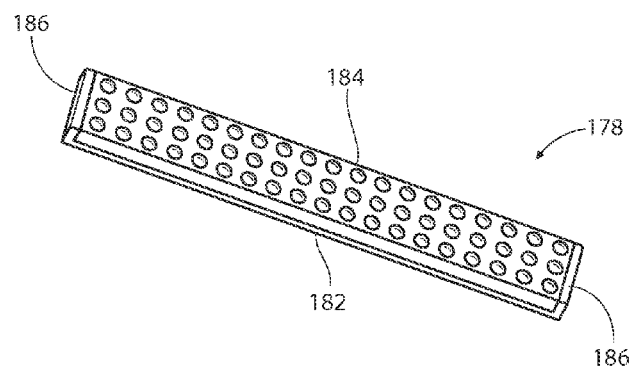
Figure 46C:
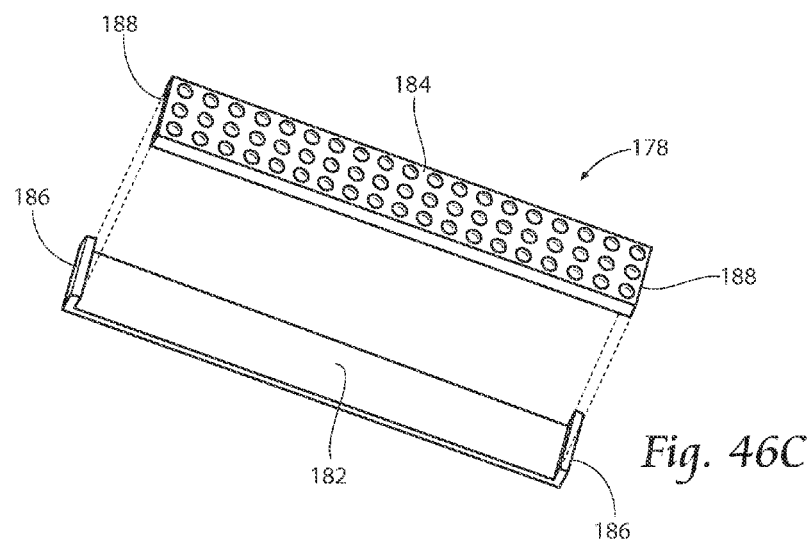

As shown in FIGS. 46B and 46C, each bar assembly 178 comprises a flexible seat 182 and a flexible core element 184. The seat 182 includes uplifted seat end regions 186. The flexible core element 184 releasably nests within the seat 182, with the ends 188 of each core element 184 frictionally in registry with the uplifted seat end regions 186 (see FIGS. 46B and 46D). The nested configuration can be sized and configured to offer yieldable frictional resistance to the separation of the core element 184 from the seat 182. The soft polymer material 180 encapsulates the each bar assembly 178 with the core element 184 nested in the seat 182.

In this arrangement (see FIG. 46D), when a given bar assembly 178 is bent to a first direction that compresses the uplifted seat end regions 186 against the ends 188 of the core element 184, the seat 182 and the core element 184 interfere as a mechanically connected unit to offer resistance to bending in this direction. When the bar assembly 178 is bent in an opposite, second direction (see FIG. 46E), the uplifted seat end regions 186 move away from the ends 188 of the core element 184. The seat 182 and the core element 184 do not interfere, and instead bend separately. Because it is easier to bend thin stacked bars (when the ends are free, as shown in FIG. 46E) rather than bend one thick bar (as shown in FIG. 46D), the bar assembly 178 offers less resistance to bending in the second direction, shown in FIG. 46E.

In the illustrated embodiment (see FIG. 46A), when the bar assemblies 178 are encapsulated by the soft polymer material 180, the scaffold 138 is trapezoidal in shape in plane view (looking toward the feet), having an anterior region 190 that is narrower than its posterior region 192, when implanted. The bar assemblies 178 are confined within the soft polymer material 180, with the seat 182 of each bar assembly oriented in the same plane, to provide preferential bending of the scaffold 138 according to the bending characteristics just described.

In use (see FIG. 47), the scaffold 138 is implanted in a tissue structure in, on, or near the floor of the mouth with anterior region 190 oriented in an anterior direction, i.e., facing the mandible. The scaffold 138 is also oriented with the seats 182 of the bar assemblies 178 oriented in a cranial direction, toward the roof of the mouth (as FIG. 46E indicates). When compression force tries to bend the scaffold 138, the uplifted seat end regions 186 of the bar assemblies 178 are compressed against the ends 188 of the respective core elements 184, provide rigidity to the bar assembly 178 in this bend direction, thereby resisting tissue movement into the oral cavity (i.e., in a cranial direction). The bar assemblies 178 provide preferential flexibility in the opposite, caudal direction, away from the oral cavity, as FIG. 46E shows. The scaffold 138 thereby provide a preferential bias or bracing to tissue in a caudal direction, The scaffold 138 may incorporate on/off activation of preferential bending or stiffening. In this way, the scaffold 138 may be "activated" by external means to be stiffer or shaped at night. For example, by manipulating tissue under the chin, pressure can be applied to a preferential bending mechanism incorporated in the implant, to shape the scaffold 138 in the preferentially bent condition (i.e., caudal orientation) prior to sleep. Conversely, manipulation of tissue under the chin can return the scaffold 138 in a neutral orientation during the day. Desirably, the preferential bending mechanism provides an audible indication (e.g., a "click") when the desired orientation is assumed. Alternatively, preferential bending can be activated by electrical, RF, magnetic, or temperature means. The scaffold 138 can include shape memory material or a shape activated material.

Desirably, the seat 182 and the core element 184 of each bar assembly 178 possess essentially the same stiffness. In this way, the preferential bend characteristics of bar assemblies within a given scaffold 138 can be can balanced and controlled. In another arrangement, the core element 184 may comprise a plurality of thinner and less stiff bending elements, which can be assembled as desired to achieve targeted preferential bending characteristics.

Another Representative Embodiment

Figure 48:
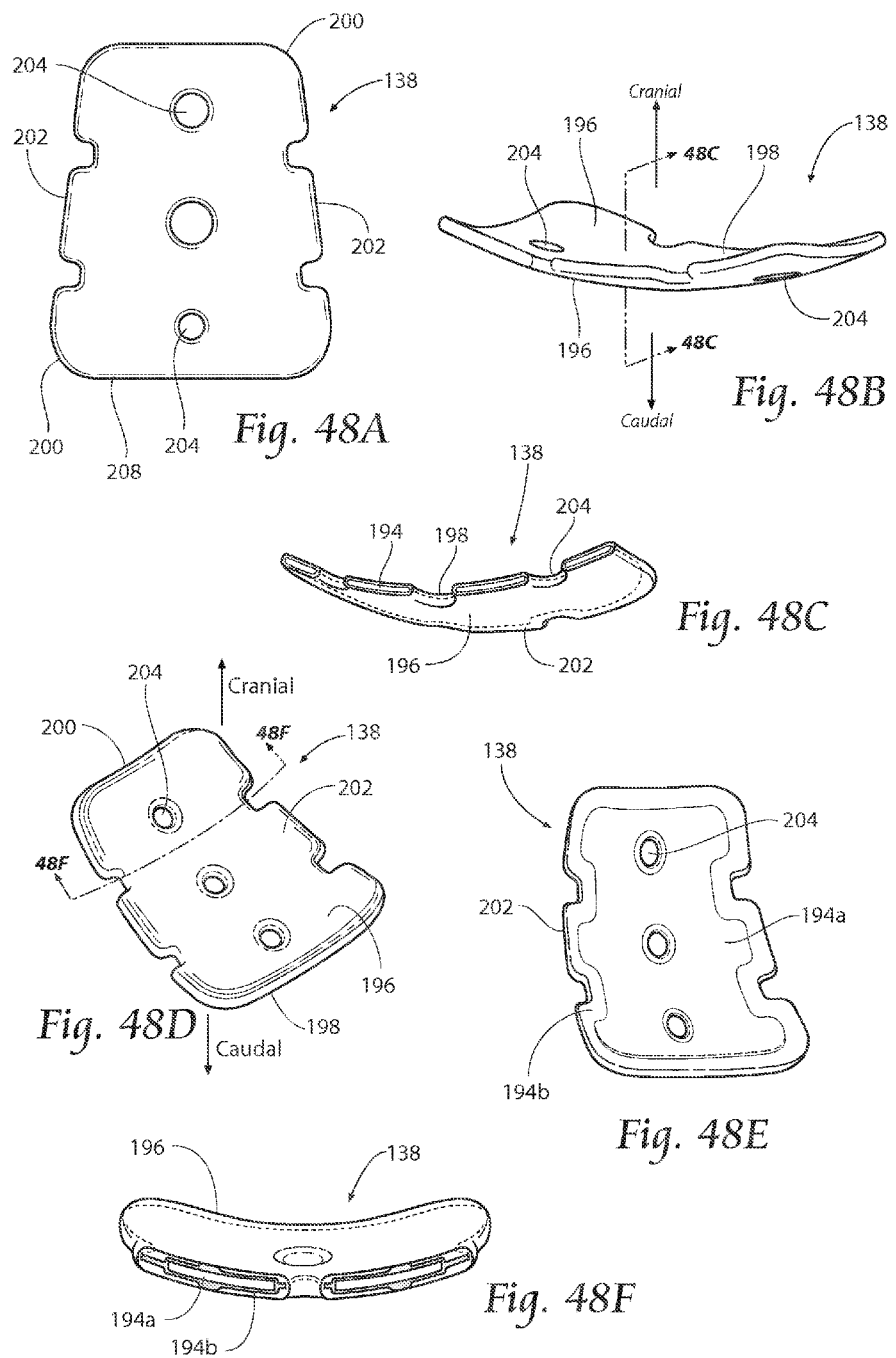
FIGS. 48A/B/C/D/E/F and 49 are views of a representative embodiment of a scaffold sized and configured for implantation in, on, or near tissue structures in the floor of the mouth having a preferential bending feature that mechanically supports the tissue structures in a desired orientation and affirmatively resist their movement into an airway.

FIGS. 48A/B/C show another representative embodiment of a scaffold 138 that provides a preferential orientation to tissue structures in, on, or near the floor of the mouth.

In this embodiment, the scaffold 138 includes a core body 194 (see FIG. 48C) comprising a first polymer material encapsulated in a second polymer material 196. The core body 194 is preformed with surfaces curved in both directions (length and width), forming a saddle-shaped structure (best shown in FIG. 48B). The saddle-shape structure includes a convex curving surface 196 and an inverse concave curving surface 198. The first polymer material of the core body 194 is rigid or semi-rigid and possesses enough stiffness to maintain the desired saddle-shape configuration. The second polymer material 196, which encapsulates the core body 194, is less stiff to provide a non-traumatic interface with surrounding tissue.

As shown in FIG. 48A, the scaffold 138 can include contoured edges 200 and/or extended "wings" 202 for stabilization. The scaffold 138 can also include through-holes 204 for tissue in growth and long term tissue stabilization. Desirably, the core body 194 is also trapezoidal in shape in plane view (looking, toward the feet), as FIG. 48A shows, having an anterior region 206 that is more narrow than the posterior region 208, when implanted.

Figure 49:
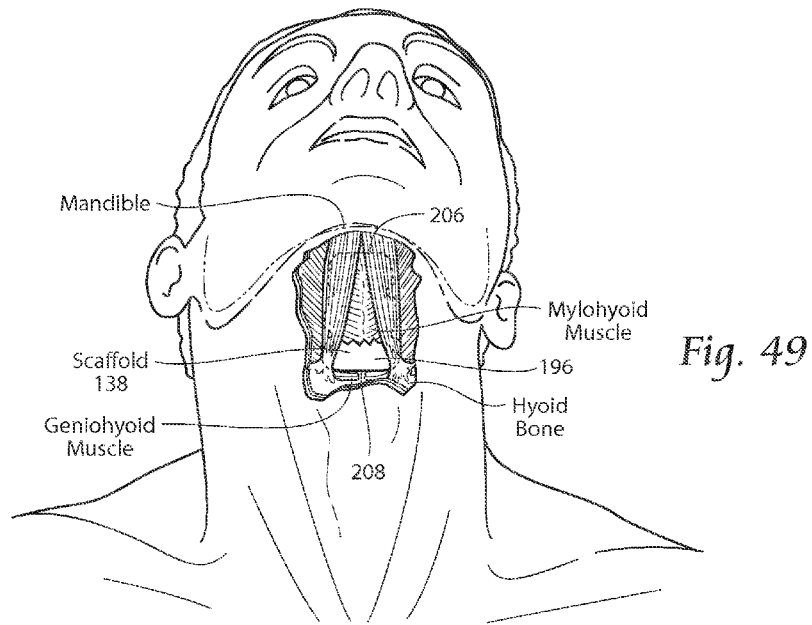

For use (see FIG. 49), the scaffold 138 is implanted in a tissue structure in, on, or near the floor of the mouth with the anterior region 206 oriented in an anterior direction toward the mandible. The scaffold 138 is also oriented with the convex curve configuration 196 oriented toward the feet. The scaffold 138 therefore provides a preferential bias or bracing to tissue in a caudal direction.

FIGS. 48D, 48E, and 48F illustrate another embodiment of a scaffold 138 that includes a core body 194 comprising a first polymer material encapsulated in a second polymer material 196. In this embodiment, the core body 194 includes a semi-rigid mesh 194A comprising, e.g., a nitinol material, as FIG. 48E best shows. As further shown in FIG. 48F, the core body 194 further includes an interface 194B (comprising, e.g., silicone and fabric) that adheres to the mesh material 194A. The interface 194B provides a durable transition to the outer layer of the second polymer material 196, which encapsulates the core body 194 and can comprise, e.g., silicone to provide a flexible interface with soft tissue. The semi-rigid core mesh 194A and overlaying fabric interface 194B provide resistance to plastic deformation during use.

As previously described, the core body 194 is preformed with surfaces curved in both directions (length and width), forming a saddle-shaped structure (best shown in FIG. 48D). The saddle-shape structure includes a convex curving surface 196 and an inverse concave curving surface 198. The first polymer material of the core body 194 is rigid or semi-rigid and possesses enough stiffness to maintain the desired saddle-shape configuration. The second polymer material 196, which encapsulates the core body 194, is less stiff to provide a non-traumatic interface with surrounding tissue.

As shown in FIG. 48A, the scaffold 138 can include contoured edges 200 and/or extended "wings" 202 for stabilization. The scaffold 138 can also include through-holes 204 for tissue in growth and long term tissue stabilization.

3. Representative Implantation Methods

A representative method for implanting a scaffold 138 like that shown in FIG. 34B includes making a transverse superficial incision under the chin, desirably along the natural chin fold. The method includes cutting platysma muscle to provide access to the mylohyoid muscle. Access to the mylohyoid muscle can be obtained between the two digastrics muscles, which do not need to be cut. The method includes cutting and dissecting the mylohyoid muscle between the digastric muscles to gain access to the muscle plane between the mylohyoid and geniohyoid muscles.

The method includes placing the scaffold 138 in this plane so that the thin dimension of the scaffold 138 is in the superior/inferior direction, with the length and width of the scaffold 138 extending in the lateral as well as anterior/posterior directions.

The method can optionally suturing the implant to surrounding tissue as desired for stabilization. The most desired location for suturing is around the hyoid or to the connective tissue attached to the hyoid. The scaffold 138 body may have an extension into the genioglossus for additional stabilization of the scaffold 138 body, as well as provide stabilization for the genioglossus itself. As before explained, the scaffold 138, if desired, may be attached to one or both of the rigid bone structures of the mandible and hyoid bone, e.g., by screws, suture, or clamping, as previously shown in FIG. 34D.

The method includes suturing the mylohyoid and platysma muscles closed, and then closing the superficial skin incision.

Figure 50A:
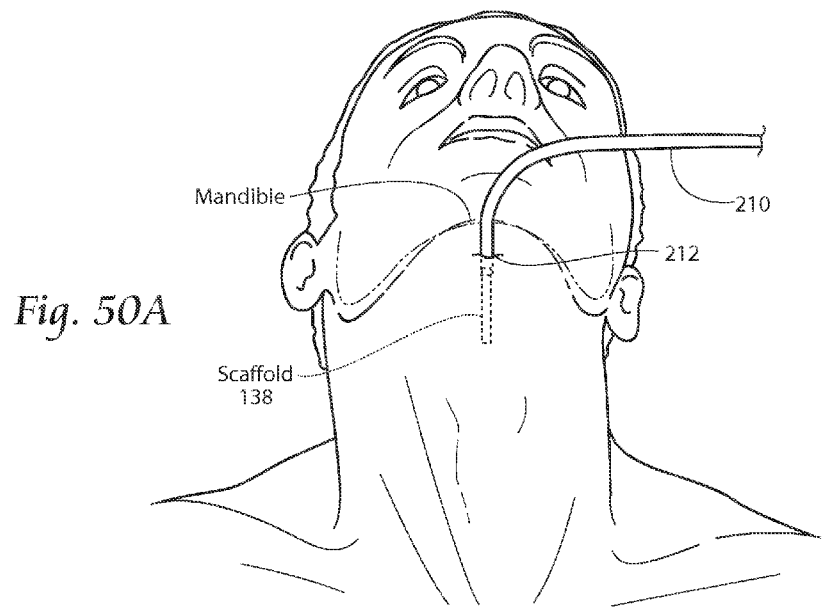
FIG. 50A is an anatomic anterior view of an individual, showing the non-invasive implantation of a scaffold like that shown in FIGS. 34A/B/C and 36/37 through a percutaneous delivery assembly.
Figure 50B:
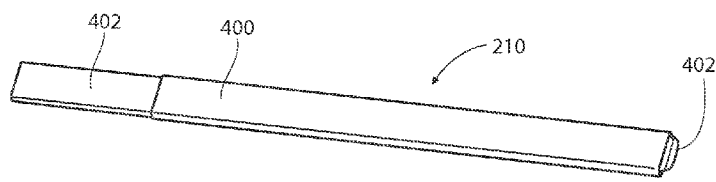
FIGS. 50B, 50C, 50D, and 50E are a sequence of views showing the manipulation of the delivery assembly shown in FIG. 50A to deliver a scaffold into tissue in the floor of the mouth.
Figure 50C:
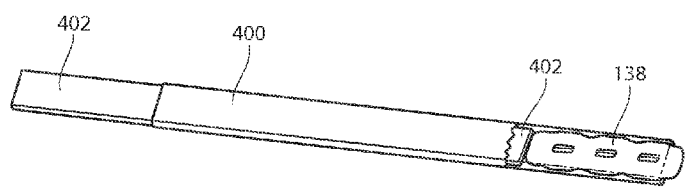
Figure 50D:
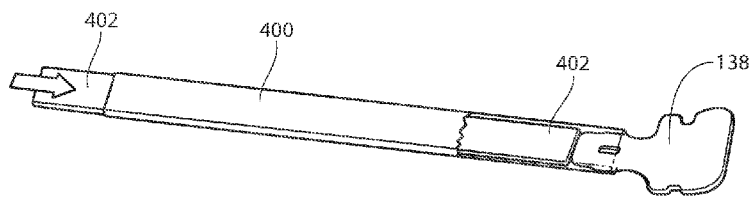
Figure 50E:
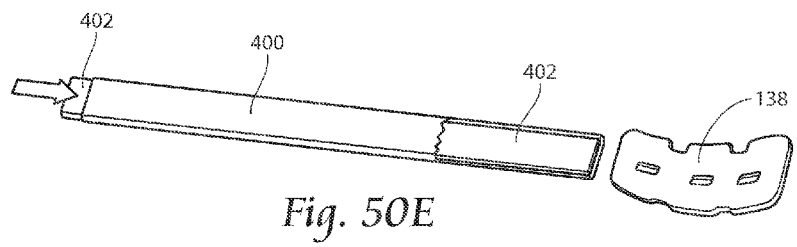

The scaffold 138 can, alternatively, be implanted using a minimally invasive method including trocar, and/or needle and/or endoscopic delivery of the scaffold 138 through a delivery assembly 210 (see FIG. 50A) that is percutaneously inserted through a small incision 212. As FIG. 50B shows, in a representative embodiment, the delivery assembly 210 includes a cannula 400 and stylet 402 that can be advanced through the cannula 400. As FIG. 50C shows, the scaffold 138 is collapsible and can be maintained in a collapsed condition within the distal end of the cannula 400 for percutaneous delivery, as FIG. 50A also shows. Advancing the stylet 402 in the cannula 400 urges the scaffold 138 from the distal end of the cannula 400, as FIG. 50D shows. The scaffold 138 self-expands, as FIG. 50E shows, for placement on and fixation in a pocket formed within a natural tissue plane in the floor of the mouth, e.g., between geniohyoid and mylohyoid muscle planes. Natural boundaries of muscle fascia, the hyoid bone, and the mandible provide stability for the implanted scaffold 138. Alternatively, the hyoid bone and the mandible can provide fixation sites for the scaffold 138, as previously described.

The procedure is minimally invasive and does not require high skill or surgical experience. It can be performed under local or general anesthesia or conscious sedation, without fluoroscopy or other imaging modality in a short period of time, e.g., within ten minutes. Implantation of the scaffold 138 is completely and quickly reversible.

In an alternative embodiment, the scaffold 138 can comprise a hollow body that can be filled with fluid or otherwise stiffened after placement.

4. External Scaffolds and Combinations

As previously described, diverse tissue structures occupy the neck, the pharyngeal airway, and floor of the mouth, comprising layers of dermis, fat, and muscle, which are mutually interconnected from the epidermis inward to the tongue and base of the tongue. An adhesive brace or collar 102 has been described for placement in association with tissue of the neck to stabilize and brace these tissue structures against collapse into the airway. Alternatively, scaffolds 138 have been described for implantation in, on, or near tissue structures of the floor of the mouth for the same purpose.

Due to the native, interconnected morphology of tissue structures in this region, one or more scaffolds 138 can be sized and configured for placement in or on epidermal tissue or in dermal tissue along the neck and/or near the floor of the mouth to stabilize and brace these tissue structures against collapse into the airway. The chin support structures, affixed by adhesive materials 104, as previously described, are representative embodiments of external scaffolds 138. As FIG. 51 shows, the scaffolds 138 can also include individual lengths or strips of material affixed by adhesive materials 104 to the external skin along the neck or overlying the floor of the mouth. Preferential bending of these external scaffolds 138 serves to stabilize or bias tissue structure in, on, or near the neck, pharyngeal airway, and the floor of the mouth away from collapse into an airway, in the same manner as implanted scaffolds 138.

As shown in FIGS. 52A and 52B, the scaffold 138 can comprise a formed flexible bracing structure 320. The bracing structure 320 (see FIG. 52A) comprises a pair of spaced apart trusses 322 and an intermediate cross strut 324, which extends across a proximal part of the trusses 322. The cross-strut includes a depression forming a pocket 326. The pocket 326 is sized and configured to receive displaced tissue in, on, or near the floor of the mouth, to avoid compressing the tissue and thereby avoid, during use, interference with the native anchoring function that the floor of the mouth provides to the mandible, hyoid bone, and tongue.

As FIG. 52B shows, the bracing structure 320 can be affixed by adhesive material 328 on epidermal tissue along the neck and/or near the floor of the mouth. As shown in FIG. 52B, the bracing structure 320 is sized and configured, when worn, to fit beneath the chin region, under the floor of the mouth, and the neck region, and extend from there to tissue overlying the larynx. Adhesive material 328 in the pocket 326 holds tissue outward, stabilizing or biasing tissue structures in, on, or near the floor of the mouth away from collapse into an airway, in essentially the same manner as previously described scaffolds.

Further, systems and methods comprising combinations of external and internal (implanted) structures placed in association with a neck and/or the floor of the mouth can also be placed and oriented to stabilize or bias tissue structure in, on, or near the neck, pharyngeal airway, and the floor of the mouth, away from collapse into an airway.

Figure 53A:
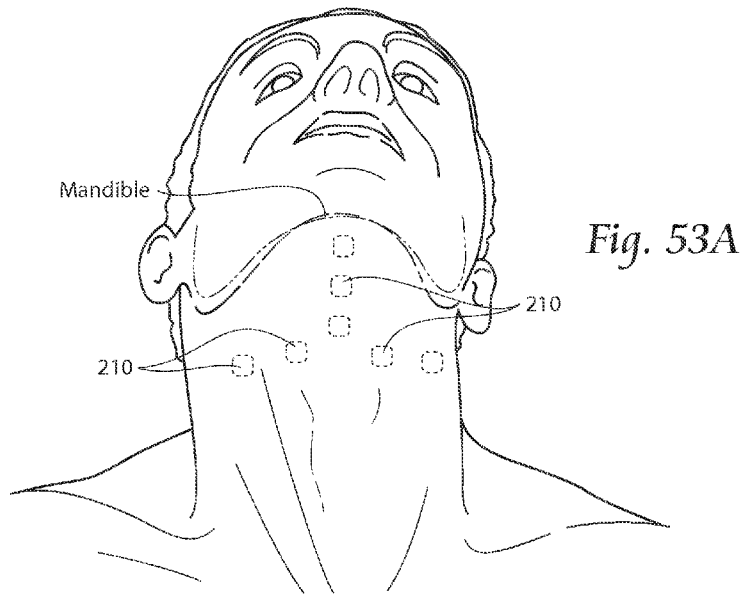
FIGS. 53A and 53B are perspective views and FIG. 53C is an anatomic side section view of a representative embodiment of an apparatus comprising a neck piece and chin support that magnetically interacts with magnets implanted in, on, or near tissue structures in the neck or the floor of the mouth to externally brace tissue structures in, on, or near the neck, and/or along the walls of the pharyngeal airway, and/or the floor of the mouth.
Figure 53B:
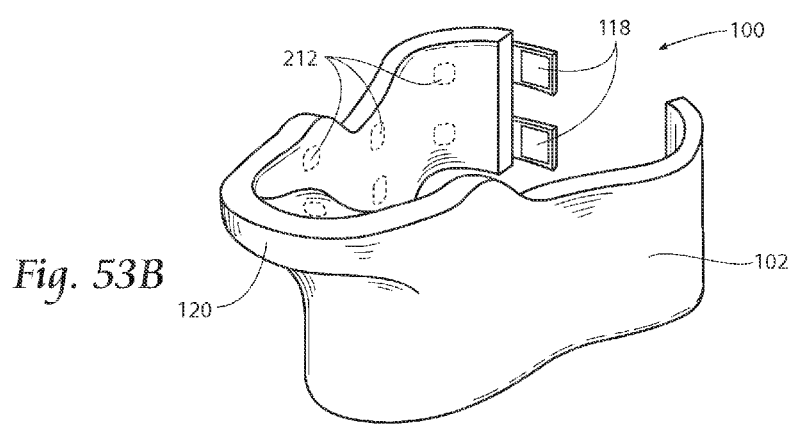
Figure 53C:
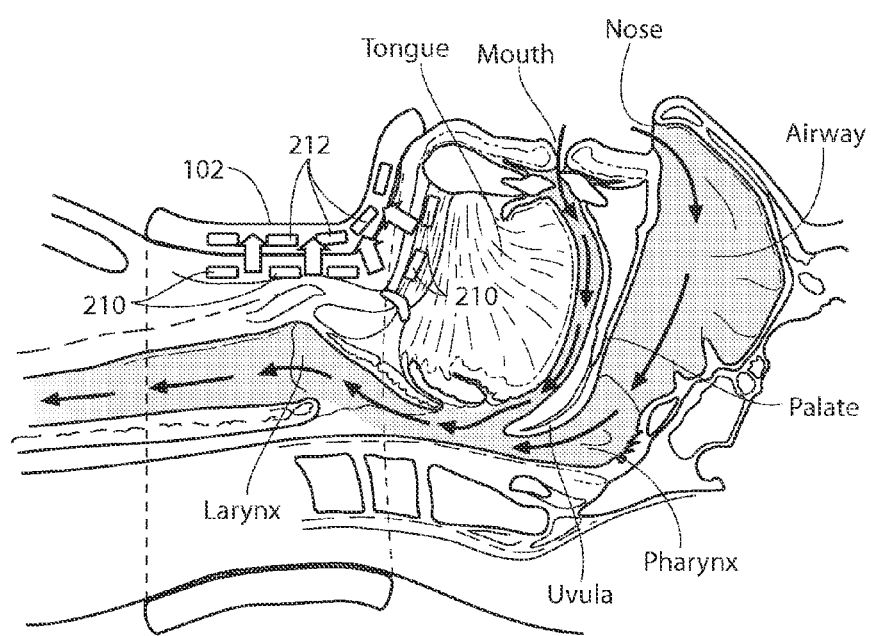

For example, an external brace or collar 102 has been described that is coupled to neck tissue using an adhesive or by negative pressure, to stabilize tissue structures against collapse into an airway. By the same token (see FIGS. 53A/B/C), an external brace or collar 102 can also be coupled to neck tissue by magnetic attraction between one or more external magnets 212 or ferrous materials carried by the brace or collar 102 and one or more magnets 210 or ferrous materials implanted in, on, or near tissue structures of the neck and/or the floor of the mouth. The magnetic attraction between the external magnets 212 or ferrous materials on the brace or collar 102 and the implanted magnets 210 or ferrous materials can exert a stabilizing force on tissue structures in, on, or near the neck, the pharyngeal airway, and the floor of the mouth, with or without the use of adhesion and/or negative pressure (as FIG. 52C shows). The magnetic interaction can mechanically brace and stabilize tissue structures in, on, or near the neck, pharyngeal airway, and/or floor of the mouth and thereby resist movement or collapse of these tissue structures into the airway. The inside circumference of the collar 102 can also be sized relative to the neck to also exert, as a result of the magnetic interaction, a pulling force on tissue structures in, on, or near the neck, the pharyngeal airway, and/or the floor of the mouth. The magnetically produced, outward pulling force can also reshape these tissue structures toward the slightly larger circumference established by the brace or collar 102. The collar 102 preferably includes a concave pocket region 430 under the chin, which receives tissue underlying the floor of the mouth, so that the collar 102 does not, in use, compress the floor of the mouth to block the desirable lowering of the tongue and its beneficial effects upon the airway, as has been described.

VI. Enhanced Anchorage of the Tongue to Muscles in the Floor of the Mouth

Conventional tongue suspension involves placing a small titanium screw in the jaw. A suture (which is attached to the screw) is threaded through the tongue and tightened. The purpose is to hold the tongue in its proper place when a person is sleeping in order to prevent obstruction in the airway. Hyoid suspension is also an adjunctive procedure to treat an obstructive tongue base, in which the suture threaded through the tongue is attached to a screw in the hyoid bone. Different conventional tongue suspension systems are exemplified by the Repose® Bone Screw (Influent Medical/Medtronic); Jackson et al. US 2006/0207612 (Aspire Medical (which includes a spool assembly to tighten and adjust the length and tension of the tether attached to the jaw); Kühnel US 2007/0288057 (which includes an adjustable elastic tether element attached to the jaw); Hegde et al US 2007/0246052 (Pavad Medical) (which implants a deformable electrical element in the tongue that is tethered to the jaw); Sanders US 2007/0261701; 2008/0188947 (Linguaflex) (which tethers a tongue implant to the jaw); and Iancea et al US 2009/0044814 (Phillips) (which anchors a barbed suture in the tongue or extrinsic muscles of the tongue to the jaw.) In all conventional tongue suspension systems, a tongue implant is anchored to a rigid structure such as the mandible or hyoid bone.

It has been discovered that the native, interconnected morphology of muscles in the floor of the mouth, the mandible, and hyoid bone serves as a native anchoring structure for the tongue for tongue suspension.

Figure 54:
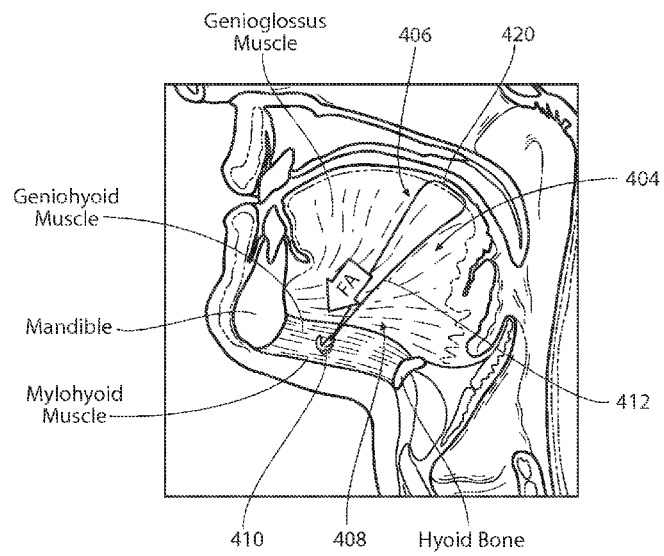
FIGS. 54 to 57 are anatomic side section views of the oral cavity of an adult human showing a tongue suspension structure coupled to an anchor in the floor of the mouth to resist posterior slippage of the tongue into the airway, the anchor comprising a flexible scaffold anchoring structure in FIGS. 55, 56, and 57.
Figure 55:
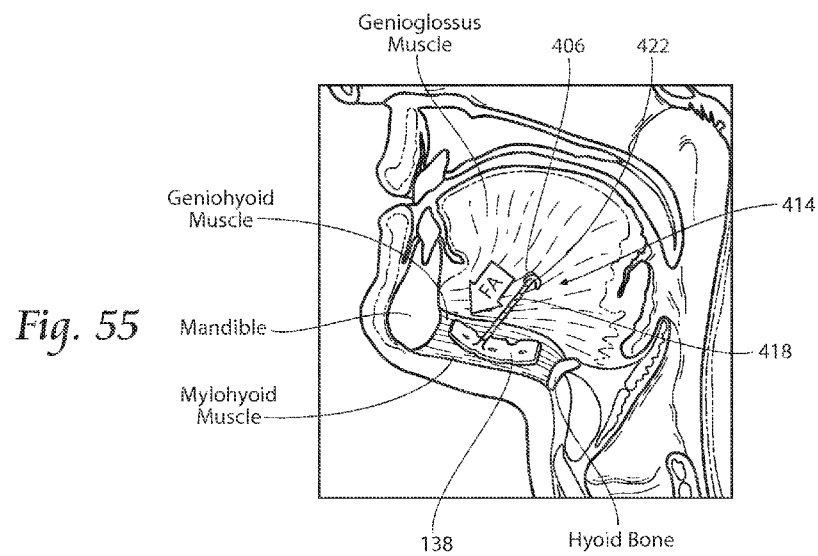
Figure 56:
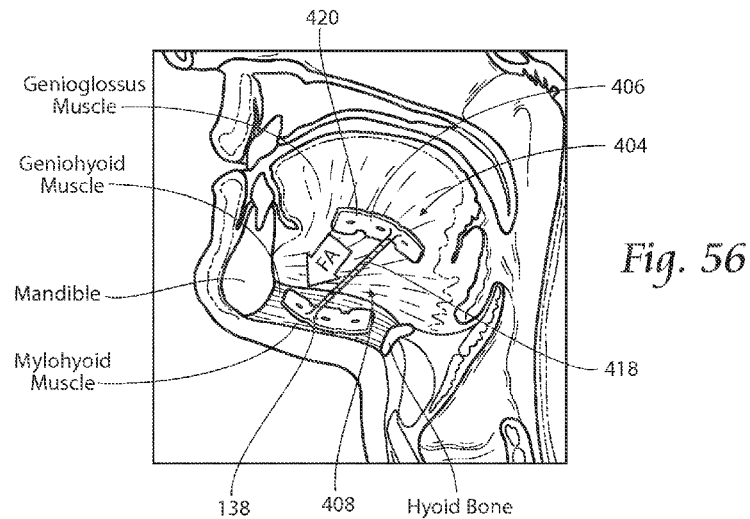
Figure 57:
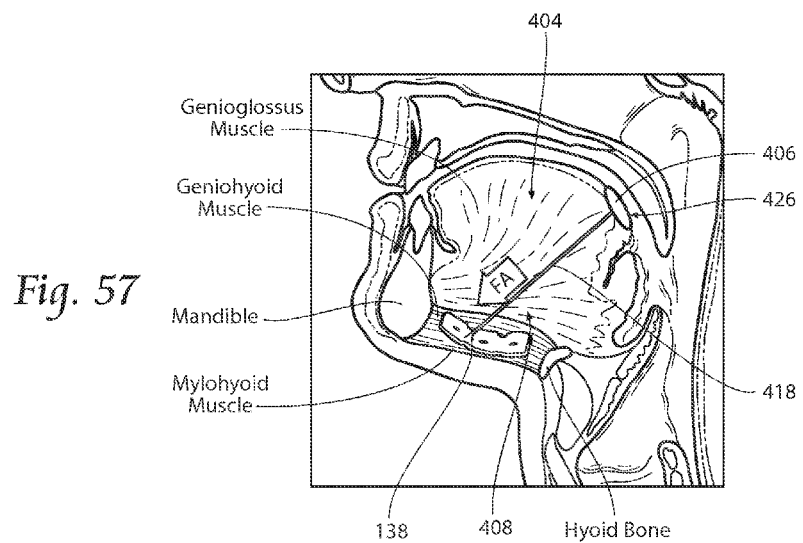

FIGS. 54 to 57 show various tongue suspension systems 404 comprising a tongue suspension structure 406 sized and configured for placement in or on a tongue. The tongue suspension structure 406 can, e.g., comprise a looped suture structure 420 (as FIG. 54 shows). The tongue suspension structure 406 can comprise a pronged tissue implant 422 (as shown in FIG. 55). The tongue suspension structure 406 can comprise a shaped generally flexible body 424 sized and configured to be surgically implanted in the tongue (as shown in FIG. 56). In FIGS. 55 and 56, the body of the tongue suspension structure 406 can comprise a biocompatible metallic or polymer material, or a metallic or polymer material that is suitably coated, impregnated, or otherwise treated with a material to impart biocompatibility, or a combination of such materials. As shown in FIG. 57, the tongue suspension structure 406 comprises a disc-shaped structure 426 placed on external tissue on the posterior region of the tongue. In one arrangement, the disc-shaped tongue suspension structure 426 comprises an expandable balloon.

The tongue suspension systems 404 shown in FIGS. 54 to 57 include an anchoring structure 408 implanted in the floor of the mouth. The anchoring structure 408 tethers the tongue suspension structure 406 to muscle tissue in the floor of the mouth between the mandible and the hyoid bone to exert an anterior force (FA in FIGS. 54 to 56) upon the tongue suspension structure 406. The anterior anchoring force FA draws the tongue forward and resists posterior movement of the tongue into the airway, as can occur during sleep in the manner previously described.

In FIG. 54, the anchoring structure 408 includes a tissue anchor 410 with prongs that engage and otherwise lodge within muscle tissue. Alternatively, or in combination, the tissue anchor 410 can be sutured or adhered to adjoining tissue, to further fixate and stabilize its position in muscle tissue.

In FIGS. 55 to 57, the anchoring structure 408 comprises a flexible scaffold 138 implanted in muscle in the floor of the mouth, as previously described. In this arrangement, the flexible scaffold anchoring structure 138 exerts an anterior force FA upon the tongue to resist posterior movement of the tongue into the airway, as could occur during sleep in the manner previously described. The flexible scaffold anchoring structure 138 can be sutured or adhered to adjoining tongue tissue, to further fixate and stabilize its position in tongue tissue. Of course, the flexible scaffold anchoring structure 138 can be used in place of the tissue anchor 410 shown in FIG. 54, if desired.

In FIGS. 55 to 57, the flexible anchoring scaffold structure 138 is coupled by a tether structure 418 to the tongue structure 406. The tether structure 418 can comprise, e.g., suture or comparable biocompatible string, fiber, coil, or cable material, or nitinol material, or polymer wire, or a bioabsorbable column structure. In FIG. 54, the looped suture structure 420 can be coupled directly to a flexible anchoring scaffold structure 138.

Attaching the tongue suspension structure 406 to a flexible scaffold anchoring structure 138 as shown in FIGS. 55 to 57 in the floor of mouth reduces potential for pull out or failure of attachment points. Importantly, attaching the tongue suspension structure 406 to a flexible scaffold anchoring structure 138 in the floor of mouth moderates the stress on the soft tissues (genioglossus) surrounding the tongue suspension structure 406 and mitigates potential for migration of the tongue suspension structure 406 and thus reduction of the tongue tissue suspension effect over time. A tether structure 418 coupled to a flexible scaffold anchoring structure in the floor of the mouth will not fail like a tether structure coupled to a rigid, unyielding mandible/hyoid bone screw junction. The flexible scaffold anchoring structure in the floor of the mouth provides a supple interface due to the trampoline effect of the floor of the mouth, as previously described. A flexible scaffold anchoring structure 138 provides stress and strain relief that a mandible/hyoid bone screw junction does not. The tongue suspension element 406 will not pull itself out when coupled to a flexible scaffold anchoring structure in the floor of the mouth and is less likely to create a foreign body sensation or interfere with speech or swallowing.

It is desirable that the flexible scaffold anchoring structure 138 in the floor of the mouth comprise a preferentially shaped, downwardly bowed, saddle-like structure, in the manner previously described. The preferential bending of the flexible scaffold anchoring structure bows muscles in the floor of mouth outward, and also pulls the tongue outward at the proper vector in order to increase the volume of the oral cavity without pulling against rigid bone structures, thereby augmenting and enhancing the dynamics of the tongue suspension. The preferentially bent, downwardly bowed, saddle shaped structure also bends as the mandible falls, further displacing the floor of the mouth away from the oral cavity to prevent a resultant closure of the airway, while also further lowering the tongue for the same effect. All in all, the flexible scaffold anchoring structure in the floor of the mouth provides and maintains a proper direction to the tongue suspension vector in the dynamic environment of the oral cavity during sleep.

In one arrangement, the flexible scaffold anchoring structure 138 in the floor of the mouth can be attached with sutures or fasteners to the mandible and hyoid, with a resulting pull out force vector straight out toward the floor of mouth between mandible and hyoid.

The flexible scaffold anchoring structure 138 can be in form of a preshaped implant placed through the oral cavity, or a preshaped implant deployed from under chin, submental area, or oral cavity. The flexible scaffold anchoring structure can comprise a fluid or flowable material that is injected into the floor of the mouth and that stiffens or cures in situ by itself (e.g., by cross-liking) or in response to applied external energy such as light, ultrasound, heat, or radio frequency energy. The flexible scaffold anchoring structure can comprise an inflatable structure.

The flexible scaffold anchoring structure 138 can be made from an elastic material with a selected spring constant (e.g., a spring constant similar to tongue tissue), or deformable and activated upon demand to form the desired preferential bend, as above described, in response to the application of manual pressure, or electrical, thermal, or magnetic energy, or other selectively applied activation means.

Figure 58A:
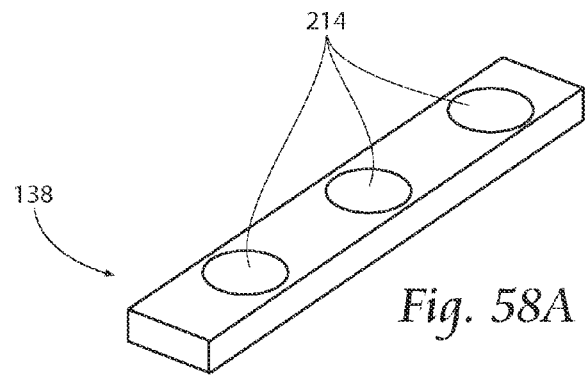
FIG. 58A is a perspective view of a representative embodiment of a flexible scaffold anchoring structure like that shown in FIGS. 55, 56, and 57, but further including an array of magnets or ferrous materials.
Figure 58B:
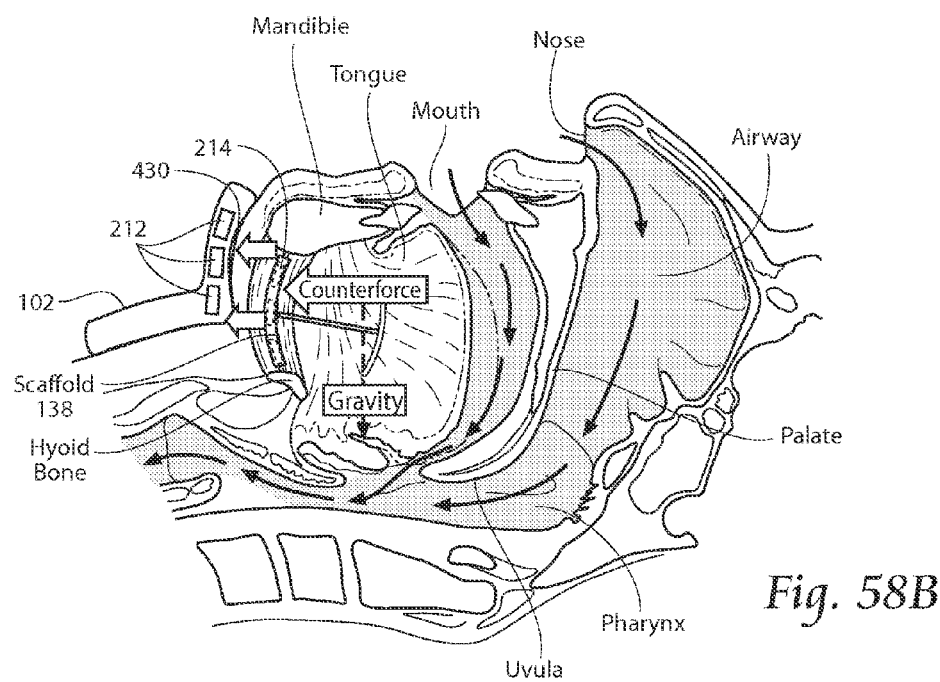
FIG. 58B is an anatomic side section view of the oral cavity of an adult human in a supine sleep position, the mouth being opened, annotated to show the flexible scaffold anchoring shown in FIG. 58A magnetically interacting with an apparatus comprising a neck piece and chin support that preferentially bends the flexible scaffold anchoring structure.

For example, as FIGS. 58A and 58B show, one or more magnets 214 or ferrous materials can be incorporated into a flexible scaffold anchoring structure 138, as previously described. The magnets 214 or ferrous materials can be permanently integrated with or affixed to the flexible scaffold anchoring structure 138 material, or the magnets 214 or ferrous materials can be releasably attached to the flexible scaffold anchoring structure 138 material (to allow removal when desired, e.g., for MRI).

An external array of magnets 212 (e.g., on a chin carrier structure 102) interact with the magnets 214 carried by the flexible scaffold anchoring structure 138 to preferentially bend the flexible scaffold anchoring structure 138 to preferentially bias or brace muscles in the floor of the mouth tissue in a caudal direction, as before described. As before described, the chin carrier structure 102 preferably includes a concave pocket region 430, which receives tissue underlying the floor of the mouth as the scaffold 138 displaces the floor of the mouth away from the oral cavity, so that the chin carrier structure 102 does not compress the floor of the mouth to block the desirable lowering of the tongue and its beneficial effects upon the airway.

Figure 59A:
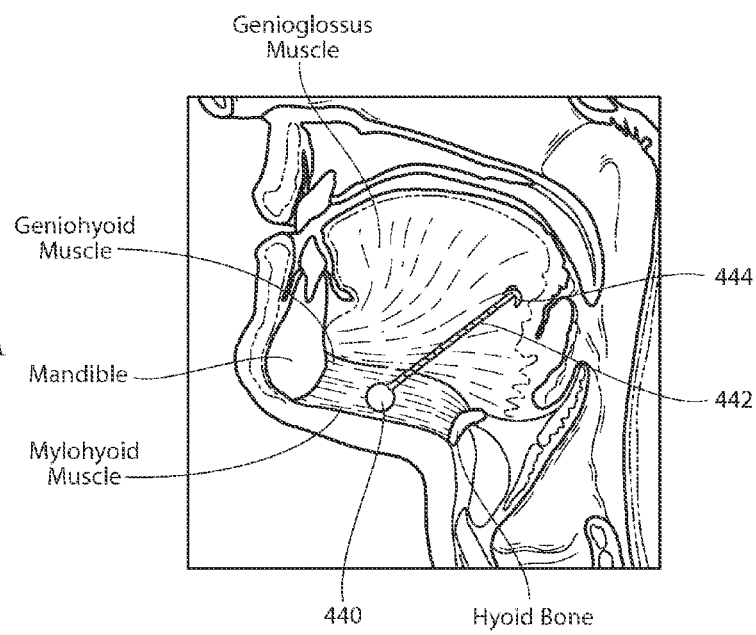
FIGS. 59A and 59B are anatomic side section views of an oral cavity in an adult human showing a magnetically interactive shaped structure placed in the floor of the mouth and tethered to a structure in, on, or near the tongue, being activated by an external magnetic source (see FIG. 59B) to resist posterior slippage of the tongue into the airway.
Figure 59B:
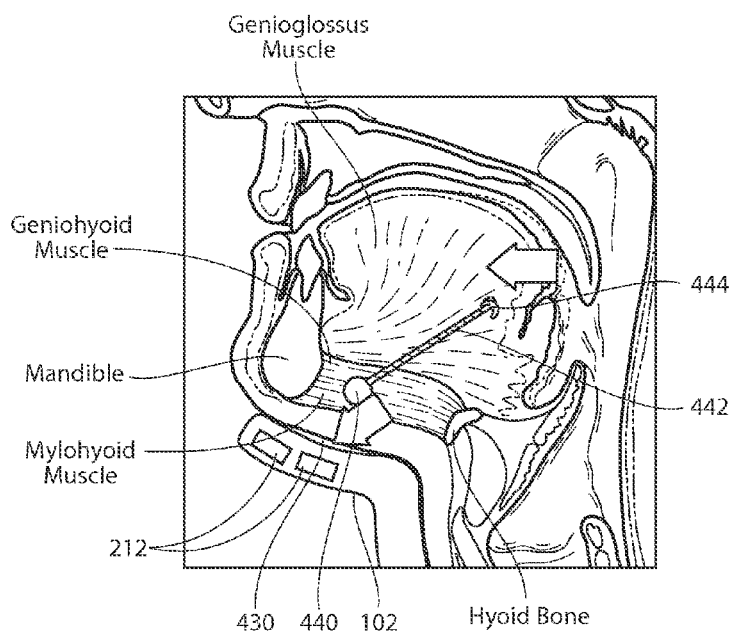

Another embodiment is shown in FIGS. 59A and 59B. In this embodiment, a shaped, magnetically interactive structure 440 made from a magnetic or ferrous material is located in the floor of the mouth. The magnetically interactive structure 440 is coupled by a flexible or semi-flexible tether element 442 to an anchor 444 in the tongue. Alternatively, the magnetic shaped structure 440 can be tethered by the flexible or semi-flexible tether element 442 to a structure 426 like that shown in FIG. 57, placed on external tissue on the posterior region of the tongue. The tether element 442 can be made from a flexible or semi-flexible material, such as suture or comparable biocompatible string, fiber, coil, or cable material, or nitinol material, or polymer wire, or a bioabsorbable column structure.

A corresponding magnet or magnets 212 in an external collar (see FIG. 59B) attracts the magnetically interactive structure 440 to set a magnetic force vector on the anchor 444 in the tongue. The vector pulls forward on the tongue, resisting posterior movement of the tongue toward the airway. The magnet or magnets 212 on the collar can comprise electromagnets or rare earth magnets. The position and strength of the magnets 212 on the collar can be manipulated to change the direction and magnitude of the force vector.

The magnetically interactive structure 440 can be variously sized and configured. It can be spherical (ball shaped), or it may be shaped like a tear drop, or disk, or as a curved scaffold. The surface of the structure is desirably smooth and its overall geometry rounded to allow it to glide or float in tissue. Its position can thereby adjust to external influences. The magnetically interactive, shaped structure 440 is not secured to surrounding muscle and tissue comprising the floor of the mouth. It is thereby able to move or "glide" in the adjacent region of tissue and muscle of the floor of the mouth in response to the externally applied magnetical forces.

The size and configuration of the magnetically interactive structure 440 make possible its implantation in more superficial tissue than the floor of mouth muscles, including regions of subcutaneous fat. This makes the magnetically interactive structure 440 well suited for implantation in people who have greater tissue volumes and subcutaneous fat.

For example, a tear drop shaped structure 440 may be implanted more superficially than the floor of mouth muscles, to occupy a subcutaneous fat region or dermis in the chin, with the apex of the tear drop structure 440 coupled to the tether element 442, which is joined to the anchor 444 in the tongue. The tear drop shape of implant reduces stress at the tether attachment juncture. When subjected to an external force vector by the magnets 212 on the collar, the curved front surface properties of its tear drop shape enable the tear drop structure 440 to float or glide in subcutaneous fat or dermis to assume a position that best aligns with the externally applied magnetic force vector. Being located superficially to the floor of mouth in subcutaneous fat or dermis, the tear drop structure 440 is closer to the external magnetic source to begin with, so force is amplified by the square of the reduced distance. Also being able to float or glide in subcutaneous fat tissue or dermis, the tear drop shaped structure 440 will further seek the closest position to the external magnetic force, increasing force more. By floating and gliding in subcutaneous fat or dermis, the tear drop shape structure 440 can position itself to maximize the magnitude and direction of the force vector. In this way, the force/direction/vector/placed on the tether element 442 and tongue anchor 444 can be titrated and adjusted to achieve improved results and to accommodate changes that may occur over time. The tether element 442 may include a mechanism that allows indexing of tether tension by ratchet, reel, etc., to allow changing the cinch position on the tether element 442 to change its effective length.

As before described, the chin carrier structure 102 on the collar preferably includes a concave pocket region 430, which receives tissue underlying the floor of the mouth as the shaped structure 440 moves in response to magnetic interaction with the external magnets 212, so that the chin carrier structure 102 does not compress the floor of the mouth to block the desirable lowering of the tongue and its beneficial effects upon the airway.

VII. Preferential Bending in Floor of the Mouth with Interaction with Tongue

FIG. 60A(1) shows another representative embodiment for a scaffold 138 comprising a rigid or semi-rigid core body 500 formed from a polymer material. A region 510 of the surface 502 includes a pattern of spaced-apart cuts 504 that extend uniformly into the core body 500. Each cut 504 is thin and does not extend all the way through the material of the core body 500 to the other surface 506 (see also FIGS. 60B and 60C). A thin, continuous uncut layer of material remains along the surface 506 of the body. Thus, the surface 502 of the core body 500 is slotted and weakened by the cuts 502, and the other surface 506 is not.

The pattern of cuts 504 preferentially weakens the core body along the region 510, forming a hinge. The core body 500 will pivot about the hinge 510 (see FIGS. 60B and 60C) in a direction toward the continuous surface 506. The cuts 504 close and interfere to resist bending of the body in the opposite direction toward the slotted surface 502. That is, due to the hinge 510, when subject to compression, the scaffold 138 will bend easier in a first direction outward in the direction of the side 506 than in the opposite second direction outward in the direction of the side 502.

In addition, a pattern of upstanding fingers or prongs 512 extend from the surface 506 adjacent an edge of the body 500. A plurality of the fingers or prongs 512 may extend in a single row along the edge (across the longitudinal axis of the body 500), or a plurality of the fingers or prongs 512 may extend in a single column from the edge (along the longitudinal axis of the body 500 (as FIG. 60A(1) shows), or a plurality of the fingers or prongs 512 may extend in rows and columns across and along the longitudinal axis of the body 500 (as FIG. 60A(2) shows. The fingers or prongs 512 are sized and configured in use to pierce tissue at the posterior of the tongue (see FIG. 60D). The prongs or fingers 512 are desirably made from a non-rigid material and may have rounded, non-traumatic tips. The prongs or fingers 512 may also have variable stiffness, being more rigid adjacent the body 500 and less rigid adjacent the tip.

Figure 60D:
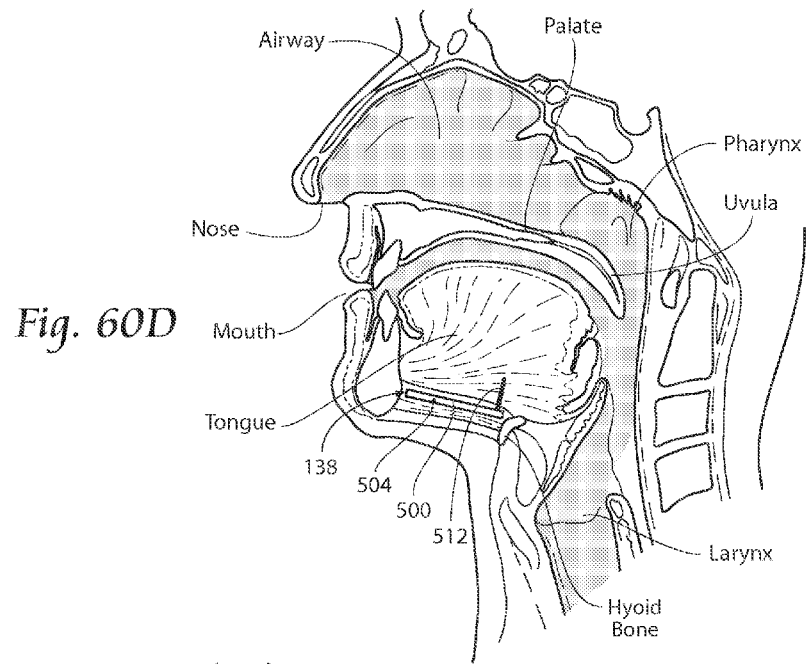
FIGS. 60D and E are anatomic side section views of an oral cavity in an adult human showing the scaffold illustrated in FIGS. 60A to 60C implanted in the floor of the mouth with attachment to the back of the tongue, with FIG. 60D showing the mouth closed and FIG. 60E showing the mouth opened to compress the scaffold and cause preferential bending.

In use, the scaffold 138 is implanted in a tissue structure in, on, or near the floor of the mouth (see FIG. 60D). When implanted, the scaffold 138 is oriented with an anterior region 514 (free of the fingers or prongs 512 facing the mandible and a posterior region 516 (with the fingers or prongs 512 facing the hyoid bone. When implanted, the slotted hinge 510 of the scaffold 138 is oriented toward the feet, i.e., in a caudal direction. In this arrangement, the fingers or prongs 514 extend into and obtain purchase in the posterior (or base) of the tongue.

The presence of the scaffold 138 (which is less flexible than tissue) braces tissue structures in, on, or near the floor of the mouth. Further, compression of the scaffold 138 will occur in response to compression of tissue structures in the floor of the mouth between the mandible and hyoid. The tissue structures will be compressed, e.g., in response to opening the mouth (see FIG. 60E), or posterior translation of the mandible. The tissue structures are compressed when this occurs, because the anterior-to-posterior distance between the hyoid and the mandible shortens.

Figure 60E:
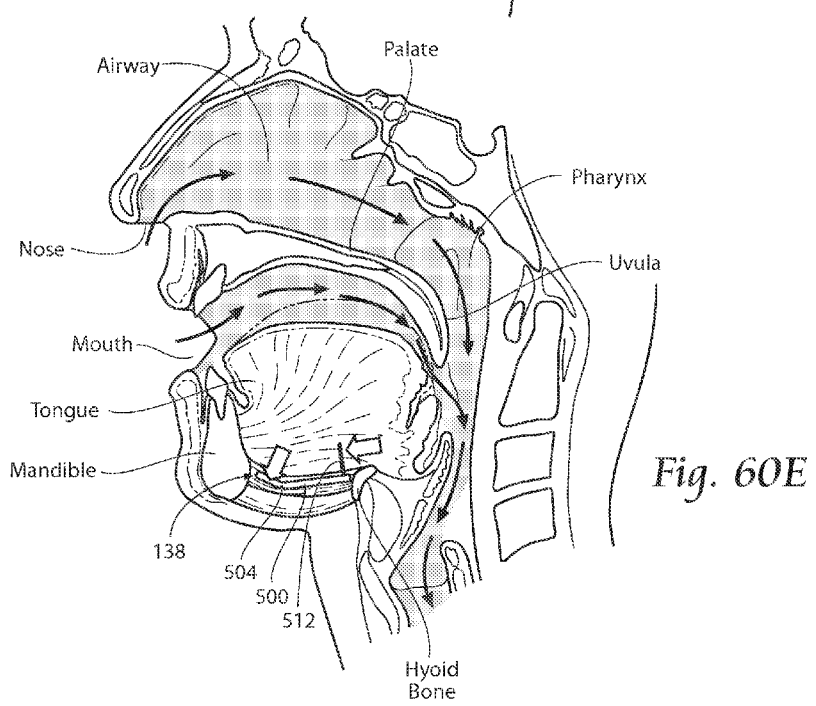
FIGS. 60A to 60C are views of a representative embodiment of a scaffold having a preferential bending function for implantation in the floor of the mouth, and also with attachment to the back of the tongue.

When compressed (as FIG. 60E shows), the scaffold 138 responds by preferentially bending or pivoting in a caudal direction. In this way, the scaffold 138 serves to dynamically brace or bias the tissue structures against collapse in a cranial direction into the airway. Further, by preferentially pivoting, the scaffold 138 applies an anterior lifting force to the back of the tongue, lifting the tongue forward out of the airway.

A scaffold 138 can, if desired, be made from a flexible material with a spring constant. This scaffold 138, when bent, will impart an active spring force in the desired caudal direction. However, a rigid or semi-rigid structure, not having a spring constant per se, can be used, if it is preferably weakened to provide the preferential bending characteristics desired.

Alternatively, the scaffold 138 can be activated by an energy source, e.g., electrical or thermal or magnetic energy or the like, to pivot and assume the outward bend or to stiffen upon demand.

The above-described embodiments of this invention are merely descriptive of its principles and are not to be limited. The scope of this invention instead shall be determined from the scope of the following claims, including their equivalents.

We claim:

1. A system for supporting tissue structures away from an airway through a mouth during sleep, a floor of the mouth being defined anteriorly by a mandible; posteriorly by a hyoid; and including suprahyoid muscles attached to the mandible and/or hyoid, the tissue structures including a tongue within the mouth resting on suprahyoid muscles outside of the floor of the mouth, the system comprising
at least one scaffold structure sized and configured to be implanted outside the tongue between suprahyoid muscles in or on the floor of the mouth and/or outside the tongue between an extrinsic muscle of the tongue and a suprahyoid muscle in or on the floor of the mouth, the scaffold structure having an anterior region that, when implanted, faces the mandible, a posterior region that, when implanted, faces the hyoid, and an intermediate region that, when implanted, extends between the mandible and hyoid, the intermediate region comprising mechanical supporting means for bracing and resisting inward buckling of suprahyoid muscles in or on the floor of the mouth into the airway during sleep, whereby the mechanical supporting means creates a counter force that directs tissue structures out of the airway.

2. The system according to claim 1 wherein the mechanical supporting means is operative for preferentially bending the intermediate region, when implanted, in a caudal direction.

3. The system according to claim 1 further comprising means for attaching the scaffold structure to the mandible and/or the hyoid.

4. The system according to claim 1 wherein the mechanical supporting means is operative for shaping the intermediate region, when implanted, into a convex orientation facing the feet.

5. The system according to claim 1 wherein the mechanical supporting means is operative for shaping the intermediate region, when implanted, to extend longitudinally in an anterior-to-posterior direction.

6. The system according to claim 1 wherein the mechanical supporting means comprises a formed spring structure.

7. The system according to claim 1 wherein the mechanical supporting means includes electrically activated and/or thermally activated and/or magnetically activated material.

8. The system according to claim 1 wherein the mechanical supporting means includes a polymer, or metal, or fiber material, or combinations thereof.

9. The system according to claim 1 further comprising:
a prong structure extending from the posterior region of the scaffold structure into a posterior region of the tongue, the prong structure being sized and configured to obtain purchase in and apply an anterior force to the posterior region of the tongue, whereby, during sleep, while the mechanical supporting means braces and resists inward buckling of suprahyoid muscles in or on the floor of the mouth into an airway, the prong structure applies the anterior force to urge the posterior region of the tongue away from the airway.

10. The system according to claim 9 wherein the prong structure includes a pattern of upstanding fingers.

11. The system according to claim 10 wherein the pattern comprises a single row of upstanding fingers.

12. The system according to claim 10 wherein the pattern comprises more than a single row of upstanding fingers.

13. The system according to claim 1 wherein the mechanical supporting means is operative for shaping the intermediate region into an elongated body.

14. The system according to claim 1 wherein the scaffold structure is sized and configured for implantation between a mylohyoid muscle and a geniohyoid muscle in or on the floor of the mouth.

15. The system according to claim 1 wherein the scaffold structure is sized and configured for implantation between a geniohyoid muscle in or on the floor of the mouth and an extrinsic genioglossus muscle of the tongue.

16. The system according to claim 1 wherein the scaffold structure is sized and configured for implantation between a digastric muscle and a mylohyoid muscle.

17. A method for supporting tissue structures away from an airway through a mouth during sleep, a floor of the mouth being defined anteriorly by a mandible; posteriorly by a hyoid; and including suprahyoid muscles attached to the mandible and/or hyoid, the tissue structures including a tongue within the mouth resting on suprahyoid muscles outside of the floor of the mouth, the method comprising providing a scaffold structure sized and configured for implantation outside the tongue between suprahyoid muscles in or on the floor of the mouth and/or outside the tongue between an extrinsic muscle of the tongue and a suprahyoid muscle in or on the floor of the mouth, the scaffold structure having an anterior region, a posterior region, and an intermediate region, and implanting the scaffold structure outside the tongue between suprahyoid muscles in or on the floor of the mouth and/or outside the tongue between an extrinsic muscle of the tongue and a suprahyoid muscle in or on the floor of the mouth, with the anterior region facing the mandible, the posterior region facing the hyoid, and the intermediate region extending between the mandible and hyoid, whereby the scaffold structure braces and resists inward buckling of suprahyoid muscles in or on the floor of the mouth into the airway during sleep.

18. A method according to claim 17
wherein the implanting comprises implanting the scaffold structure between a mylohyoid muscle and a geniohyoid muscle in or on the floor of the mouth.

19. A method according to claim 17
wherein the implanting comprises implanting the scaffold structure between a geniohyoid muscle in or on the floor of the mouth and an extrinsic genioglossus muscle of the tongue.

20. A method according to claim 17
wherein the implanted comprises implanting the scaffold structure between a digastric muscle and a mylohyoid muscle.

21. A method according to claim 17
wherein providing the scaffold structure comprises providing the scaffold structure as defined in claim 17 and further including a prong structure extending from the posterior region of the scaffold structure toward a posterior region of the tongue, and wherein the implanting includes implanting the scaffold structure as defined in claim 17 and further including implanting the prong structure to obtain purchase in and apply an anterior force to the posterior region of the tongue, whereby, during sleep, while the scaffold structure braces and resists inward buckling of suprahyoid muscles in or on the floor of the mouth into the airway, the prong structure applies the anterior force to urge the posterior region of the tongue away from the airway.

* * * * *